US007416524B1

(12) United States Patent
Lobanov et al.

(10) Patent No.: US 7,416,524 B1
(45) Date of Patent: Aug. 26, 2008

(54) SYSTEM, METHOD AND COMPUTER PROGRAM PRODUCT FOR FAST AND EFFICIENT SEARCHING OF LARGE CHEMICAL LIBRARIES

(75) Inventors: Victor S. Lobanov, Yardley, PA (US); Dimitris K. Agrafiotis, Downington, PA (US); Francis R. Salemme, Yardley, PA (US)

(73) Assignee: Johnson & Johnson Pharmaceutical Research & Development, L.L.C., New Jersey ( * ) Notice: Subject to any disclaimer, the term of this patent is extended or adjusted under 35 U.S.C. 154(b) by 0 days.

(21) Appl. No.: 09/506,741

(22) Filed: Feb. 18, 2000

(51) Int. Cl.
*C40B 30/02* (2006.01)
*G01N 19/00* (2006.01)
*G01N 31/00* (2006.01)

(52) U.S. Cl. .............................. 506/8; 702/19; 702/20; 702/27

(58) Field of Classification Search ................ 435/4; 702/19, 20, 27; 703/11
See application file for complete search history.

(56) References Cited

U.S. PATENT DOCUMENTS

| 4,811,217 | A | 3/1989 | Tokizane et al. ............ 364/300 |
| 4,859,736 | A | 8/1989 | Rink ......................... 525/54.1 |
| 4,908,773 | A | 3/1990 | Pantoliano et al. .......... 364/496 |
| 4,935,875 | A | 6/1990 | Shah et al. .................. 364/497 |
| 4,939,666 | A | 7/1990 | Hardman .................... 364/496 |
| 5,010,175 | A | 4/1991 | Rutter et al. ................ 530/334 |
| 5,025,388 | A | 6/1991 | Cramer, III et al. ......... 364/496 |
| 5,155,801 | A | 10/1992 | Lincoln ....................... 395/22 |
| 5,167,009 | A | 11/1992 | Skeirik ....................... 395/27 |
| 5,240,680 | A | 8/1993 | Zuckermann et al. ........ 422/67 |
| 5,260,882 | A | 11/1993 | Blanco et al. ............... 364/499 |
| 5,265,030 | A | 11/1993 | Skolnick et al. ............. 364/496 |
| 5,270,170 | A | 12/1993 | Schatz et al. ............... 435/7.37 |
| 5,288,514 | A | 2/1994 | Ellman ........................ 427/2 |
| 5,307,287 | A | 4/1994 | Cramer, III et al. ......... 364/496 |
| 5,331,573 | A | 7/1994 | Balaji et al. ................. 364/500 |
| 5,434,796 | A | 7/1995 | Weininger .................. 364/496 |
| 5,436,850 | A | 7/1995 | Eisenberg et al. .......... 364/496 |
| 5,442,122 | A | 8/1995 | Noda et al. ................. 564/426 |
| 5,463,564 | A | 10/1995 | Agrafiotis et al. .......... 364/496 |
| 5,499,193 | A | 3/1996 | Sugawara et al. ........... 364/500 |
| 5,519,635 | A | 5/1996 | Miyake et al. .............. 364/497 |
| 5,526,281 | A | 6/1996 | Chapman et al. ........... 364/496 |
| 5,545,568 | A | 8/1996 | Ellman ....................... 436/518 |
| 5,549,974 | A | 8/1996 | Holmes ....................... 428/403 |
| 5,565,325 | A | 10/1996 | Blake ........................ 435/7.1 |
| 5,574,656 | A | 11/1996 | Agrafiotis et al. .......... 364/500 |
| 5,585,277 | A | 12/1996 | Bowie et al. ............... 436/518 |
| 5,602,755 | A | 2/1997 | Ashe et al. ................. 364/498 |
| 5,612,895 | A | 3/1997 | Balaji et al. ................ 364/496 |
| 5,634,017 | A | 5/1997 | Mohanty et al. ............ 395/326 |
| 5,635,598 | A | 6/1997 | Lebl et al. .................. 530/334 |
| 5,670,326 | A | 9/1997 | Beutel ........................ 435/7.1 |
| 5,679,582 | A | 10/1997 | Bowie et al. ............... 436/518 |
| 5,684,711 | A | 11/1997 | Agrafiotis et al. .......... 364/500 |
| 5,703,792 | A | 12/1997 | Chapman .................... 364/496 |
| 5,712,171 | A | 1/1998 | Zambias et al. ............. 436/518 |
| 5,712,564 | A | 1/1998 | Hayosh ...................... 324/210 |
| 5,736,412 | A | 4/1998 | Zambias et al. ............. 436/518 |
| 5,789,160 | A | 8/1998 | Eaton et al. ................. 435/6 |
| 5,807,754 | A | 9/1998 | Zambias et al. ............. 436/518 |
| 5,811,241 | A | 9/1998 | Goodfellow et al. ........ 435/7.1 |
| 5,832,494 | A | 11/1998 | Egger et al. ................ 707/102 |
| 5,858,660 | A | 1/1999 | Eaton et al. ................. 435/6 |
| 5,861,532 | A | 1/1999 | Brown et al. ............... 564/142 |
| 5,866,334 | A | 2/1999 | Beutel ......................... 435/6 |
| 5,901,069 | A | 5/1999 | Agrafiotis et al. ........ 364/528.03 |
| 5,908,960 | A | 6/1999 | Newlander ................. 564/177 |
| 5,933,819 | A | 8/1999 | Skolnick et al. ............ 706/21 |
| 6,037,135 | A | 3/2000 | Kubo et al. ................ 435/7.24 |
| 6,049,797 | A | 4/2000 | Guha et al. .................. 707/6 |
| 6,127,191 | A | * 10/2000 | Graybill et al. ............. 436/518 |
| 6,185,506 | B1 | 2/2001 | Cramer et al. .............. 702/19 |
| 6,240,374 | B1 | * 5/2001 | Cramer et al. .............. 703/11 |

(Continued)

FOREIGN PATENT DOCUMENTS

EP 0 355 266 B1 6/1993

(Continued)

OTHER PUBLICATIONS

"3DP Gains drug research patent," Source of publication unclear, vol. 32, No. 1, Jan. 1996, 2 pages.

(Continued)

*Primary Examiner*—Lori A Clow

(57) ABSTRACT

A system, method, and computer program product for fast and efficient searching of large virtual combinatorial libraries based on a fitness function. According to the method of the present invention, a first set of N reagent combinations are selected, for example, at random, from a virtual combinatorial library. Each reagent combination in the first set is then enumerated to produce a first set of enumerated compounds. M number of compounds of the first set of enumerated compounds are selected based on the fitness function. The M compounds are then deconvoluted into reagents to generate a focused library. Substantially every reagent combination associated with the focused library is enumerated to produce a second set of enumerated compounds. K number of compounds of the second set of enumerated compounds are then selected based on the fitness function. These K compounds represent a near optimal selection of compounds based on the fitness function.

17 Claims, 24 Drawing Sheets

U.S. PATENT DOCUMENTS 6,253,168 B1 * 6/2001 Griffey et al. .................. 703/12

FOREIGN PATENT DOCUMENTS

| EP | 0 355 628 B1 | 11/1993 |
|---|---|---|
| EP | 0 770 876 A1 | 5/1997 |
| EP | 0 818 744 A2 | 1/1998 |
| WO | WO 91/19735 | 12/1991 |
| WO | WO 92/00091 | 1/1992 |
| WO | WO 93/20242 | 10/1993 |
| WO | WO 94/28504 | 12/1994 |
| WO | WO 95/01606 | 1/1995 |
| WO | WO 97/09342 | 3/1997 |
| WO | WO 97/20952 | 6/1997 |
| WO | WO 97/27559 | 7/1997 |
| WO | WO 98/20437 | 5/1998 |
| WO | WO 98/20459 | 5/1998 |

OTHER PUBLICATIONS

Agrafiotis, D.k., "A New Method for Analyzing Protein Sequence Relationships Based on Sammon Maps," *Protein Science*, vol. 6, No. 2, Feb. 1997, pp. 287-293.

Agrafiotis, D.K., et al., "Stochastic Algorithms for Maximizing Molecular Diversity," *Journal of Chemical Information and Computer Sciences*, vol. 37, pp. 841-851, (1997).

Alsberg, B.K. et al., "Classification of pyrolysis mass spectra by fuzzy multivariate rule induction-comparison with regression, K-nearest neighbor, neural and decision-tree methods," *Analytica Chimica Acta*, vol. 348, No. 1-3, pp. 389-407, (Aug. 20, 1997).

Amzel, L.M., "Structure-based drug design," *Current Opinion in Biotechnology*, vol. 9, No. 4, Aug. 1998, pp. 366-369.

Andrea, T.A. et al., "Applications of Neural Networks in Quantitative Structure-Activity Relationships of Dihydrofolate Reductase Inhibitors," *Journal of Medicinal Chemistry*, vol. 34, No. 9, pp. 2824-2836, (1991).

Aoyama, T. et al., "Neural Networks Applied to Quantitative Structure-Activity Relationship Analysis," *Journal of Medicinal Chemistry*, vol. 33, No. 9, pp. 2583-2590, (1990).

Aoyama, T. et al., "Neural Networks Applied to Structure-Activity Relationships," *Journal of Medicinal Chemistry*, vol. 33, No. 3, pp. 905-908, (1990).

Aoyama, T. and Hiroshi Ichikawa, "Obtaining the Correlation Indices between Drug Activity and Structural Parameters Using a Neural Network," *Chemical & Pharmaceutical Bulletin*, vol. 39, No. 2, pp. 372-378, (1991).

"ArQule Inc," from http://www.bioportfolio.com/argule/products.htm, 5 pages, (Mar. 18, 1998).

Baum, R.M., "Combinatorial Approaches Provide Fresh Leads for Medicinal Chemistry," *Chemical & Engineering News*, Feb. 7, 1994 (pp. 20-26).

Bentley, J.L., "Multidimensional Binary Search Trees Used for Associative Searching," *Communications of the ACM*, vol. 18, No. 9, pp. 509-517, (Sep. 1975).

Blaney, J.M. and Martin, E.J., "Computational approaches for combinatorial library design and molecular diversity analysis," *Current Opinion in Chemical Biology*, vol. 1, No. 1, Jun. 1997, pp. 54-59.

Bottou, L. and Vladimir Vapnik, "Local Learning Algorithms," *Neural Computation*, vol. 4, No. 6, pp. 888-900, (Nov. 1992).

Boulu, L.G. and Gordon M. Crippen, "Voronoi Binding Site Models: Calculation of Binding Modes and Influence of Drug Binding Data Accuracy," *Journal of Computational Chemistry*, vol. 10, No. 5, pp. 673-682, (1989).

Boulu, L.G. et al., "Voronoi Binding Site Model of a Polycyclic Aromatic Hydrocarbon Binding Protein," *Journal of Medicinal Chemistry*, vol. 33, No. 2, pp. 771-775, (1990).

Brown, R.D. and Clark, D.E., "Genetic Diversity: Applications of evolutionary algorithms to combinatorial library design," *Expert Opinion on Therapeutic Patents*, vol. 8, No. 11, Nov. 1998, pp. 1447-1459.

Brown, R.D. and Yvonne C. Martin, "Use of Structure-Activity Data To Compare Structure-Based Clustering Methods and Descriptors for Use in Compound Selection," *Journal of Chemical Information and Computer Sciences*, vol. 36, No. 3, pp. 572-584, (1996).

Cacoullos, T., "Estimation of a Multivariate Density", *Annals of The Institute of Statistical Mathematics*, vol. 18, No. 2, pp. 179-189, (1966).

Caflisch, A. and Karplus, M., "Computational combinatorial chemistry for de novo ligand design: Review and assessment," *Perspectives in Drug Discovery and Design*, vol. 3, 1995, pp. 51-84.

Clark, D. E., and David R. Westhead, "Evolutionary algorithms in computer-aided molecular design", *Journal of Computer-Aided Molecular Design*, vol. 10, No. 4, pp. 337-358, (Aug. 1996).

Clark, R.D., "OptiSim: An Extended Dissimilarity Selection Method for Finding Diverse Representative Subsets", *Journal of Chemical Information and Computer Sciences*, vol. 37, No. 6, pp. 1181-1188 (12 Page Internet printout), 1997.

Cramer, R. D. III et al., "Comparative Molecular Field Analyisis (CoMFA). 1. Effect of Shape on Binding of Steroids to Carrier Proteins", *Journal of The American Chemical Society*, vol. 110, No. 18, pp. 5959-5967, (Aug. 31, 1988).

Cramer, R. D. III et al., "Substructural Analysis. A Novel Approach to the Problem of Drug Design", *Journal of Medicinal Chemistry*, vol. 17, No. 5, pp. 533-535, (May 1974).

Crippen, G. M., "Voronoi binding Site Models", *Journal of Computational Chemistry*, vol. 8, No. 7, pp. 943-955, (Oct./Nov. 1987).

Danheiser, S.L., "Current Trends in Synthetic Peptide and Chemical Diversity Library Design," *Genetic Engineering News*, May 1, 1994, pp. 10 and 31.

Eichler, U. et al., "Addressing the problem of molecular diversity," *Drugs of the Future*, vol. 24, No. 2, 1999, pp. 177-190.

Felder, E.R. and Poppinger, D., "Combinatorial Compound Libraries for Enhanced Drug Discovery Approaches," *Advances in Drug Research*, vol. 30, 1997, pp. 112-199.

Friedman, J. H. et al., "An Algorithm for Finding Best Matches in Logarithmic Expected Time", *ACM Transactions on Mathematical Software*, vol. 3, No. 3, pp. 209-226, (Sep. 1997).

Friedman, J.H., "Fitting Functions To Noisy Data In High Dimensions", Department of Statistics- Stanford University Technical Report No. 101, (Aug. 1988).

Gallop, M. A. et al., "Applications of Combinatorial Technologies to Drug Discovery. 1. Background and Peptide Combinatorial Libraries", *Journal of Medicinal Chemistry*, vol. 37, No. 9, pp. 1233-1251, (Apr. 29, 1994).

Geysen, H.M. and Mason, T.J., "Screening Chemically Synthesized Peptide Libraries for Biologically-Relevant Molecules," *Biorganic & Medicinal Chemistry Letters*, vol. 3, No. 3, 1993, pp. 397-404.

Ghose, A. K. and Gordon M. Crippen, "Use of Physicochemical Parameters in Distance Geometry and Related Three-Dimensional Qantitative Structure-Activity Relationships: A Demonstration Using *Escherichia coli* Dihydrofolate Reductase Inhibitors", *Journal of Medicinal Chemistry*, vol. 28, No. 3, pp. 333-346, (1985).

Gobbi, A. et al., "New Leads By Selective Screening of Compounds From Large Databases," *Abstracts for CINF sponsored symposia*, Apr. 17, 1997, p. 22.

Good, A. C. et al., "Structure-Activity Relationships from Molecular Similarity Matrices", *Journal of Medicinal Chemistry*, vol. 36, No. 4, pp. 433-438, (Feb. 19, 1993).

Gordon, E. M., "Applications of Combinatorial Technologies to Drug Discovery. 2. Combinatorial Organic Synthesis, Library Screening Strategies, and Future Directions", *Journal of Medicinal Chemistry*, vol. 37, No. 10, (May 13, 1994).

Grayhill, T.L. et al., "Enhancing the Drug Discovery Process by Integration of High-Throughput Chemistry and Structure-Based Drug Design," from *Molecular Diversity and Combinatorial Chemistry: Libraries and Drug Discovery*, Chaiken and Janda (eds.), American Chemical Society, 1996, pp. 16-27.

Hartigan, J. A., "Representation of Similarity Matrices By Trees", *Journal of the American Statistical Association*, vol. 62, No. 320, pp. 1140-1158, (Dec. 1967).

Hopfinger, A. J., "A QSAR Investigation of Dihydrofolate Reductase Inhibition by Baker Triazines based upon Molecular Shape Analysis", *Journal of the American Chemical Society*, vol. 102, No. 24, pp. 7196-7206, (Nov. 19, 1980).

Houghten, R.A. et al., "The Use of Synthetic Peptide Combinatorial Libraries for the Identification of Bioactive Peptides," *Peptide Research*, vol. 5, No. 6, 1992, pp. 351-358.

Jackson, R. C., "Update on computer-aided drug design", *Current Opinion in Biotechnology*, vol. 6, No. 6, pp. 646-651, (Dec. 1995).

Kim, K. H., "Comparative molecular field analysis (CoFMA)", *Molecular Similarity in Drug Design*, ed. P. M. Dean, Blackie Academic & Professional, 1995, Ch. 12 (pp. 291-324).

Klopman, G., "Artificial Intelligence Approach to Structure-Activity Studies. Computer Automated Structure Evaluation of Biological Activity of Organic Molecules," *J. Am. Chem. Soc.*, vol. 106, No. 24, Nov. 28, 1984, pp. 7315-7321.

Kohonen, T., "Self-Organized Formation of Topologically Correct Feature Maps", *Biological Cybernetics*, vol. 43, pp. 59-69, (1982).

Koile, K. and Richard Shapiro, "Building A Collaborative Drug Design System", *Proceedings of the 25h Hawaii International Conference on System Sciences*, pp. 706-716, (1992).

Kowalski, B. R. and C. F. Bender, "Pattern Recognition. II. Linear and Nonlinear Methods for Displaying Chemical Data", *Journal of the American Chemical Society*, pp. 686-693, (Feb. 7, 1973).

Kruskal, J. B., "Nonmetric Multidimensional Scaling: A Numerical Method", *Psychometrika*, vol. 29, No. 2, pp. 115-129, (Jun. 1964).

Lajiness, M.S. et al., "Implementing Drug Screening Programs Using Molecular Similarity Methods," *QSAR: Quantitative Structure-Activity Relationships in Drug Design*, 1989, pp. 173-176.

Lengauer, T. and Matthias Rarey, "Computational methods for biomolecular docking" *Current Opinion in Structural Biology*, vol. 6, No. 3, pp. 402-406, (Jun. 1996).

Loew, G.H. et al., "Strategies for Indirect Computer-Aided Drug Design," *Pharmaceutical Research*vol. 10, No. 4, 1993, pp. 475-486.

Luke, B. T., "Evolutionary Programming Applied to the Development of Quantitative Structure-Activity Relationships and Quantitative Structure-Property Relationships", *Journal of Chemical Information and Computer Sciences*, vol. 34, pp. 1279-1287, (Nov./Dec. 1994).

Lynch, M.F. et al., "Generic Structure Storage and Retrieval," *J. Chem. Inf. Comput. Sci.*, vol. 25, No. 3, Aug. 1985, pp. 264-270.

Martin, E. J. et al., "Does Combinatorial Chemistry Obviate Computer-Aided Drug Design?", *Reviews in Computational Chemistry*, vol. 10, pp. 75-99, (1997).

Martin, E. J. et al., "Measuring Diversity: Experimental Design of Combinatorial Libraries for Drug Discovery", *Journal of Medicinal Chemistry*, vol. 38, No. 9, pp. 1431-1436, (Apr. 28, 1995).

McMartin, C. and Regine S. Bohacek, "QXP: Powerful, rapid computer algorithms for structure-based drug design", *Journal of Computer-Aided Molecular Design*, vol. 11, pp. 333-344, (1997).

Mezey, P. G. and P. Duane Walker, "Fuzzy molecular fragments in drug research", *Drug Discovery Today*, vol. 2, No. 4, (Apr. 1997).

Müller, K., "On the paradigm shift from rational to random design", *Journal of Molecular Structure (Theochem)398-399*, Special Issue, pp. 467-471, (1997).

Myers, P.L. et al., "Rapid, Reliable Drug Discovery," *Today's Chemist At Work*, Jul./Aug. 1997, pp. 46-48, 51 & 53.

Pabo et al., "Computer-Aided Model Building Strategies for Protein Design," *Biochemistry*, vol. 25, No. 20, 1986, pp. 5987-5991.

Parrill, A. L., "Evolutionary and genetic methods in drug design", *Drug Discovery Today*, vol. 1, No. 12, pp. 514-521, (Dec. 1996).

Polanski, J., "A neural network for the simulation of biological systems", *Journal of Molecular Structure (Theochem)398-399*, Special Issue, pp. 565-571, (1997).

Ramos-Nino, M. E. et al., "A comparison of quantitative structure-activity relationships for the effect of benzoic and cinnamic acids on *Listeria monocytogenes* using multiple linear regression, artificial neural network and fuzzy systems", *Journal of Applied Microbiology*, vol. 82, No. 2, pp. 168-175, (Feb. 1997).

Rogers, D. and A. J. Hopfinger, "Application of Genetic Function Approximation to Quantitative Structure-Activity Relationships and Quantitative Structure-Property Relationships", *Journal of Chemical Information and Computer Sciences*, vol. 34, No. 4, pp. 854-866, (Jul./Aug. 1994).

Sammon, J. W., Jr., "A Nonlinear Mapping for Data Structure Analysis", *IEEE Transactions on Computers*, vol. C-18, No. 5, pp. 401-409, (May, 1969).

Saudek et al., "Solution Conformation of Endothelin-1 by H NMR, CD, and Molecular Modeling," *International Journal of Peptide Protein Res.*, vol. 37, No. 3, 1991, pp. 174-179.

Saund, E., "Dimensionality-Reduction Using Connectionist Networks," *IEEE Transactions on Pattern Analysis and Machine Intelligence*, vol. 11, No. 3, Mar. 1989, pp. 304-314.

Simon, Z. et al., "Mapping of Dihydrofolate-reductase Receptor Site by Correlation with Minimal Topological (Steric) Differences", *Journal of Theoretical Biology*, vol. 66, No. 3, pp. 485-495, (Jun. 7, 1997).

Singh, J. et al., "Application of Genetic Algorithms to Combinatorial Synthesis: A Computational Approach to Lead Identification and Lead Optimization," *J. Am. Chem. Soc.*, vol. 118, No. 7, Feb. 21, 1996, pp. 1669-1676.

Smellie, A. S. et al., "Fast Drug-Receptor Mapping by Site-Directed Distances: A Novel Method of Predicting New Pharmacological Leads", *Journal of Chemical Information and Computer Sciences*, vol. 31, No. 3, pp. 386-392, (Aug. 1991).

Specht, D. F., "A General Regression Neural Network", *IEEE Transactions on Neural Networks*, vol. 2, No. 6, pp. 568-576, (Nov. 1991).

Svozil, D. et al., "Neural Network Prediction of the Solvatochromic Polarity/Polarizability Parameter $\Pi^H_2$,", *Journal of Chemical Information and Computer Sciences*, vol. 37, No. 2, (1997).

Todorov, N. P. and P. M. Dean, "Evaluation of a method for controlling molecular scaffold diversity in de novo ligand design", *Journal of Computer-Aided Molecular Design*, vol. 11, pp. 175-192, (1997).

Torgerson, W. S., "Multidimensional Scaling: I. Theory and Method", *Psychometrika*, vol. 17, No. 4, pp. 401-419, (Dec. 1952).

Van Drie, J.H. and Lajiness, M.S., "Approaches to virtual library design," *Drug Discovery today*, vol. 3, No. 6, Jun. 1998, pp. 274-283.

Vapnik, V. and L. Bottou, "Local Algorithms for Pattern Recognition and Dependencies Estimation", *Neural Computation*, vol. 5, No. 6, pp. 893-909, (Nov. 1993).

Viswanadhan, V. N. et al., "Mapping the binding site of the nucleoside transporter protein: a 3D-QSAR study", *Biochimica et Biophysica Acta*, vol. 1039, No. 3, pp. 356-366, (1990).

Walters, W.P., "Virtual screening—an overview," *Drug Discovery today*, vol. 3, No. 4, Apr. 1998, pp. 160-178.

Warr, W. A., "Exploiting Molecular Diversity: Small Molecule Libraries for Drug Discovery", Report of Conference held in La Jolla, California, Jan. 23-25, 1995.

Weber, L., "Evolutionary combinatorial chemistry: application of genetic algorithms," *Drug Discovery today*, vol. 3, No. 8, Aug. 1998, pp. 379-385.

Weber, L. et al., "Optimization of the Biological Activity of Combinatorial Compound Libraries by a Genetic Algorithm," *Angewandte Chemie International Edition in English*, vol. 34, No. 20, 1995, pp. 2280-2282.

Westhead, D. R. et al., "A comparison of heuristic search algorithms for molecular docking", *Journal of Computer-Aided Molecular Design*, vol. 11, pp. 209-228, (1997).

Willett, P., "Genetic algorithms in molecular recognition and design", *Trends in Biotechnology*, vol. 13, No. 12, pp. 516-521, (Dec. 1995).

Willett, P. and Vivienne Winterman, "A Comparison of Some Measures for the Determination of Inter-Molecular Structural Similarity Measures of Inter-Molecular Structural Similarity", *Quantitative Structure-Activity Relationships*, vol. 5, No. 1, pp. 18-25, (Mar. 1986).

Zadeh, L. A., "Communication Fuzzy Algorithms", *Information and Control*, vol. 12, No. 2, pp. 94-102, (Feb. 1968).

Zadeh, L. A., "Fuzzy Sets", *Information and Control*, vol. 8, No. 3, pp. 338-353, (Jun. 1965).

Borg, Inger and Groenen, Patrick, *Modern Multidimensional Scaling Theory and Applications*, Springer Series in Statistics, 1997, entire book submitted.

Agrafiotis, D.K. et al., "Advances in diversity profiling and combinatorial series design," *Molecular Diversity*, vol. 4, 1999, pp. 1-22.

Agrafiotis, D.K. and Lobanov, V.S., "An Efficient Implementation of Distance-Based Diveristy Measure based on *k-d* Trees," *J. Chem. Inf. Comput. Sci.*, vol. 39, No. 1, Jan./Feb. 1999, pp. 51-58.

Agrafiotis, D.K. and Lobanov, V.S., "Bridging The Gap Between Diversity And QSAR," *Abstracts of Papers Part 1: 215th ACS National Meeting*, Mar. 29-Apr. 2, 1998, p. 181-COMP.

Agrafiotis, D.K. and Jaeger, E.P., "Directed Diversity® : An Operating System For Combinatorial Chemistry," *Abstracts of Papers Part 1: 211th ACS National Meeting*, Mar. 24-28, 1996, p. 46-COMP.

Agrafiotis, D.K., "Diversity of Chemical Libraries," *Encyclopedia of Computational Chemistry*, vol. 1:A-D, 1998, pp. 742-761.

Agrafiotis, D.K., "On the Use of Information Theory for Assessing Molecular Diversity," *J. Chem. Inf. Comput. Sci.*, vol. 37, No. 3, May/Jun. 1997, pp. 576-580.

Agrafiotis, D.K. et al., "Parallel QSAR," *Abstracts of Papers Part 1: 217th ACS National Meeting*, Mar. 21-25, 1999, p. 50-COMP.

Agrafiotis, D.K. et al., "PRODEN: A New Program for Calculating Integrated Projected Populations," *Journal of Computational Chemistry*, vol. 11, No. 9, Oct. 1990, pp. 1101-1110.

Agrafiotis, D.K. and Jaeger, E.P., "Stochastic Algorithms for Exploring Molecular Diversity," *Abstracts of Papers Part 1: 213th ACS National Meeting*, Apr. 13-17, 1997, p. 16-CINF.

Agrafiotis, D., "Theoretical Aspects of the Complex: Arts and New Technologies," *Applications and Impacts Information Processing '94*, vol. II, 1994, pp. 714-719.

Biswas, G. et al., "Evaluation of Projection Algorithms," *IEEE Transactions On Pattern Analysis And Machine Intelligence*, vol. PAMI-3, No. 6, Nov. 1981, pp. 701-708.

Bonchev, D. and Trinajsti, N., "Information theory, distance matrix, and molecular branching," *The Journal of Chemical Physics*, vol. 67, No. 10, Nov. 15, 1977, pp. 4517-4533.

Chang, C.L. and Lee, R.C.T., "A Heuristic Relaxation Method for Nonlinear Mapping in Cluster Analysis," *IEEE Transactions on Systems, Man, and Cybernetics*, vol. SMC-3, Mar. 1973, pp. 197-200.

Cramer, R.D. et al., "Virtual Compound Libraries: A New Approach to Decision Making in Molecular Discovery Research," *J. Chem. Inf. Comput. Sci.*, vol. 38, No. 6, Nov./Dec. 1998, pp. 1010-1023.

DeMers, D. and Cottrell, G., "Non-Linear Dimensionality Reduction," *Advances in Neural Information Processing Systems*, vol. 5, 1993, pp. 580-587.

Frey, P. W. and Slate, D.J., "Letter Recognition Using Holland-Style Adaptive Classifiers," *Machine Learning*, vol. 6, 1991, pp. 161-182.

Friedman, J.H., "Exploratory Projection Pursuit," *Journal of the American Statistical Association*, vol. 82, No. 397, Mar. 1987, pp. 249-266.

Friedman, J.H. and Tukey, J.W., "A Projection Pursuit Algorithm for Exploratory Data Analysis," *IEEE Transactions on Computers*, vol. C-23, No. 9, Sep. 1974, pp. 881-889.

Garrido, L. et al., "Use of Multilayer Feedforward Neural Nets As A Display Method for Multidimensional Distributions," *International Journal of Neural Systems*, vol. 6, No. 3, Sep. 1995, pp. 273-282.

Ghose, A.K. et al., "Prediction of Hydrophobic (Lipophilic) Properties of Small Organic Molecules Using Fragmental Methods: An Analysis of ALOGP and CLOGP Methods," *J. Phys. Chem. A*, vol. 102, No. 21, May 12, 1998, pp. 3762-3772.

Hall, L.H. and Kier, L.B., "The Molecular Connectivity Chi Indexes and Kappa Shape Indexes in Stucture-Property Modeling," *Reviews in Computational Chemistry: Advances*, 1991, pp. 367-422.

Hecht-Nielsen, R., "Replicator Neural Networks for Universal Optimal Source Coding," *Science*, vol. 269, Sep. 29, 1995, pp. 1860-1863.

Hotelling, H., "Analysis of a Complex of Statistical Variables into Principal Components," *The Journal of Educational Psychology*, vol. XXIV, No. 6, Sep. 1933, pp. 417-441.

Hotelling, H., "Analysis of a Complex of Statistical Variables into Principal Components," *The Journal of Educational Psychology*, vol. XXIV, No. 7, Oct. 1933, pp. 498-520.

Lee, R.C.T. et al., "A Triangulation Method for the Sequential Mapping of Points from $N$-Space to Two-Space," *IEEE Transactions on Computers*, Mar. 1977, pp. 288-292.

Lipinski, C.A. et al., "Experimental and computational approaches to estimate solubility and permeability in drug discovery and development settings," *Advanced Drug Delivery Reviews*, vol. 23, 1997, pp. 3-25.

Lobanov, V.S. and Agrafiotis, D.K., "Intelligent Database Mining Techniques," *Abstracts of Papers Part 1: 215th ACS National Meeting*, Mar. 29-Apr. 2, 1998, p. 19-COMP.

Lobanov, V.S. et al., "Rational Selections from Virtual Libraries," *Abstracts of Papers Part 1: 217th ACS National Meeting*, Mar. 21-25, 1999, p. 181-COMP.

Mao, J. and Jain, A.K., "Artificial Neural Networks for Feature Extraction and Multivariate Data Projection," *IEEE transactions on Neural Networks*, vol. 6, No. 2, Mar. 1995, pp. 296-317.

Oja, E., "Principal Components, Minor Components, and Linear Neural Networks," *Neural Networks*, vol. 5, 1992, pp. 927-935.

Patterson, D.E. et al., "Neighborhood Behavior: A Useful Concept for Validation of 'Molecular Diversity' Descriptors," *Journal of Medicinal Chemistry*, vol. 39, No. 16, 1996, pp. 3049-3059.

Pykett, C.E., "Improving the Efficiency of Sammon's Nonlinear Mapping by Using Clustering Archetypes," *Electronics Letters*, vol. 14, No. 25, Dec. 7, 1978, pp. 799-800.

Rubner, J. and Tavan, P., "A Self-Organizing Network for Principal-Component Analysis," *Europhysics Letters*, vol. 10, No. 7, Dec. 1, 1989, pp. 693-698.

Sadowski, J. et al., "Assessing Similarity and Diversity of Combinatorial Libraries by Spatial Autocorrelation Functions and Neural Networks," *Angewandte Cheme*, vol. 34, No. 23/24, Jan. 5, 1996, pp. 2674-2677.

Thompson, L.A. and Ellman, J.A., "Synthesis and Applications of Small Molecule Libraries," *Chemical Reviews*, vol. 96, No. 1, Jan./Feb. 1996, pp. 555-600.

Barnard, John M. and Downs, Geoff M., "Computer representation and manipulation of combinatorial libraries," *Perspectives in Drug Discovery and Design*, 1997, pp. 13-30.

Brint, Andrew T. and Willett, Peter, "Upperbound procedures for the identification of similar three-dimensional chemical structures," *Journal of Computer-Aided Molecular Design*, vol. 2, No. 4, 1988, pp. 311-320.

Brown, Robert D. and Martin, Yvonne C., "Designing Combinatorial Library Mixtures Using a Genetic Algorithm," *Journal of Medicinal Chemistry*, vol. 40, No. 15, 1997, pp. 2304-2313.

Gasteiger, J. et al., "Analysis of the Reactivity of Single Bonds in Aliphatic Molecules by Statistical and Pattern Recognition Methods," *Journal of Chemical Information Computer Science*, vol. 33, No. 3, 1993, pp. 385-394.

Gillet, Valerie J. et al., "The Effectiveness of Reactant Pools for Generating Structurally-Diverse Combinatorial Libraries," *Journal of Chemical Information Computer Sciences*, vol. 37, No. 4, 1997, pp. 731-470.

Gillet, Valerie J. et al., "Selecting Combinatorial Libraries to Optimize Diversity and Physical Properties," *Journal of Chemical Information Computer Sciences*, vol. 39, No. 1, 1999, pp. 169-177.

Guez, Allon and Nevo, Igal, "Neural networks and fuzzy logic in clinical laboratory computing with application to integrated monitoring," *Clinica Chimica Acta*, 248, 1996, pp. 73-90.

Kearsley, Simon K. et al., "Chemical Similarity Using Physiochemical Property Descriptors," *Journal of Chemical Information Computer Science*, 36, 1996, pp. 118-127.

Leland, Burton A. et al., "Managing the Combinatorial Explosion," *Journal of Chemical Information Computer Science*, 37, 1997, pp. 62-70.

Lewis, Richard A. et al., "Similarity Measures for Rational Set Selection and Analysis of Combinatorial Libraries: The Diverse Property-Derived (DPD) Approach," *Journal of Chemical Information Computer Science*, 37, 1997, pp. 599-614.

Martin, Eric J. and Critchlow, Roger E., "Beyond Mere Diversity: Tailoring Combinatorial Libraries for Drug Discovery," *Journal of Combinatorial Chemistry*, vol. 1, No. 1, 1999, pp. 32-45.

Sen, K. (ed.), *Molecular Similarity I*, Springer-Verlag, 1995, pp. 1-30.

Sheridan, Robert P. et al., "Chemical Similarity Using Geometric Atom Pair Descriptors," *Journal of Chemical Information Computer Science*, 36, 1996, pp. 128-136.

Willett, Peter et al., "Chemical Similarity Searching," *Journal of Chemical Information Computer Science*, 38, 1998, pp. 983-996.

Agrafiotis, Dimitris K. and Lobanov, Victor S., "Ultrafast Algorithm for Designing Focused Combinational Arrays," *J. Chem. Inf. Comput. Sci.*, Jun. 16, 2000, vol. 40, pp. 1030-1038.

Ajay, W. Patrick Walters and Murcko, Mark A., "Can We Learn To Distinguish between "Drug-Like" and "Nondrug-like" Molecules?" *J. Med. Chem.*, Jul. 23, 1998, vol. 41, pp. 3314-3324.

Brown, Robert D. and Martin, Yvonne C., "Designing Combinatorial Library Mixtures Using a Genetic Algorithm," *J. Med. Chem.*, 1997, vol. 40, pp. 2304-2313.

Brown, Robert D. and Martin, Yvonne C., "The Information Content of 2D and 3D Structural Descriptors Relevant to Ligand-Receptor Binding," *J. Chem. Info. Comput. Sci.*, 1997, vol. 37, pp. 1-9.

Brown, Robert D. and Martin, Yvonne C., "Use of Structure-Activity Data To Compare Structure-Based Clustering Methods and Descriptors for Use in Compound Selection," *J. Chem. Inf. Sci.*, 1996, vol. 36, pp. 572-584.

Cummins, David J. et al., "Molecular Diversity in Chemical Databases: Comparison of Medicinal Chemistry Knowledge Bases and Databases of Commercially Available Compounds," *American Chemical Society*, 1996, 14 pages.

*Daylight Theory: Fingerprints* (visited Sep. 26, 2000) <http://www.daylight.com/dayhtml/doc/theory/theory.finger.html>, 8 pages.

*Daylight Theory: SMARTS* (visited Sep. 26, 2000) <http://www.daylight.com/dayhtml/doc/theory/theory.smarts.html>, 10 pages.

Downs, Geoff M. and Barnard, John M., "Techniques for Generating Descriptive Fingerprints in Combinatorial Libraries," *J. Chem. Inf. Comput. Sci.*, 1997, vol. 37, pp. 59-61.

Gillet, Valerie J., "Background Theory of Molecular Diversity," *Molecular Diversity in Drug Design*, 1999, pp. 43-65.

Good, Andrew C. and Lewis, Richard A., "New Methodology for Profiling Combinatorial Libraries and Screening Sets: Cleaning Up the Design Process with HARPick," *J. Med. Chem.*, 1997, vol. 40, pp. 3926-3936.

Gorse, Dominique and Lahana, Roger, "Functional diversity of compound libraries," *Current opinion in chemical biology*, 2000, vol. 4, pp. 287-294.

Jamois, Eric A. et al., "Evaluation of Reagent-Based and Product-Based Strategies in the Design of Combinatorial Library Subsets," *J. Chem. Inf. Comput. Sci.*, Dec. 9, 1999, vol. 40, pp. 63-70.

Leach, Andrew R. et al., "Implementation of a System for Reagent Selection and Library Enumeration, Profiling, and Design," *J. Chem. Inf. Comput. Sci.*, Oct. 29, 1999, vol. 39, pp. 1161-1172.

Leach, Andrew R. and Hann, Michael M., "The *in silico* world of virtual libraries," *Drug discovery today*, Aug. 2000, vol. 5, pp. 326-336.

Leland, Burton A. et al., "Managing the Combinatorial Explosion," *J. Chem. Inf. Comput. Sci.*, 1997, vol. 37, pp. 62-70.

Lobanov, Victor S. and Agrafiotis, Dimitris K., "Stochastic Similarity Selections from Large Combinatorial Libraries," *J. Chem. Inf. Comput. Sci.*, Jan. 21, 2000, vol. 40, pp. 460-470.

Matter, Hans and Pötter, Thorsten, "Comparing 3D Pharmacophore Triplets and 2D Fingerprints for Selecting Diverse Compound Subsets," *J. Chem. Inf. Comput. Sci.*, Oct. 29, 1999, vol. 39, pp. 1211-1225.

Matter, Hans, "Selecting Optimally Diverse Compounds from Structure Databases: A Validation Study of Two-Dimensional and Three-Dimensional Molecular Descriptors," *J. Med. Chem.*, 1997, vol. 40, pp. 1219-1229.

Sadowski, Jens and Kubinyi, Hugo, "A Scoring Scheme for Discriminating between Drugs and Nondrugs," *J. Med. Chem.*, Aug. 1, 1998, vol. 41, pp. 3325-3329.

Schnur, Dora, "Design and Diversity Analysis of Large Combinatorial Libraries Using Cell-Based Methods," *J. Chem. Inf. Comput. Sci.*, Jan. 6, 1999, vol. 39, pp. 36-45.

Schuffenhauer, Ansgar et al., "Similarity Searching in Files of Three-Dimensional Chemical Structures: Analysis of the BIOSTER Database Using Two-Dimensional Fingerprints and Molecular Field Descriptors," *J. Chem. Inf. Comput. Sci.*, Dec. 22, 1999, vol. 40, pp. 295-307.

Turner, David B. et al., "Rapid Quantification of Molecular Diversity for Selective Database Acquisition," *J. Chem. Inf. Sci.*, 1997, vol. 37, pp. 18-22.

Wang, Jing and Ramnarayan, Kal, "Toward Designing Drug-Like Libraries: A Novel Computational Approach for Prediction of Drug Feasibility of Compounds," *J. Comb. Chem.*, Oct. 19, 1999, vol. 1, pp. 524-533.

Gasteiger et al, "Assessment of the Diversity of Combinatorial Libraries by an Encoding of Molecular Surface Properties," *Abstracts of Papers, American Chemical Society*, 211th ACS National Meeting, Item 070, Mar. 1996.

Hassan, Moises et al., "Optimization and visualization of molecular diversity of combinatorial libraries," *Molecular Diversity*, 1996, vol. 2, pp. 64-74.

de Ridder, D. and Duin, R.P.W., "Sammon's mapping using neural networks: A comparison," *Pattern Recognition Letters*, vol. 18, No. 11-13, 1997, pp. 1307-1316.

Kim, H. et al., "Self-Organized Distributed Networks for Learning Highly Nonlinear Mapping," *Intelligent Engineering Systems Through Artificial Neural Networks*, vol. 4, Nov. 13-16, 1994, pp. 109-114.

Pal, N.R. and Eluri, V.K., "Two Efficient Connectionist Schemes for Structure Preserving Dimensionality Reduction," *IEEE Transactions on Neural Networks*, vol. 9, No. 6, Nov. 1998, pp. 1142-1154.

Clark, R., et al., "Visualizing Substructural Fingerprints," *Journal of Molecular Graphics and Modelling*, vol. 18, Elsevier Science, Inc., New York, New York, Aug.-Oct. 2000, pp. 404-411.

Domine, D. et al., "Non-Linear Mapping for Structure-Activity and Structure-Property Modelling," *Journal of Chemometrics*, vol. 7, No. 4, John Wiley & Sons, Ltd., Jul.-Aug. 1993, pp. 227-242.

Lobanov, V.S. and Agrafiotis, D.K., "Stochastic Similarity Selections from Large Combinatorial Libraries," *J. Chem. Inf. Comput. Sci.*, vol. 40, No. 2, American Chemical Society, 2000 (published on Web Jan. 21, 2000), pp. 460-470.

* cited by examiner

ANTIARRHYTHMIC AGENT 1.4 M THROMBIN INHIBITOR

FIG. 13

| | SIZE OF RANDOM SELECTION | NUMBER OF TOP RANKED COMPOUNDS SELECTED | BEST SIMILARITY SCORE | NUMBER OF REAGENTS | SIZE OF FOCUSED LIBRARY | NUMBER OF MOST SIMILAR COMPOUNDS SELECTED | BEST SIMILARITY SCORE | AVERAGE SIMILARITY SCORE | PERCENT OF TOP 100 FOUND | TOTAL COMPOUNDS SCREENED | PERCENT OF THE LIBRARY SCREENED |
|---|---|---|---|---|---|---|---|---|---|---|---|
| DIAMINE LIBRARY | N/A | 100 | 0.7662 | 38 | N/A | 100 | 0.7662 | 1.30034 | 100 | 6750000 | 100 |
| 100K/10 | 100000 | 10 | 1.0207 | 20 | 300 | 100 | 0.8585 | 1.48825 | 37 | 300900 | 4 |
| 100K/50 | 100000 | 50 | 1.2266 | 70 | 12896 | 100 | 0.7662 | 1.31148 | 88 | 338688 | 5 |
| 100K/100 | 100000 | 100 | 1.0207 | 108 | 47487 | 100 | 0.7662 | 1.30306 | 96 | 442461 | 7 |
| 100K/200 | 100000 | 200 | 0.7662 | 167 | 170959 | 100 | 0.7662 | 1.30034 | 100 | 812877 | 12 |
| 1K/100 | 1000 | 100 | 2.1172 | 195 | 276623 | 100 | 0.7662 | 1.32782 | 88 | 832869 | 12 |
| 10K/100 | 10000 | 100 | 1.6919 | 151 | 126249 | 100 | 0.7662 | 1.30141 | 98 | 408747 | 6 |
| 100K/100 | 100000 | 100 | 1.0207 | 108 | 47487 | 100 | 0.7662 | 1.30306 | 96 | 442461 | 7 |
| 200K/100 | 200000 | 100 | 1.4557 | 96 | 33032 | 100 | 0.7662 | 1.30306 | 96 | 699096 | 10 |
| RANDOM 200K | 200000 | 100 | 1.1272 | N/A | N/A | 100 | 1.1272 | 1.82826 | 9 | 600000 | 9 |
| Ugi LIBRARY | N/A | 100 | 0.0000 | 37 | N/A | 100 | 0.0000 | 1.47494 | 100 | 6290000 | 100 |
| 100K/10 | 100000 | 10 | 0.7745 | 23 | 1153 | 100 | 0.7745 | 1.78473 | 46 | 303459 | 5 |
| 100K/50 | 100000 | 50 | 1.6871 | 76 | 96234 | 100 | 0.0000 | 1.47494 | 100 | 588702 | 9 |
| 100K/100 | 100000 | 100 | 1.4382 | 99 | 267251 | 100 | 0.0000 | 1.47737 | 98 | 1101753 | 18 |
| 100K/200 | 100000 | 200 | 1.1581 | 139 | 843712 | 100 | 0.0000 | 1.47737 | 98 | 2831136 | 45 |
| 1K/100 | 1000 | 100 | 2.5500 | 151 | 1300555 | 100 | 0.0000 | 1.47494 | 100 | 3904665 | 62 |
| 10K/100 | 10000 | 100 | 1.3793 | 121 | 583482 | 100 | 0.0000 | 1.48308 | 97 | 1780446 | 28 |
| 100K/100 | 100000 | 100 | 1.4382 | 99 | 267251 | 100 | 0.0000 | 1.47737 | 98 | 1101753 | 18 |
| 200K/100 | 200000 | 100 | 0.77448 | 96 | 222673 | 100 | 0.0000 | 1.47494 | 100 | 1268019 | 20 |
| 1K/50 | 1000 | 50 | 2.50076 | 102 | 331653 | 100 | 0.0000 | 1.52529 | 86 | 997959 | 16 |
| 10K/50 | 10000 | 50 | 1.22499 | 88 | 190661 | 100 | 0.0000 | 1.49912 | 92 | 601983 | 10 |
| 100K/50 | 100000 | 50 | 1.6871 | 76 | 96234 | 100 | 0.0000 | 1.47494 | 100 | 588702 | 9 |
| 200K/50 | 200000 | 50 | 1.1667 | 68 | 68089 | 100 | 0.0000 | 1.48086 | 98 | 804267 | 13 |
| RANDOM 400K | 400000 | 100 | 0.0000 | N/A | N/A | 100 | 0.0000 | 2.18251 | 17 | 1200000 | 19 |

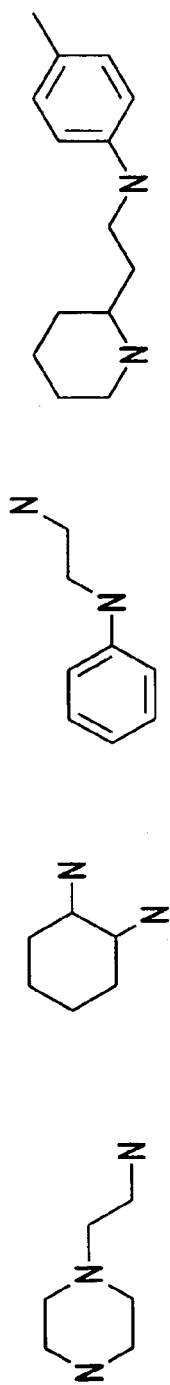
FIG.21A  EXAMPLE DIAMINES
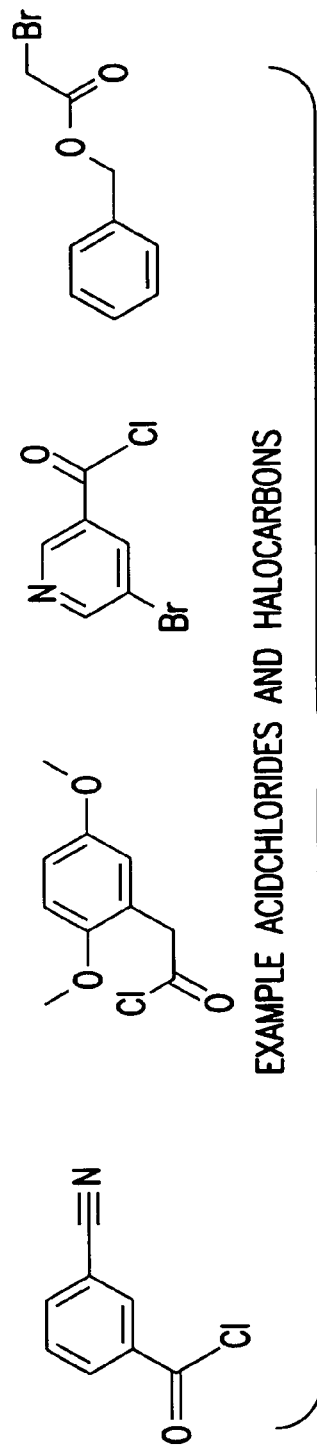
FIG.21B  EXAMPLE ACIDCHLORIDES AND HALOCARBONS

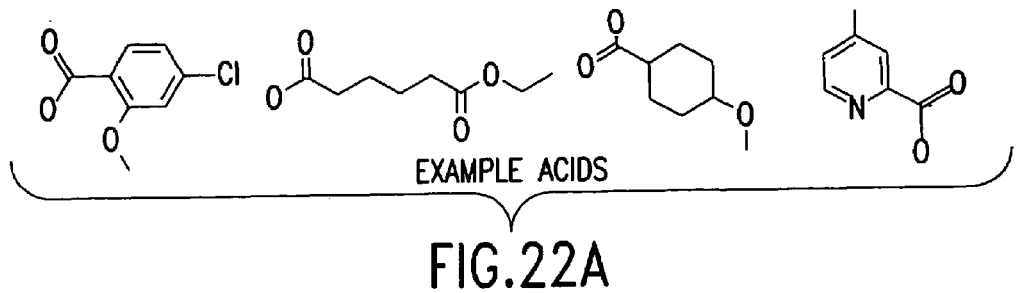
FIG.22A — EXAMPLE ACIDS
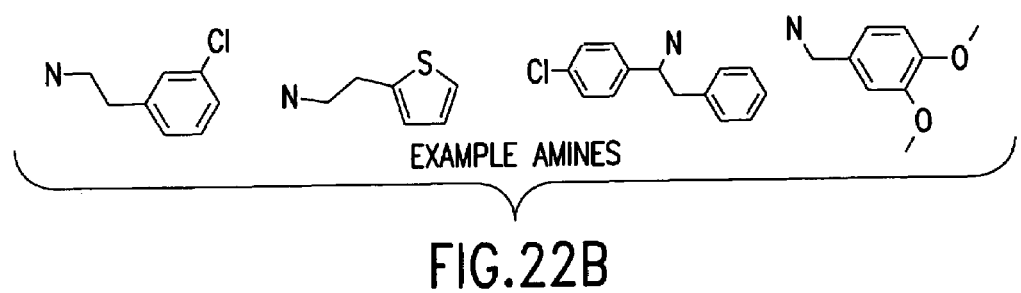
FIG.22B — EXAMPLE AMINES
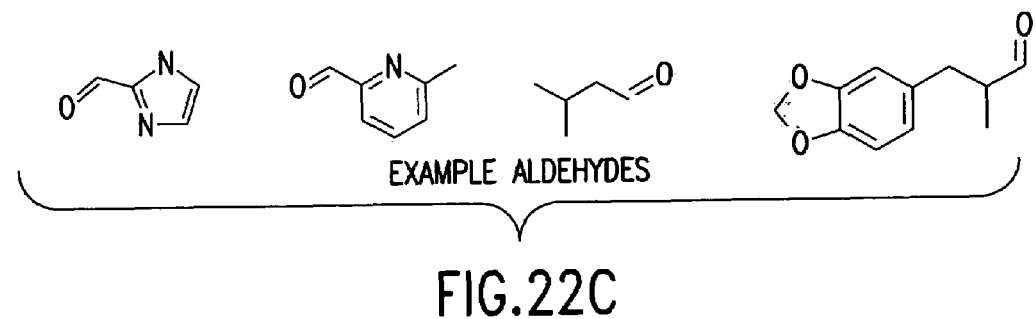
FIG.22C — EXAMPLE ALDEHYDES
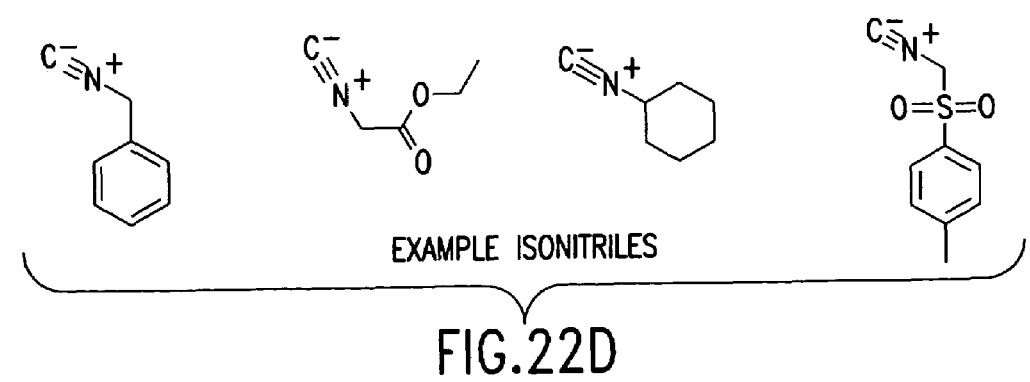
FIG.22D — EXAMPLE ISONITRILES

SYSTEM, METHOD AND COMPUTER PROGRAM PRODUCT FOR FAST AND EFFICIENT SEARCHING OF LARGE CHEMICAL LIBRARIES

BACKGROUND OF THE INVENTION

1. Field of the Invention

The present invention relates generally to searching of virtual combinatorial libraries. More particularly, the present invention relates to the selection of compounds, based on fitness functions, from large virtual combinatorial libraries.

2. Related Art

The explosive growth of combinatorial chemistry in recent years has been greeted as both a blessing and a curse. While it has solved the problem of throughput and has allowed the traditionally slow drug discovery process to be conducted in a massively parallelized fashion, it has created the need to deal with compound collections of truly staggering size. These include both physical collections of compounds that are synthesized using automated parallel synthesis, as well as virtual collections containing molecules that could potentially be synthesized by systematic application of established synthetic principles. The initial ambition to 'make and test them all' has given way to a more pragmatic approach once it became evident that 'all' was a number of immense proportions. For example, a simple diamine-based combinatorial library built from only commercially available reagents can include up to $10^{12}$ compounds which is equivalent to approximately 300 years of synthesis and testing at a rate of 10 million compounds per day (Cramer et al., "Virtual Compound Libraries: A New Approach to Decision Making in Molecular Discovery Research," J. Chem. Inf. Comput. Sci. 1998, 38, 1010-1023). The recognition of these practical limitations and the desire to use the available synthetic and screening resources in an efficient way has generated interest in virtual chemistry and, in particular, systems and methods for handling and analyzing large chemical libraries. More specifically, for example, there is an interest in efficiently selecting compounds that are similar to a particular query structure (e.g., drug lead) or selecting compounds that have desired properties.

Searching a virtual combinatorial library for compounds that are similar to a particular query structure (or query structures) or have a set of desired properties typically involves three steps for each compound: enumeration, calculation of descriptors, and evaluation of similarity or estimation of the property of interest. Due to the large number of possible products in many virtual combinatorial libraries (particularly three- and four-component ones), just the enumeration part alone can take a few weeks of computational time. Additionally, the storage requirements for a fully enumerated virtual combinatorial library can be prohibitive. Since in these cases neither the generation nor the storage of fully enumerated libraries and their associated descriptors is feasible, there is a need for systems and methods that can identify the desired compounds without enumerating the entire library.

One possible solution is to look at the far less numerous reagents instead of the products. The reagent-based approach is frequently used to maximize molecular diversity, and is based on the assumption that diverse reagents will lead to diverse products. However, it was recently shown that a selection based on the products themselves can be substantially more diverse, perhaps by as much as 35-50% (Gillet et al., "The Effectiveness of Reactant Pools for Generating Structurally-Diverse Combinatorial Libraries," J. Chem. Inf. Comput. Sci. 1997, 37, 731-740). When the selection criterion is similarity, the final products themselves must be considered, and the only proposed solution has been to use additive or otherwise "decomposable" descriptors. These are descriptors which, for combinatorial products, can be computed from the values of the corresponding descriptors of their constituent reagents (Cramer et al., "Virtual Compound Libraries: A New Approach to Decision Making in Molecular Discovery Research," J. Chem. Inf. Comput. Sci. 1998, 38, 1010-1023).

Thus, the need remains for a system and method for efficiently and effectively generating product-based selections from large virtual combinatorial libraries. More generally, there is a need for a system and method for efficiently and effectively searching large virtual combinatorial libraries based on a fitness function.

There do exist some virtual combinatorial libraries that have already been fully or partially enumerated. However, there is currently a deficiency of satisfactory systems and methods for efficiently and effectively searching these enumerated virtual combinatorial libraries based on a fitness function. Accordingly, there is also a need for a system and method for efficiently and effectively searching large enumerated virtual combinatorial libraries based on a fitness function.

SUMMARY OF THE INVENTION

The present invention is a system, method, and computer program product for searching of large virtual combinatorial libraries based on a fitness function. Conventional systems and methods for searching virtual combinatorial libraries typically enumerate and characterize every reagent combination (i.e., possible compound) associated with the virtual combinatorial library, characterize every enumerated compound, and then perform an evaluation, based on a fitness function, for every compound. Selecting compounds from a large virtual combinatorial library using such conventional systems and methods requires prohibitively excessive amounts of time and resources. The present invention reduces the amount of time and resources that are necessary to search a large virtual combinatorial library by not requiring the enumeration, characterization, and evaluation of every reagent combination associated with the library.

According to the method of an embodiment of the present invention, a first set of N reagent combinations are selected from a virtual combinatorial library. The selection can be random or non-random. Each reagent combination in the first set is then enumerated to produce a first set of enumerated compounds. M number of compounds of the first set of enumerated compounds are selected based on a fitness function. The M compounds are then deconvoluted into reagents to generate a focused library. Every reagent combination associated with the focused library is enumerated to produce a second set of enumerated compounds. K number of compounds of the second set of enumerated compounds are then selected based on the fitness function. These K compounds represent a near optimal selection of compounds based on the fitness function.

Examples of fitness functions that can be used with the present invention include, but are not limited to, similarity to one or more query structures, diversity, and presence of desired properties. That is, for example, the present invention can be used to efficiently and effectively select, from a large virtual combinatorial library, a set of the near optimal most similar compounds to a drug lead. The present invention can also be used to efficiently and effectively select a diverse collection of compounds from a large virtual combinatorial library. Additionally, the present invention can be used to select compounds having desired properties from a large virtual combinatorial library.

In an alternative embodiment, the present invention can be used to search large enumerated virtual combinatorial libraries. This embodiment of the present invention takes advantage of those virtual combinatorial libraries that have already been enumerated.

Features and advantages of the present invention, as well as the structure and operation of various embodiment of the present invention, are described in detail below with reference to the accompanying drawings. In the drawings, like reference numbers indicate identical or functionally similar elements. Also, the leftmost digit(s) of the reference numbers identify the drawings in which the associated elements are first introduced.

BRIEF DESCRIPTION OF THE FIGURES

The present invention will be described with reference to the accompanying drawings, wherein:

FIG. 13 is a table that summarizes the experimental results obtained when using an embodiment of the present invention;

FIG. 21 shows examples of diamines, and acidchlorides and halocarbons (i.e., alkylating/acylating agents), associated with the diamine virtual combinatorial library that was used to demonstrate the effectiveness of the present invention; and FIG. 22 shows examples of acids, amines, aldehydes, and isonitriles, associated with the Ugi virtual combinatorial library that was used to demonstrate the effectiveness of the present invention.

DETAILED DESCRIPTION OF THE PREFERRED EMBODIMENTS

Table of Contents

1. General Overview

Figure 1:
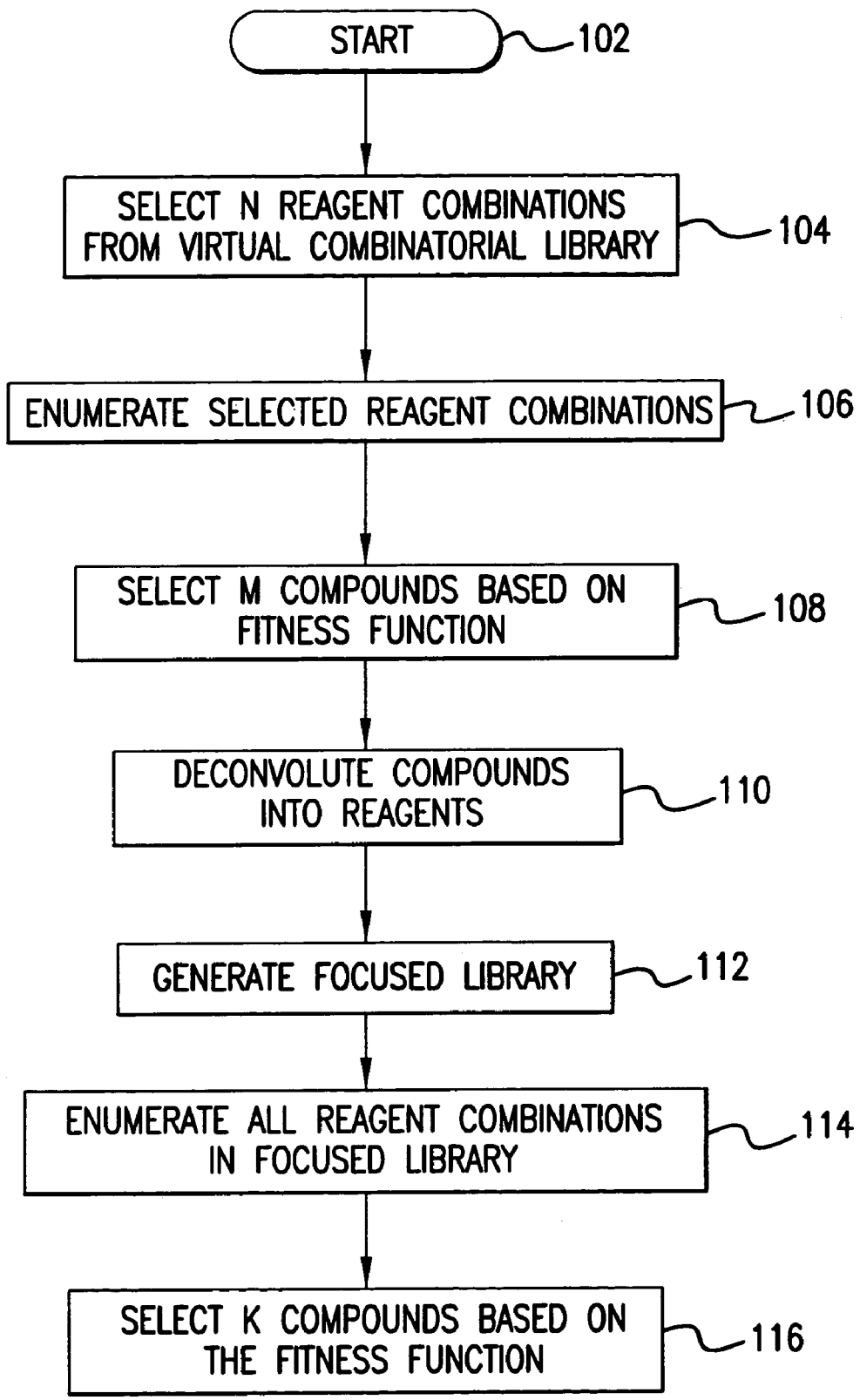
FIG. 1 is a process flowchart illustrating a method for searching of virtual combinatorial libraries, according to an embodiment of the present invention.

2. Exemplary Embodiments
   a. K Most Similar Compounds to a Query Structure
   b. Array (Sub-Matrix) of Most Similar Compounds
   c. K Most Diverse Compounds
   d. Array (Sub-Matrix) of Most Diverse Compounds 3. Experimental Results and Discussion 4. Example Environment 5. Structure of Present Invention

1. General Overview

The present invention is directed to a system, method, and computer program product for searching large virtual combinatorial libraries based on fitness functions. In one embodiment, the fitness function is similarity to one or more query structures (i.e., probe(s)). In this embodiment, the present invention can be used to significantly reduce the amount of time and resources that it takes to search a large virtual combinatorial library for a set of compounds that are similar to a query structure(s) (e.g., a drug lead). In another embodiment, the fitness function is related to diversity of a collection of compounds. In the diversity embodiment, the present invention can be used to significantly reduce the amount of time and resources that it takes to search a large virtual combinatorial library for a collection of diverse compounds.

The fitness function can also be related to a desired characteristic. That is, the present invention can be used to significantly reduce the amount of time and resources that it takes to search a large virtual combinatorial library for compounds that exhibit (or do not exhibit) specific characteristics. Such characteristics can include, for example, physical properties, chemical properties, functional properties and/or bioactive properties, although the invention is not limited to these characteristics.

According to one specific embodiment, the present invention is directed to a system, method, and computer program product for generating product-based similarity selections from large virtual combinatorial libraries. An advantage of this embodiment of the present invention, as compared to conventional similarity searching techniques, is that the present invention does not require enumeration and descriptor generation for every reagent combination associated with a virtual combinatorial library. This results in a significant reduction in the resources necessary to carry out similarity selections. Additional advantages of this embodiment of the present invention is that it is not limited to additive or "decomposable" descriptors. Further, this embodiment of the present invention is able to provide an optimal or nearly optimal similarity selection in a reasonable time frame. For illustrative purposes only, this embodiment will be described in the most detail. However, the intention is not to limit the present invention to use in similarity searching. Rather, the intention is to provide sufficient detail so that one skilled in the art can use the present invention with various fitness functions. Alternative fitness functions include, but are not limited to, diversity and presence of one or more desired properties.

Conventional systems used for similarity selection enumerate and characterize each reagent combination (i.e., possible compound) associated with a virtual combinatorial library, characterize every enumerated compound using descriptors, and then perform a similarity evaluation for every possible compound. Performing similarity selection using such conventional systems is extremely time inefficient. For example, the enumeration, characterization, and similarity evaluation of a virtual combinatorial library containing 6.75 million possible compounds (i.e., reagent combinations) required 34 hours on a dual processor 400 MHz Intel Pentium II machine.

In contrast, using the present invention, a similarity evaluation of the same 6.75 million possible compounds, using the same dual processor 400 MHZ Intel Pentium II machine, required only 30 minutes. This large reduction in time is due to the fact that the present invention does not perform enumeration, characterization, and similarity evaluation for all of the 6.75 million possible compounds.

The present invention is also directed to a system, method, and computer program product for searching large enumerated virtual combinatorial libraries based on fitness functions. This embodiment of the present invention takes advantage of those virtual combinatorial libraries that have already been enumerated.

The concepts of virtual libraries, virtual combinatorial libraries, molecular similarity, enumeration, and the selection problem associated with virtual combinatorial libraries are of particular pertinence to the present invention. Accordingly, each of these concepts are discussed in some detail below.

Virtual Library. A virtual library is essentially a computer representation of a collection of chemical compounds obtained through actual and/or virtual synthesis, acquisition, or retrieval. By representing chemicals in this manner, one can apply cost-effective computational techniques to identify compounds with desired physico-chemical properties, or compounds that are diverse, or similar to a given query structure. By trimming the number of compounds being considered for physical synthesis and biological evaluation, computational screening can result in significant savings in both time and resources, and is now routinely employed in many pharmaceutical companies for lead discovery and optimization.

Virtual Combinatorial Libraries. Whereas a compound library generally refers to any collection of actual and/or virtual compounds assembled for a particular purpose (for example a chemical inventory or a natural product collection), a virtual combinatorial library represents a collection of compounds derived from the systematic application of a synthetic principle on a prescribed set of building blocks (i.e., reagents). These building blocks are grouped into lists of reagents that react in a similar fashion (e.g. A reagents and B reagents) to produce the final products constituting the library (C, $A_i+B_j \rightarrow C_{ij}$). Full virtual combinatorial libraries encompass the products of every possible combination of the prescribed reagents, whereas sparse combinatorial libraries (also called sparse arrays) include systematic subsets of products derived by combining each $A_i$ with a different subset of $B_j$'s. Unless mentioned otherwise, the term virtual combinatorial library will hereafter imply a full virtual combinatorial library.

A virtual combinatorial library can be thought of as a matrix with reagents along each axis of the matrix. For example, the chemical reaction $A_i+B_j \rightarrow C_{ij}$, may be represented by a two dimensional matrix with the A reagents along one axis and the B reagent along another axis. If there exist 10 different A reagents and 10 different B reagents, then a virtual combinatorial library representing this chemical reaction would be a 10×10 matrix, with 100 possible products (also referred to as possible compounds or reagent combinations). If the chemical reaction to be represented by a virtual library were $A_i+B_j+C_k \rightarrow D_{ijk}$, and reagent class A included 1,000 reagents, reagent class B included 10,000 reagents, and reagent class C included 500 reagents, then a virtual combinatorial library representing this chemical reaction would be a 1,000×10,000×500 matrix (i.e., a three dimensional matrix), with $5 \times 10^9$ possible products (i.e., $D_{ijk}$s).

The possible products that are represented by cells of the virtual combinatorial library matrix need not be explicitly represented. That is, the possible products in each cell of the matrix need not be enumerated. Rather, the possible products in each cell can simply be thought of as Cartesian coordinates corresponding to a particular reagent combination, such as $A_1B_5$. Unless mentioned otherwise, a virtual combinatorial library should be thought of as a matrix representing a chemical reaction where the products have not been enumerated. Explained another way, a virtual combinatorial library can be thought of as a matrix having a defined size but with empty cells. Each empty cell can be labeled as a reagent combination (e.g., $A_1B_5$). In contrast, a fully enumerated virtual combinatorial library can be thought of as a matrix having an enumerated compound in each cell. Unless specifically referred to as an enumerated virtual combinatorial library, mention of a virtual combinatorial library refers to a non-enumerated virtual combinatorial library.

Enumeration. Enumeration is the process of constructing computer representations of a structure of one or more products associated with a virtual combinatorial library. Enumeration is accomplished by starting with reagents and performing chemical transformations, such as making bonds and removing one or more atoms, to construct explicit product structures. In the general sense, enumeration of an entire virtual combinatorial library means explicitly generating representations of product structures for every possible product of the virtual combinatorial library.

A computer system may require inordinate amounts of time and resources to enumerate every reagent combination associated with a large virtual combinatorial library. Further, the disk requirements for storing every enumerated product (i.e., product structure) can be excessive. Accordingly, a feature of the present invention is to reduce the amount of products that are enumerated during searching of a large virtual combinatorial library.

Virtual Combinatorial Library Generation. Once a synthetic protocol is designed, a virtual combinatorial library can be created. In addition to providing the basis for computational screening, these libraries are also convenient for tracking and archiving purposes. The conceptual approach to generating virtual combinatorial libraries is straightforward. The reaction transformations that convert the reagents into products (i.e., compounds) is reduced into a set of substructure patterns which are mapped onto the reagents to identify reacting groups or atoms, and a list of instructions of how to modify the chemical graphs. These instructions include actions such as removing an existing atom or bond, inserting a new bond between two atoms, or changing the order of a bond. For more complex reactions, the modifications may also include changing the formal charge or chirality of an atom. Complications arise from the fact that the substructure patterns have to be correctly defined so that they map only to those parts of a molecule that would indeed react under the prescribed conditions. For example, if one of the reagents is an amine, it can be defined as a nitrogen atom connected to a carbon and to at least one hydrogen atom (to account for both primary and secondary amines). However, such a definition would also include amides, which are chemically different from amines. Hence, the definition of the amine pattern has to be extended to include further neighboring atoms. Alternatively, substructures which should be avoided can be introduced into the instructions. Furthermore, if primary amines are more reactive than secondary amines, primary and secondary amines should be mapped separately and assigned different priorities. Additional issues that need to be addressed are removal of protecting or leaving groups (which may or may not be present), and handling of multiple possible products due to regio- or stereo-isomerism or the presence of multiple reactive functionalities within the same reagent.

By their very nature, virtual combinatorial libraries can reach extremely large sizes even with a relatively modest number of building blocks, particularly if there is a large number of variation sites (a problem known as combinatorial explosion). For example, if enumerated, the above-mentioned diamine library can easily include $10^{12}$ reagent combinations. Were it to be enumerated, this library would contain 50,000 times more compounds than the world's cumulative chemical literature, and would require 10 terabytes of storage space at 100 bytes per structure. Finally, the enumeration of the entire library at a rate of 100,000 structures per second would take over three months. Accordingly, as stated by R. D. Cramer et al. in their article, "Virtual Compound Libraries: A New Approach to Decision Making in Molecular Discovery Research," J. Chem. Inf. Comput. Sci. 1998, 38, pages 1010-1023, when dealing with virtual combinatorial libraries of this size explicit enumeration is not an option.

Generally, a universally applicable program has been developed for generating virtual libraries. As input, this program takes lists of reagents supplied in Structure-Data File (SDF) format, developed by MDL Information Systems Inc., San Leandro, Calif., or Simplified Molecular Input Line Entry Specification (SMILES) format, introduced by Daylight Chemical Information System, Inc., Los Altos, Calif. Reaction definitions can be written in an extension of a scripting language, such as Tool Command Language (Tcl). The use of a scripting language provides a powerful, human-readable, and convenient way of encoding chemical reactions. All chemically feasible transformations are supported, including multiple reactive functionalities, different stoichiometries, cleavage of protecting groups, and many others. The library is stored in a compact format without an explicit enumeration of the products. The computational requirements of the algorithm are minimal (even a billion-membered library can be generated in a few CPU seconds on a personal computer) and are determined not by the size of the library but by the number of reagents. Despite the implicit encoding, individual structures can be accessed at a rate of 1,000,000 per CPU second.

Use of Virtual Combinatorial Libraries. The role of virtual combinatorial libraries in drug discovery is to provide computational access to compounds that can be readily synthesized and tested for biological activity. The role of the computational tools is to identify which compounds from the library need to be tested to achieve the desired objective. For example, in lead discovery, the objective is to explore different structural classes in order to identify "activity islands" in structure-activity space. Hence, the selected compounds have to be dissimilar from one another so that each compound provides unique and non-redundant information on the structure activity relationship (SAR) landscape. Selecting compounds based on their dissimilarity or diversity has become very popular in recent years, and there has been an extensive number of publications which address this subject. Examples of such publications include: Agrafiotis, "On the Use of Information Theory for Assessing Molecular Diversity," J. Chem. Inf. Comput. Sci. 1997, 37, 576-580; Agrafiotis, "Stochastic Algorithms for Maximizing Molecular Diversity," J. Chem. Inf. Comput. Sci. 1997, 37, 841-851; Agrafiotis, "Diversity of Chemical Libraries," in Encyclopedia of Computational Chemistry, 1998; Clark, "OptiSim: An Extended Dissimilarity Selection Method for Finding Diverse Representative Subsets," J. Chem. Inf. Comput. Sci. 1997, 37, 1181-1188; Gillet et al., "The Effectiveness of Reactant Pools for Generating Structurally-Diverse Combinatorial Libraries," J. Chem. Inf. Comput. Sci. 1997, 37, 731-740; Gillet et al., "Selecting Combinatorial Libraries to Optimize Diversity and Physical Properties," J. Chem. Inf. Comput. Sci. 1999, 39, 169-177; and Martin et al., "Beyond Mere Diversity: Tailoring Combinatorial Libraries for Drug Discovery," J. Comb. Chem. 1999, 1, 32-45.

Once one or more initial leads have been identified (that is, compounds that show activity against a target and are structurally novel), emphasis is shifted towards exploring more extensively the structure-activity space around those one or more lead molecules. Typically, this is accomplished by selecting and screening compounds that are similar to the initial lead(s). Finally, the accumulated qualitative, and if available quantitative, SAR information is used to optimize the initial leads into preclinical candidates through conventional medicinal chemistry techniques.

Besides similarity and diversity (i.e., dissimilarity), other selection criteria can also be employed. Examples include selecting compounds having desired properties or property distributions as determined by a property prediction algorithm or a quantitative structure-activity model, or exhibiting an optimal fit to a biological receptor as determined by a biomolecular docking algorithm. Compound can also be selected based on 2 D and 3 D QSAR predictions, and receptor complementarity. Additional details of these and other selection criteria are described in the following patents and patent application, each of which is incorporated herein by reference in its entirety: U.S. Pat. No. 5,463,564, entitled "System and Method of Automatically Generating Chemical Compounds with Desired Properties"; U.S. Pat. No. 5,574, 656 entitled "System and Method of Automatically Generating Chemical Compounds with Desired Properties"; U.S. Pat. No. 5,684,711, entitled, "System, Method, and Computer Program for at Least Partially Automatically Generating Chemical Compounds Having Desired Properties"; U.S. Pat. No. 5,901,069, entitled "System, Method, and Computer Program Product for at Least Partially Automatically Generating Chemical Compounds with Desired Properties from a List of Potential Chemical Compounds to Synthesize"; and U.S. patent application Ser. No. 08/963,870 now U.S. Pat. No. 6,421,612, entitled "System, Method and Computer Program Product For Identifying Chemical Compounds Having Desired Properties."

Molecular Similarity. Similarity is one of the most subjective concepts in chemistry, and can be defined in a multitude of ways. Depending on one's objectives, available tools, and other factors, compounds can be considered similar if they have similar numbers of atoms of the same types (constitutional similarity), similar numbers of bonds and rings of the same types and similar degree of branching (topological similarity), similar shape and surface characteristics (shape similarity) or similar electron density distribution (electrostatic similarity). Alternatively, similarity can be determined based on the presence or absence of certain features such as a common substructure (substructural similarity), the relative position and orientation of important pharmacophoric groups (pharmacophore similarity), binding affinity as predicted by a receptor binding model (receptor affinity similarity), the degree of conformational overlap with a known receptor binder (conformational similarity), etc.

The precise numerical value used to describe the similarity between two compounds depends on the representation of these compounds, the weighting scheme used to scale different aspects of the representation, and the similarity coefficient used to compare these representations (Willett et al. "Chemical Similarity Searching," J. Chem. Inf. Comput. Sci. 1998, 38, 983-996). Often, individual compounds are represented by a bit-string, such as a substructure key or a hashed fingerprint, where each bit or group of bits indicates the presence or absence of a particular structural feature. Alternatively, compounds can be represented by a vector of real numbers, each of which corresponds to a particular molecular descriptor. It has been suggested that in all cases the representation of the structures must comply with the "neighborhood principle" if it is to be useful in identifying biologically active molecules (Cramer, et al. "Virtual Compound Libraries: A New Approach to Decision Making in Molecular Discovery Research," J. Chem. Inf. Comput. Sci. 1998, 38, 1010-1023). The neighborhood principle states that molecules with similar representations (i.e. molecules located within the same local region or "neighborhood" of the feature space) should have similar values of the physical property of interest. Recently, the neighborhood behavior of 11 sets of 2 D and 3 D molecular descriptors was analyzed following a validation study on the ability of these descriptors to cluster active compounds (Patterson et al. "Neighborhood Behavior: A Useful Concept for Validation of Molecular Diversity Descriptors," J. Med. Chem. 1996, 39, 3049-3059; Brown et al. "Designing Combinatorial Library Mixtures Using a Genetic Algorithm," J. Med. Chem. 1997, 40, 2304-2313). Descriptors which were found to exhibit "proper neighborhood behavior" included 2 D fingerprints, topomeric fields, and atom pairs. Finally, the degree of structural similarity between two compounds is quantified by means of a similarity coefficient, such as Tanimoto coefficient for binary sets, and the Euclidean distance for real vectors. A thorough review of molecular similarity measures can be found in Willett et al. "Chemical Similarity Searching," J. Chem. Inf. Comput. Sci. 1998, 38, 983-996, which is incorporated herein by reference in its entirety.

The specific details of the present invention are described in detail below, in relation to exemplary embodiments.

2. Exemplary Embodiments

As discussed above, the present invention is directed to the searching of large virtual combinatorial libraries based on a fitness function, such as similarity to a query structure. A preferred method for fast searching of large combinatorial libraries, according to the present invention, is described with reference to FIG. 1.

First, in step 104, a sufficiently large sample N (e.g., N=100,000) of potential compounds (i.e., reagent combinations) is selected from a virtual combinatorial library. The selected sample is also referred to as the first set of reagent combinations. In a preferred embodiment, the set of N reagent combinations are selected at random. In such an embodiment, the sample is also referred to as the random set, the original random set, and the random seed. In another embodiment, the first set of reagent combinations is selected such that a uniform coverage of reagent space is selected. Any known algorithm for selecting a random or approximately random set can be employed. In still another embodiment, the first set of reagent combinations is selected such the each reagent in the virtual combinatorial library is selected exactly a predefined (e.g., X) number of times or a substantially equal number of times. Of course other methods of selecting N reagent combinations are within the spirit and scope of the present invention, including random and non-random methods.

The selection of a random sample can be better explained using the following example. Assume a random sample of 100,000 possible reagent combinations (i.e., N=100,000) are to be selected from a virtual combinatorial library that represents the chemical reaction $A_i+B_j+C_k \rightarrow D_{ijk}$, where reagent class A includes 1,000 reagents, reagent class B includes 10,000 reagents, and reagent class C includes 5,000 reagents. The virtual combinatorial library representing this chemical reaction can be thought of as a 1,000×10,000×500 matrix (i.e., a three dimensional matrix), with $5 \times 10^9$ possible products (i.e., reagent combinations). More specifically, along the X axis of the matrix is $A_1$ to $A_{1000}$, along the Y axis of the matrix is $B_1$ to $B_{1000}$, and along the Z axis of the matrix is $C_1$ to $C_{500}$. One method of selecting 100,000 possible combinations of reagents from this virtual combinatorial library is by generating 100,000 random numbers from 1 to 1000, 100,000 random numbers from 1 to 10,000, and 100,000 random numbers from 1 to 500, and using these randomly selected numbers to generate 100,000 possible combinations of $A_i$, $B_j$ and $C_k$. Examples of possible combinations of $A_i$, $B_j$ and $C_k$ include: $A_{322}B_{1902}C_{401}$ (i.e., $A_{i=322}B_{j=1902}C_{k=401}$), $A_{332}B_{205}C_5$, $A_{105}B_{9333}C_{304}$ and $A_{46}B_{9502}C_{208}$. Each of these 100,000 possible combinations of $A_i$, $B_j$ and $C_k$ can be thought of representing Cartesian coordinates (i.e., empty cells of the matrix) corresponding to a particular combination of reagents. Of course, other methods of selecting a set are within the spirit and scope of the present invention.

Selection of an appropriate value N is implementation specific. As discussed in the Experimental Results section below, good results have been obtained when the value chosen for N is approximately 0.1% of the total number R of reagent combinations associated with the virtual combinatorial library.

Next, in step 106, each reagent combination in the first set of compounds is enumerated to produce a first set of enumerated compounds. Thus, if 100,000 reagent combination (e.g., N=100,000) were selected in step 104, then the first set of enumerated compounds will include 100,000 enumerated compounds.

Next, in step 108, M compounds (e.g., M=100) are selected, based on a fitness function, from the first set of enumerated compounds.

Selection of an appropriate value M is implementation specific. As discussed in the Experimental Results section below, good results have been obtained when the value chosen for M is approximately 0.1% of the value N.

Once M compounds are selected, based on the fitness function, from the first set of enumerated compounds, these M compounds are then deconvoluted into their building blocks (i.e., reagents), in step 110.

In step 112, the building blocks resulting from step 110 are combined into lists of "preferred" reagents and are used to produce a smaller "focused" library. This "focused" library can be thought of as a sub-matrix of the larger matrix that represents the entire original virtual combinatorial library.

Substantially all of the potential compounds in the "focused" library (i.e., the second set of compounds) are then enumerated in step 114 to produce a second set of enumerated compounds. Since the focused library is significantly smaller than the original virtual combinatorial library, the amount of time and resources required to enumerate the entire focused library is significantly less than required to enumerate the entire original virtual combinatorial library.

Finally, in step 116, K compounds (e.g., K=100) are selected, based on the fitness function, from the second set of enumerated compounds. These K compounds represent near optimal set of compounds that best satisfy the fitness function. The selection of an appropriate value K is also implementation specific.

Because of its stochastic nature, the best results are obtained by repeating the above described method more than one time and combining the results. The inventors have found that repeating the above method (i.e., steps 104-116) three separate times and combining the results produces excellent results, as explained below, although the invention is not limited to this example.

The preferred method for fast searching of a large combinatorial library described above in the discussion of FIG. 1 can be further explained with reference to FIGS. 2, 3 and 4.

Figure 2:
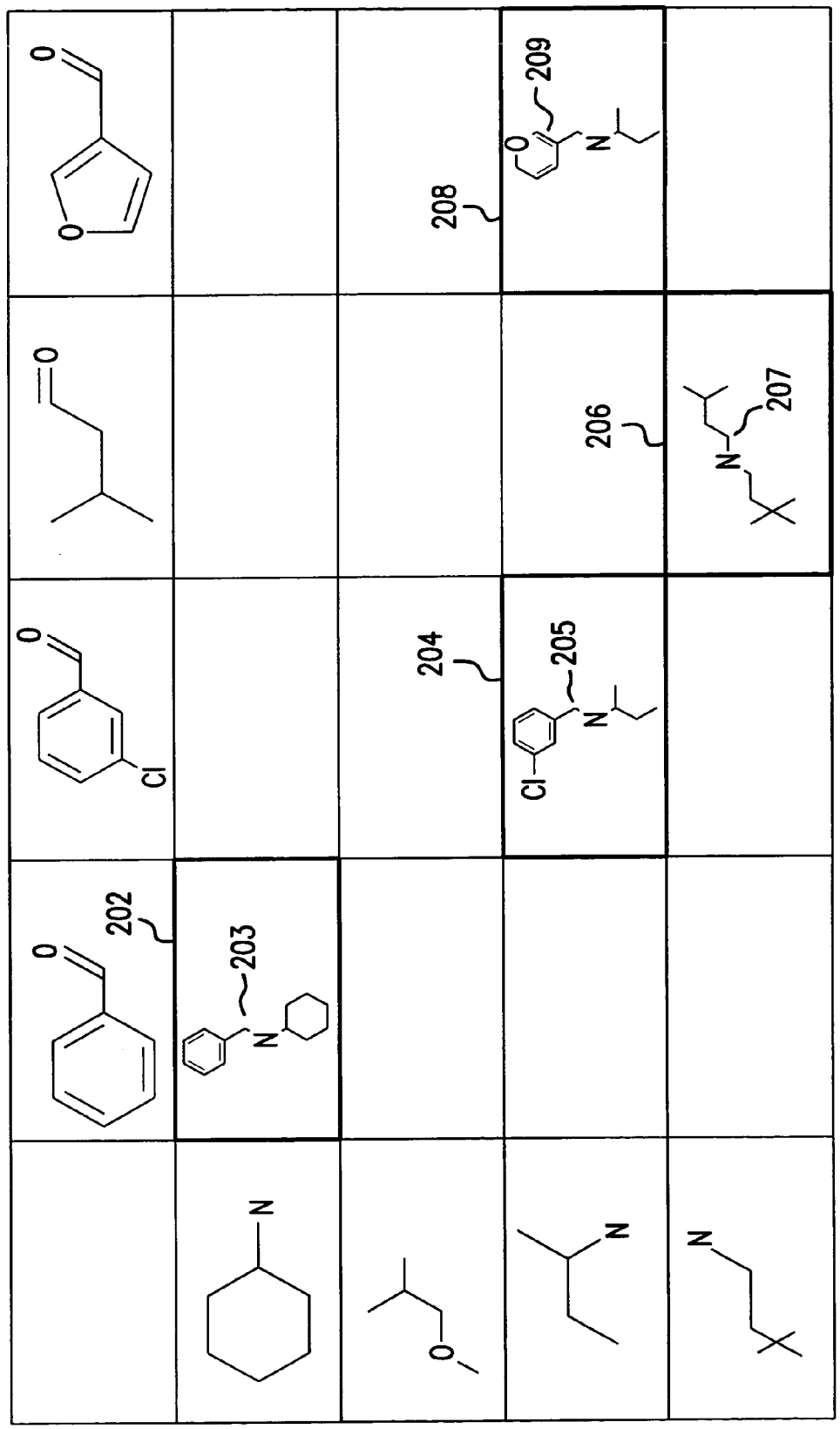
FIGS. 2 and 3 show a matrix that represents a small portion of a large virtual combinatorial library.
Figure 3:
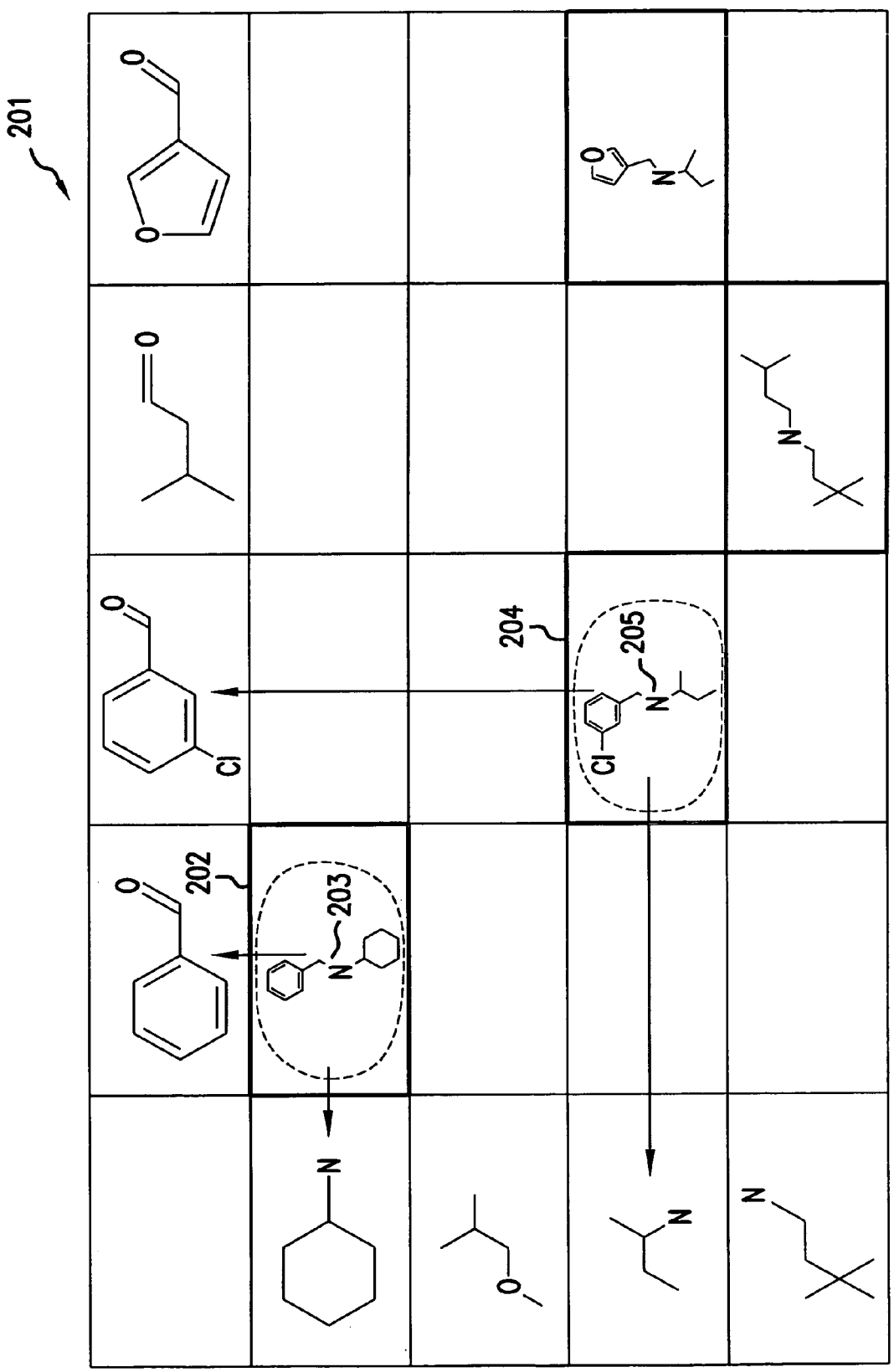

FIG. 2 shows a 4×4 matrix 201 of reagents that represents a small portion of a large virtual combinatorial library associated with the chemical reaction $A_i+B_j \rightarrow C_{ij}$. If the entire virtual combinatorial library were enumerated, then each of the 16 cells shown in the 4×4 matrix 201 would include an enumerated compound (i.e., a computer representation of the structure of a compound). As discussed above, a computer system may require an inordinate amount of time and resources to enumerate every potential reagent combination associated with a large virtual combinatorial library. Accordingly, in the present invention, a sample N of potential compounds (i.e., reagent combinations) is selected (e.g., at random) from the virtual combinatorial library (Step 104). In FIG. 2, the four cells, 202, 204, 206, and 208, that have thick borders represent the selected reagent combinations. As shown in FIG. 2, only those selected reagent combinations are enumerated (Step 106) to produce a first set of enumerated compounds which includes compounds 203, 205, 207, and 209. Next, M compounds are selected, based on the fitness function, from the first set of enumerated compounds (Step 108). For this example, it is assumed that enumerated compounds 203 and 205 are included in the M selected compounds.

Once M compounds are selected, based on the fitness function, from the first set of enumerated compounds, these M compounds are then deconvoluted into their building blocks (i.e., reagents) (Step 110). This is represented by the arrows in FIG. 3.

Figure 4:
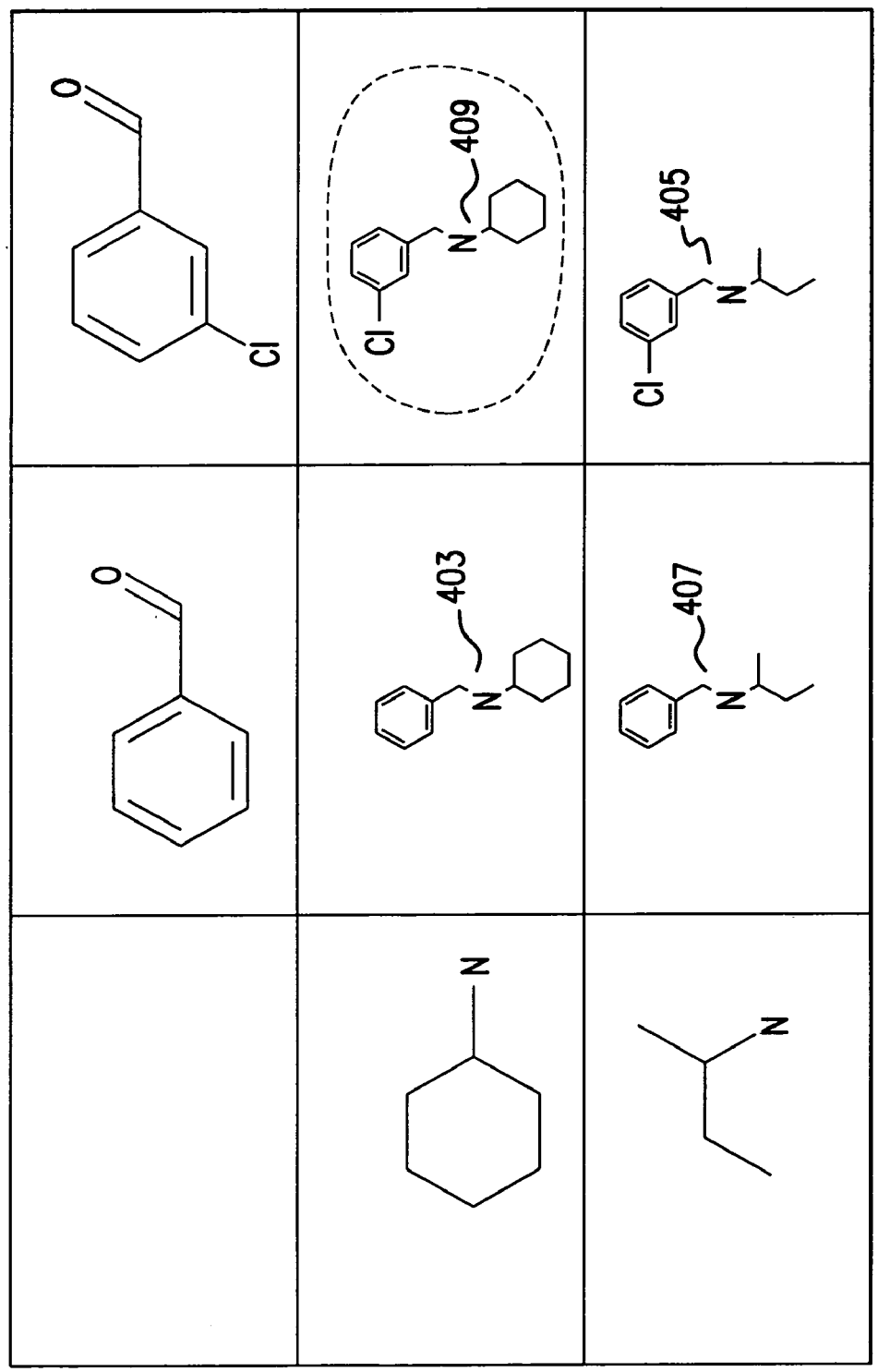
FIG. 4 shows a matrix that represents a small portion of a focused library that is generated using the present invention.

The building blocks are then combined into lists of "preferred" reagents that are used to produce a smaller "focused" library, which includes 2×2 matrix 401 (Step 112), as shown in FIG. 4. All the compounds in the "focused" library are enumerated to produce a second set of enumerated compounds (Step 114), which includes compounds 403, 407, 409, and 405.

Finally, K compounds are selected, based on the fitness function, from the second set of enumerated compounds (Step 116). For this example, it is assumed that only enumerated compound 409 is included in the K selected compounds.

Another embodiment of the present invention takes advantage of those virtual libraries that have already gone through the timely process of being enumerated. More specifically, in an alternative embodiment, the present invention is directed to the searching of fully (or partially) enumerated combinatorial libraries based on a fitness function, such as similarity to one or more query structures. This method for fast searching of enumerated combinatorial libraries, according to this alternative embodiment of the present invention, is described with reference to FIG. 1A.

First, in step 104a, a sufficiently large sample N (e.g., N=100,000) of enumerated compounds is selected from an enumerated virtual combinatorial library. The selected sample is also referred to as the first set of enumerated compounds. In one embodiment, the set of N enumerated compounds are selected at random. In another embodiment, the first set of N enumerated compounds is selected such that a uniform coverage of reagent space is selected. Any known algorithm for selecting a random or approximately random set can be employed. In still another embodiment, the first set of enumerated compounds is selected such the each reagent in the virtual combinatorial library is selected exactly a predefined (e.g., X) number of times or a substantially equal number of times. Of course other methods of selecting N enumerated compounds are within the spirit and scope of the present invention, including random and non-random methods.

The selection of a random set of enumerated compounds can be better illustrated using the following example. Assume a random selection of 100,000 enumerated compounds (i.e., N=100,000) are to be selected from an enumerated virtual combinatorial library that represents the chemical reaction $A_i+B_j+C_k \rightarrow D_{ijk}$, where reagent class A includes 1,000 reagents, reagent class B includes 10,000 reagents, and reagent class C includes 5,000 reagents. The enumerated virtual combinatorial library representing this chemical reaction can be thought of as a 1,000×10,000×500 matrix (i.e., a three dimensional matrix), with $5 \times 10^9$ enumerated compounds within in the cells of the matrix. More specifically, along the X axis of the matrix is $A_1$ to $A_{1000}$, along the Y axis of the matrix is $B_1$ to $B_{10,000}$, along the Z axis of the matrix is $C_1$ to $C_{500}$, and within the cells are enumerated compounds. One method of selecting 100,000 enumerated compounds from this enumerated virtual combinatorial library is by generating 100,000 random numbers from 1 to 1000, 100,000 random numbers from 1 to 10,000, and 100,000 random numbers from 1 to 500, and using these randomly selected numbers to select 100,000 enumerated compounds. Each of these 100,000 possible combinations of $A_i$, $B_j$ and $C_k$ can be thought of representing cells of the matrix that include the corresponding enumerated compound. Of course, other methods of selecting a set are within the spirit and scope of the present invention.

Selection of an appropriate value N is implementation specific. Good results have been obtained when the value chosen for N is approximately 0.1% of the total number enumerated compounds associated with the enumerated virtual combinatorial library.

Next, in step 108a, M compounds (e.g., M=100) are selected, based on a fitness function, from the first set of enumerated compounds. Selection of an appropriate value M is implementation specific. Good results have been obtained when the value chosen for M is approximately 0.1% of the value N.

Once M compounds are selected, based on the fitness function, from the first set of enumerated compounds, these M compounds are then deconvoluted into their building blocks (i.e., reagents), in step 110a.

In step 112a, the building blocks resulting from step 110a are combined into lists of "preferred" reagents and are used to extract a smaller "focused" enumerated library from the enumerated virtual combinatorial library. This "focused" enumerated library, which can be thought of as a sub-matrix of the larger matrix that represents the entire original enumerated virtual combinatorial library, is also referred to as the second set of enumerated compounds.

Finally, in step 116a, K compounds (e.g., K=100) are selected, based on the fitness function, from the second set of enumerated compounds. These K compounds represent near optimal set of compounds that best satisfy the fitness function. The selection of an appropriate value K is also implementation specific.

Because of its stochastic nature, the best results are obtained by repeating the above described method more than one time and combining the results. The inventors have found that repeating the above method (i.e., steps 104a-116a) three separate times and combining the results produces excellent results, although the invention is not limited to this example.

a. K Most Similar Compounds to a Query Structure

As mentioned above, the present invention can be used to efficiently and effectively perform similarity searching of a large virtual combinatorial library.

That is, in one embodiment, the fitness function of steps 108 and 116 relates to molecular similarity.

Figure 5:
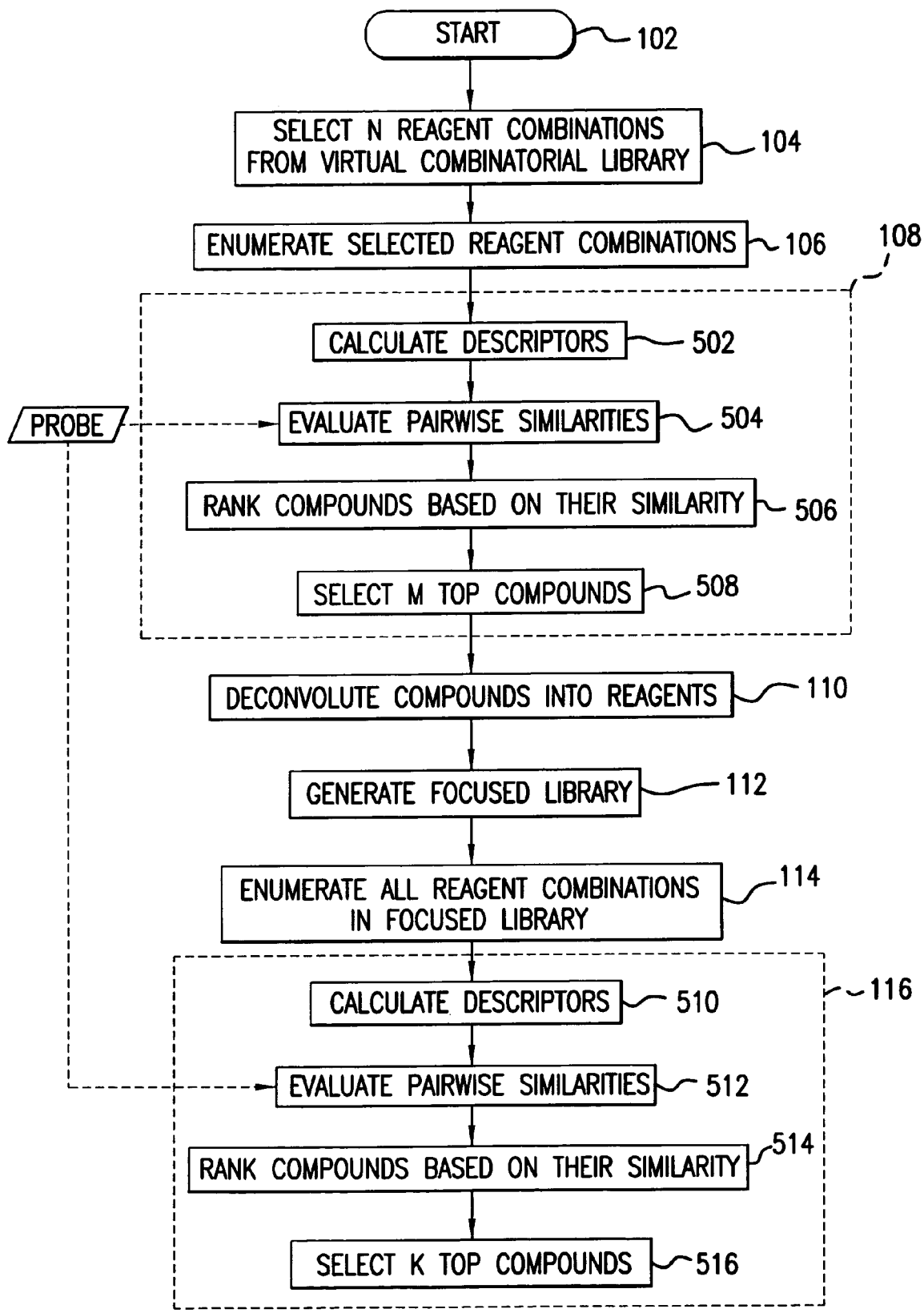
FIG. 5 is a process flowchart illustrating a method for similarity searching of virtual combinatorial libraries, according to an embodiment of the present invention.

In an example embodiment, where the fitness function is similarity to one or more query structures (i.e., lead(s) or probe(s)), step 108 of FIG. 1 can be broken into more detailed steps 502, 504, 506 and 508, and step 116 can be broken into steps 510, 512, 514 and 516, as described below, and as shown in FIG. 5.

As described above, in the discussion of FIG. 1, in steps 104 and 106, N reagent combinations are selected (e.g., randomly) from the virtual combinatorial library and each reagent combination is enumerated to produce a first set of enumerated compounds.

In step 502, the first set of enumerated compounds are characterized by calculating a prescribed set of molecular descriptors. These same descriptors are also calculated for the query structure(s) (also referred to as the probe(s)), which can be, for example, one or more drug leads. The following articles, which are incorporated herein by reference in their entirety, describe suitable example molecular descriptors: Agrafiotis "On the Use of Information Theory for Assessing Molecular Diversity," J. Chem. Inf. Comput. Sci. 1997, 37, 576-580; Agrafiotis, "Stochastic Algorithms for Maximizing Molecular Diversity," J. Chem. Inf. Comput. Sci. 1997, 37, 841-851; and Agrafiotis, "Diversity of Chemical Libraries," Encyclopedia of Computational Chemistry 1998.

In step 504, the pairwise similarities between the query structure(s) and the first set of enumerated compounds (also referred to as, the first combinatorial compound set) are evaluated using a similarity measure of choice. For example, compounds can be considered similar if they have similar numbers of atoms of the same types (constitutional similarity), similar numbers of bonds and rings of the same types and similar degree of branching (topological similarity), similar shape and surface characteristics (shape similarity) or similar electron density distribution (electrostatic similarity). Alternatively, similarity can be determined based on the presence or absence of certain features such as a common substructure (substructural similarity), the relative position and orientation of important pharmacophoric groups (pharmacophore similarity), binding affinity as predicted by a receptor binding model (receptor affinity similarity), or the degree of conformational overlap with a known receptor binder (conformational similarity). The specific similarity measure chosen will depend on the objectives, available tools, and other factors.

Once the pairwise similarities between the query structure(s) and the first set of enumerated compounds are determined, the compounds within the first combinatorial compound set (the first set of enumerated compounds) are then preferably sorted in descending (or ascending) order of similarity to the probe, in step 506. The top-ranking (or bottom-ranking) M compounds, also referred to as the highest-ranking M compounds (or lowest-ranking M compounds), are then selected in step 508. Alternatively, the top-ranking (or bottom-ranking) M compounds can be selected without prior sorting. For example, any compound having a dissimilarity value lower than a threshold value can be selected.

Next, as described above in the discussion of FIG. 1, in steps 110, 112, and 114, the M compounds are deconvoluted into reagents, a focused library is created, and all the reagent combinations in the focused library are enumerated to produce a second set of enumerated compounds.

In step 510, the compounds in the second set of enumerated compounds are characterized by calculating descriptors, preferably using the same set of molecular descriptors used to characterize the first set of enumerated compounds (in step 502) and the query structure(s).

Using the same query structure(s) (i.e., probe(s)) and the same similarity measure used in step 504 to screen the first set of enumerated compounds, the pairwise similarities between the query structure(s) and the second set of enumerated compounds are evaluated in step 512. These enumerated compounds are then preferably sorted in descending (or ascending) order of similarity to the probe(s) (i.e., query structure(s)) in step 514. Finally, in step 516 the desired number (e.g., K) of the highest-ranking (most similar) compounds are selected from the enumerated "focused" library (i.e., second set of enumerated compounds) based on their similarity scores or dissimilarity scores. Alternatively, the highest-ranking K compounds can be selected without prior sorting. For example, any compound having a dissimilarity value lower than a threshold value can be selected.

These K most similar compounds selected in step 516 can then be physically synthesized and screened to see if they include, for example, biologically active compounds or hits.

The present invention can also be used to efficiently and effectively perform similarity searching of a large enumerated virtual combinatorial library. That is, in one embodiment, the fitness function of steps 108a and 116a relates to molecular similarity. Where the fitness function is similarity to one or more query structures, steps 108a and 116a can be broken into more detailed steps. The more detailed steps associated with step 108a are similar to steps 502-508, which are discussed above in the description of FIG. 5. The more detailed steps associated with step 116*a* are similar to the detailed steps 510-516, which are also discussed above in the description of FIG. 5.

As described above, in the discussion of FIG. 1A, in step 104*a*, enumerated compounds are selected (e.g., randomly) from an enumerated combinatorial library to produce a first set of enumerated compounds. Then in step 108*a*, M compounds are selected based on a fitness function. Where the fitness function is related to similarity to a query structure, this can be accomplished as described immediately below.

The first set of enumerated compounds can be characterized by calculating a prescribed set of molecular descriptors. The same descriptors are also calculated for the one or more query structures. Next, the pairwise similarities between the query structure(s) and the first set of enumerated compounds are evaluated using a similarity measure of choice. Once the pairwise similarities between the query structure(s) and the first set of enumerated compounds are determined, the compounds within the first set of enumerated compounds are sorted based on their similarity to the probe(s). The top (or bottom) ranking M compounds are then selected. Alternatively, the top (or bottom) ranking compounds are selected without prior sorting.

Next, as described above in the discussion of FIG. 1A, in steps 110*a* and 112*a*, the M compounds are deconvoluted into reagents, and an enumerated focused library (also referred to as a second set of enumerated compounds) is extracted from the enumerated virtual combinatorial library.

As described above, in step 116*a*, K compounds are selected based on the fitness function. Where the fitness function is related to similarity to a query structure, this can be accomplished as described immediately below.

The compounds in the second set of enumerated compounds are characterized by calculating descriptors, preferably using the same set of molecular descriptors used to characterize the first set of enumerated compounds and the query structure(s). Then, using the same query structure(s) (i.e., probe(s)) and the same similarity measure used to screen the first set of enumerated compounds, the pairwise similarities between the query structure(s) and the second set of enumerated compounds are evaluated. These enumerated compounds are then sorted based on their similarity to the probe(s), and the desired number (e.g., K) of the highest (or lowest) ranking compounds is extracted from the second set of enumerated compounds based on their similarity scores or dissimilarity scores. Alternatively, the highest (or lowest) ranking K compounds can be selected without prior sorting. These K most similar selected compounds can then be physically synthesized and screened to see if they include, for example, biologically active compounds or hits.

b. Array (Sub-Matrix) of Most Similar Compounds

Similarity selections from virtual combinatorial libraries are aimed at producing candidates for future synthesis and biological testing. That is, the K compounds selected in step 516 can be synthesized and screened to identify "hits". In order to simplify and reduce the cost of synthesis, combinatorial compounds are typically synthesized in an array (i.e., sub-matrix) format. The stochastic procedure of the present invention described above can be adapted to generate such arrays (i.e., sub-matrices). After the "preferred" reagents have been identified and the focused library has been enumerated, a simulated annealing or genetic algorithm based search engine can be used to find a sub-matrix that exhibits the lowest average dissimilarity score (or highest average similarity score). In more general terms, some satisfaction of the fitness function (e.g., similarity to the probe structure) can be sacrificed in exchange for reducing the number T of reagents that make up the selected K compounds. An example of how this can be done is explained below.

Figure 6:
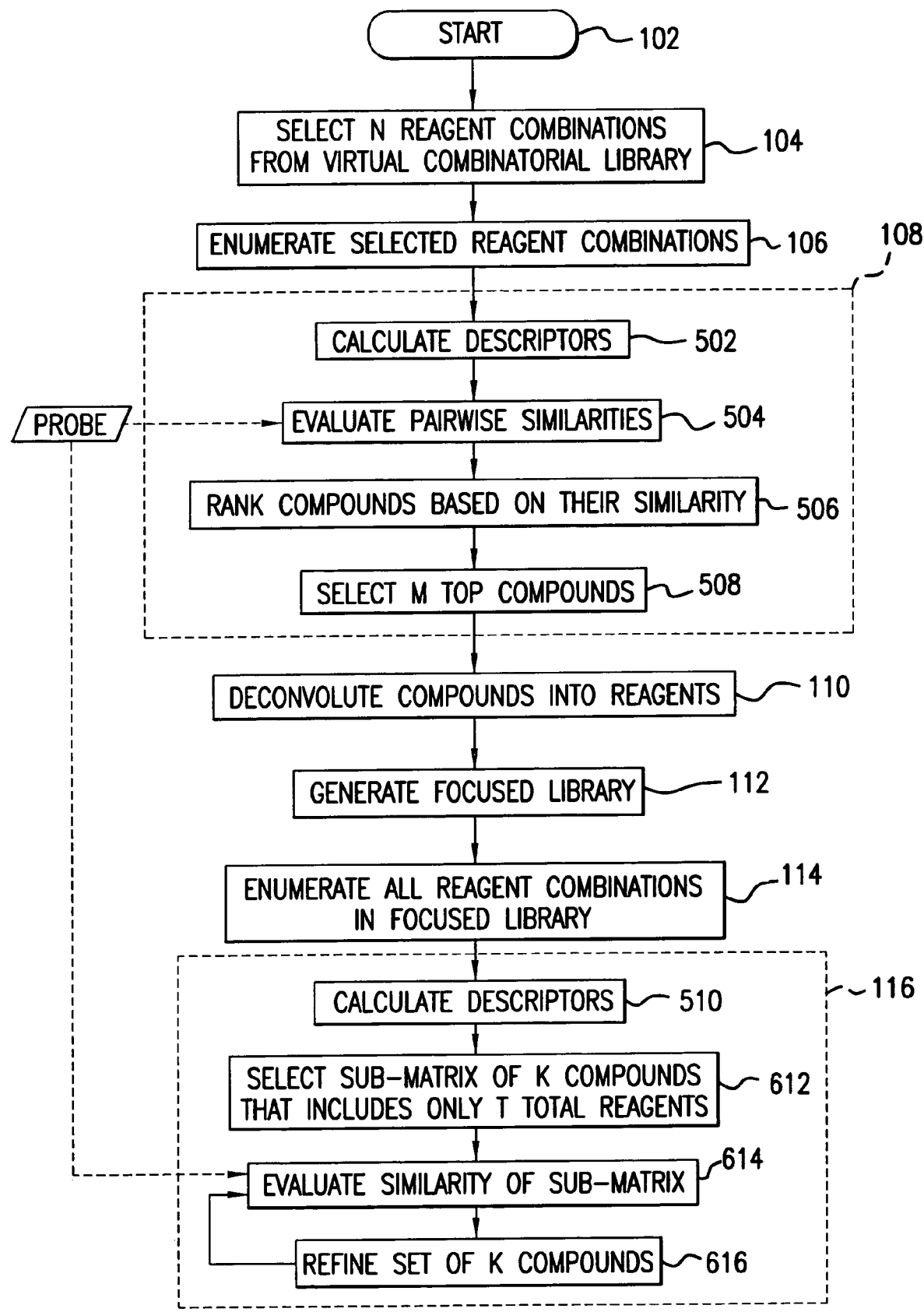
FIG. 6 is a process flowchart illustrating a method for similarity searching of virtual combinatorial libraries, wherein the total number of reagents that make up the final collection of similar compounds are reduced, according to an embodiment of the present invention.

Assume a virtual combinatorial library represents the chemical reaction $A_i+B_j>C_{ij}$, where reagent class A includes 100,000 regents and reagent class B also includes 100,000 reagents. Thus, the virtual combinatorial library representing this chemical reaction can be thought of as a 100,000×100,000 matrix, which includes $1\times10^{10}$ reagent combinations (i.e., potential compounds). If the present invention were used to select the 100 most similar compounds in step 116 (i.e., K=100), there is the possibility that 200 different reagents (i.e., 100 different A reagents and 100 different B reagents) would be required to synthesize the 100 most similar compounds. This can be costly and time consuming. Thus, it may be beneficial to choose 100 similar compounds that can be produced using, for example, only 20 different reagents (e.g., 10 different A reagents and 10 different B reagents). This can be accomplished, for example, by modifying the method of FIG. 5 so that steps 512, 514 and 516 are replaced with 612, 614 and 616, as shown in an embodiment of FIG. 6 and as described below.

In step 612, a sub-matrix of K compounds is selected, wherein the K compounds include a total number T of reagents. For example, if T=20, then the sub-matrix can be a 10×10 (i.e., 10 A reagents and 10 B reagents), a 9×11, a 8×12, . . . , a 2×18 or a 1×20 matrix.

In step 614, the similarity of the K compounds to the query structure(s) is evaluated using the same similarity measure used in step 504 to screen the original set. Preferably, this is accomplished by evaluating pairwise similarities between the query structure(s) and each compound in the sub-matrix. The result of step 614 can be a total similarity value or an average similarity value for the K compounds in the sub-matrix.

Next, in step 616, the set of K compounds is gradually refined by a series of small stochastic 'steps' to optimize the similarity of the sub-matrix. Here, the term 'step' is taken to imply a stochastic (random or semi-random) modification of the sub-matrix of K compounds. For example, the sub-matrix of K compounds can be modified by removing one of reagents associated with the sub-matrix and replacing it with a randomly selected reagent associated with the focused library. Alternatively, the sub-matrix of K compounds can be modified by altering the structure of the matrix, while keeping the total number T of reagents the same and the number K of compounds the same. For example, the sub-matrix may be changed from a 10×10 matrix to a 11×9 matrix. After the 'step' is performed, the similarity of the resulting new set (i.e., sub-matrix) of K compounds is assessed, and the similarity of the new sub-matrix is compared to the similarity of the old sub-matrix. If the new sub-matrix has a greater similarity than the old set, it replaces the old sub-matrix and the process is repeated. If the new sub-matrix does not have a greater similarity than the old sub-matrix, then the old sub-matrix is retained (as the most similar sub-matrix containing K compounds made of T reagents). This process is repeated, until a sufficiently similar sub-matrix containing K combinatorial products is selected.

This process can be controlled, for example, by a Monte-Carlo sampling protocol, a Simulated Annealing protocol, or variants thereof, which are well known to people skilled in the art. However, it should be understood that the present invention is not limited to these embodiments. Alternatively, any other suitable search/optimization algorithm can be used. The implementation of these methods should be straightforward to persons skilled in the art.

Additionally, where the fitness function is related to similarity to a query structure(s), the number or reagents used to synthesize the K compounds selected from an enumerated virtual combinatorial library, in step 116a, can be reduced in a manner similar to that described above in the discussion of steps 612-616.

c. K Most Diverse Compounds

The present invention can also be used to efficiently and effectively perform dissimilarity (diversity) searching of a large virtual combinatorial library. Accordingly, in one embodiment, the fitness function referred to in step 108 and 116 relates to molecular dissimilarity or diversity. In such an embodiment, the present invention can be used to identify the most diverse set of K compounds of a large virtual combinatorial library.

In contrast to similarity, which is typically a pairwise fitness function characterizing the degree of likeness between a given compound and a probe or target structure, diversity is a fitness function associated with a collection of compounds. The evaluation of the diversity of a collection of compounds generally involves two steps: 1) evaluation of the pairwise dissimilarities of the compounds, and 2) evaluation of the diversity of the collection based on these pairwise dissimilarities. Evaluation of pairwise dissimilarities is similar to the evaluation of pairwise similarities described above, with the exception that there is no probe structure. Hence, any suitable similarity metric and choice of descriptors can be applied. Finally, a diversity metric is used to evaluate the diversity of a collection of compounds. The following articles, which have been incorporated herein by reference in their entirety, describe such suitable similarity metric and descriptors, although the invention is not limited to that described therein: Agrafiotis "On the Use of Information Theory for Assessing Molecular Diversity," J. Chem. Inf. Comput. Sci. 1997, 37, 576-580; Agrafiotis, "Stochastic Algorithms for Maximizing Molecular Diversity," J. Chem. Inf. Comput. Sci. 1997, 37, 841-851; and Agrafiotis, "Diversity of Chemical Libraries," Encyclopedia of Computational Chemistry 1998.

Since the evaluation of diversity typically involves pairwise evaluation of dissimilarities, the number of dissimilarities which have to be evaluated grows exponentially with the size of the collection. Due to this exponential increase in computational complexity, selecting a most diverse set of compounds can be a very challenging task. The present invention provides an efficient and effective solution for selecting a diverse set of compounds from a large virtual combinatorial library.

In a preferred implementation, a stochastic version of a maximin selection algorithm is used to select a diverse subset of M compounds from the N combinatorial products selected at random. In the maximin algorithm, the diversity of a collection of compounds, can be, for example, evaluated as the minimal pairwise distance (or minimal pairwise dissimilarity) between any two compounds in the collection. A simulated annealing stochastic procedure can then be used to modify the collection with a goal to maximize the minimal pairwise distance (hence maximin).

The well known maximin function that is referred to above is:

$$f(S) = \max_i \left( \min_{j \neq i} (d_{ij}) \right)$$

or its variant:

$$f(S) = \sum_i \left( \min_{j \neq i} (d_{ij}) \right)$$

where

S is any given M-membered subset of the N-membered virtual combinatorial library; and i, j are used to index the elements of S.

This function has the advantage that it can be used with any conceivable dissimilarity index and does not require a metric space. In practice, the inventors have found the later equation to be smoother and thus much easier to optimize in a Monte-Carlo environment. Of course any other suitable selection algorithm can be used to select a diverse subset of M compounds from the N combinatorial products.

Figure 7:
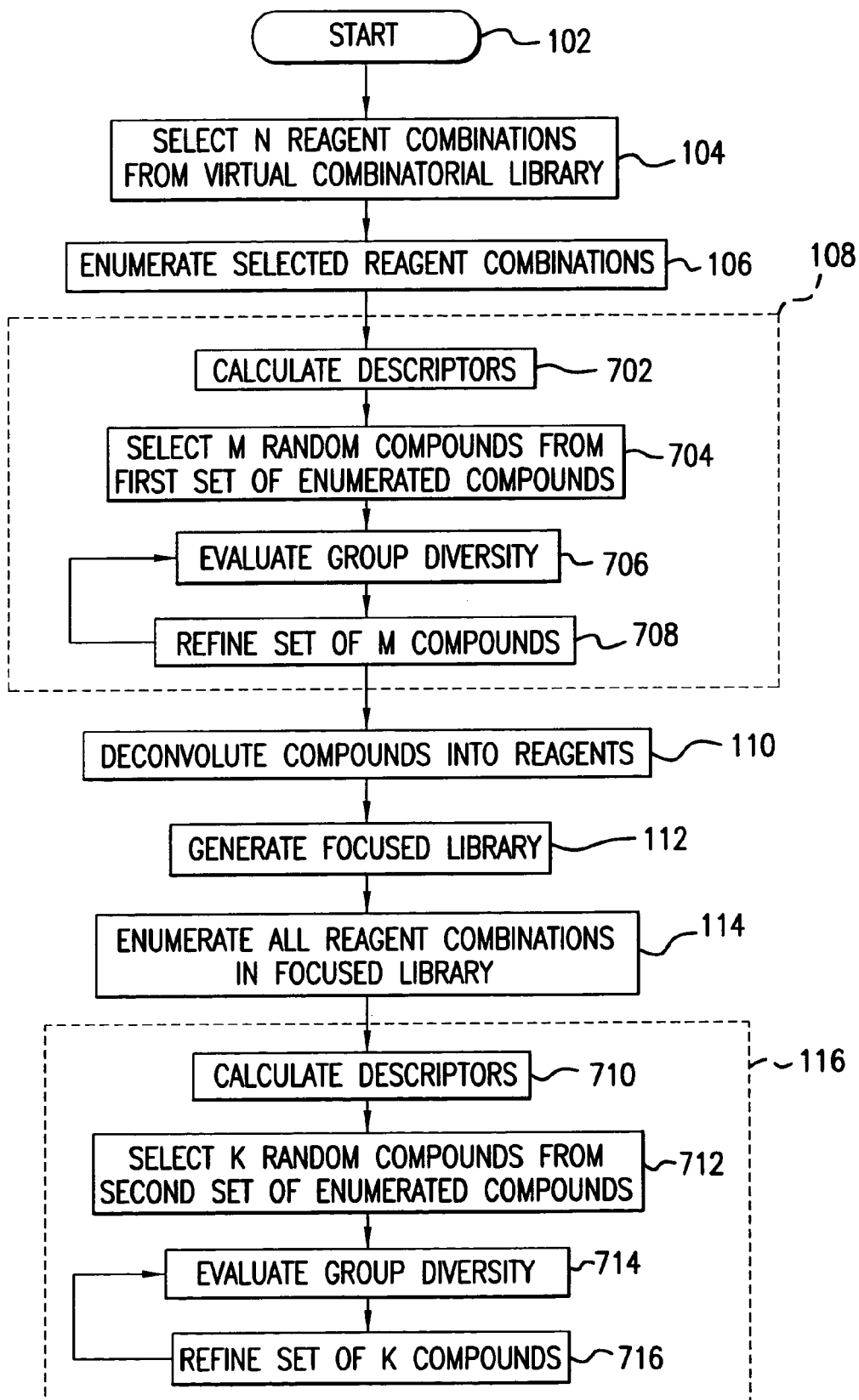
FIG. 7 is a process flowchart illustrating a method for dissimilarity (diversity) searching of virtual combinatorial libraries, according to an embodiment of the present invention.

More specifically, where the fitness function is diversity, step 108 of FIG. 1 can be broken into more detailed steps 702, 704, 706 and 708, and step 116 can be broken into steps 710, 712, 714 and 716, as shown in the example embodiment of FIG. 7 and described below.

As described above, in the discussion of FIG. 1, in steps 104 and 106, N reagent combinations are selected (e.g., randomly) from the virtual combinatorial library and each reagent combination is enumerated to produce a first set of enumerate compounds.

In step 702, the first set of N enumerated compounds are characterized by calculating a prescribed set of molecular descriptors. In step 704, an initial set of M compounds is selected (e.g., at random) from the first set of N enumerated compounds. The diversity of the M compounds is then evaluated using methods known in the art in step 706. As discussed above, the evaluation of the diversity of a collection of compounds generally involves evaluating the pairwise dissimilarities of the M compounds, and evaluating the diversity of the collection based on these pairwise dissimilarities.

Next, in step 708, the set of M compounds is gradually refined by a series of small stochastic 'steps' to optimize the diversity of the set. Here, the term 'step' is taken to imply a stochastic (random or semi-random) modification of the set of M compounds. For example, the set of M compounds can be modified by removing one of the M compounds and replacing it with a randomly selected one of the compounds in the first set of enumerated compounds. After the 'step' is performed, the diversity of the resulting new set of M compounds is assessed, and the diversity of the new set is compared to the diversity of the old set using any suitable comparison criterion. If the new set has a greater diversity than the old set, it replaces the old set and the process is repeated. If the new set does not have a greater diversity than the old set, then the old set is retained (as the most diverse set) and the process is repeated. This process is preferably repeated until the diversity of the set of M compounds essentially plateaus. This process can be controlled, for example, by a Monte-Carlo sampling protocol, a Simulated Annealing protocol, or variants thereof, which are well known to people skilled in the art. However, it should be understood that the present invention is not limited to these embodiments. Alternatively, any other suitable search/optimization algorithm can be used. The implementation of these methods should be straightforward to persons skilled in the art.

After a sufficiently diverse subset of M combinatorial products is selected, contributing reagents are identified in step 110 by deconvoluting the M compounds. A focused library is then created in step 112, and all the reagent combinations of the focused library are enumerated in step 114 to create a second set of enumerated compounds.

Finally, the selection algorithm is applied again to select a sufficiently diverse subset of K compounds from the focused library. More specifically, in step 710 molecular descriptors are calculated for each of the enumerated compounds. In step 712, an initial set of K compounds is selected (e.g., at random) from the second set of enumerated compounds. The diversity of the K compounds is then evaluated using methods known in the art in step 714. Next, in step 716, the set of K compounds is gradually refined by a series of small stochastic 'steps', as in step 708, until a nearly optimal diverse subset of K combinatorial products is selected.

An embodiment of the present invention can also be used to efficiently and effectively perform dissimilarity (diversity) searching of a large enumerated virtual combinatorial library. Accordingly, in one embodiment, the fitness function referred to in steps 108a and 116a relate to molecular dissimilarity or diversity. In such an embodiment, the present invention can be used to identify the most diverse set of K compounds of a large enumerated virtual combinatorial library.

Figure 1A:
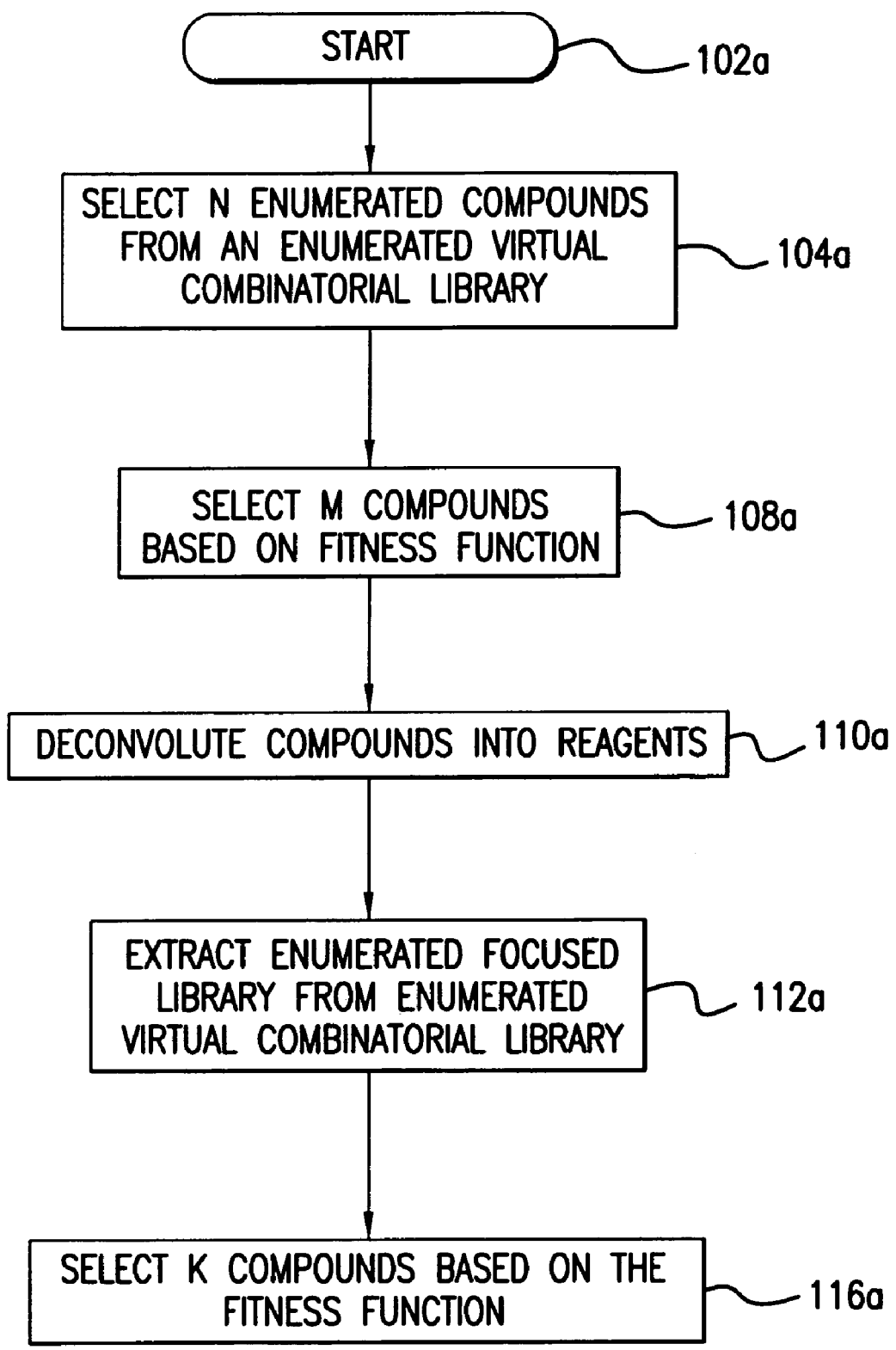
FIG. 1A is a process flowchart illustrating a method for searching of enumerated virtual combinatorial libraries, according to an embodiment of the present invention.

More specifically, where the fitness function is diversity, steps 108a and 116a of FIG. 1A can be broken into more detailed steps. The more detailed steps corresponding to step 108a are similar to steps 702-708, which are discussed above in the description of FIG. 7. The more detailed steps corresponding to step 116a are similar to steps 710-716, which are also discussed above in the description of FIG. 7.

As described above, in the discussion of FIG. 1A, in step 104a, N enumerated compounds are selected (e.g., randomly) from an enumerated virtual combinatorial library to produce a first set of enumerate compounds. Where the fitness function is diversity, the method of selecting M compounds in step 108a can be accomplished as described immediately below.

First, the set of N enumerated compounds are characterized by calculating a prescribed set of molecular descriptors. Next, an initial set of M compounds is selected (e.g., at random) from the first set of N enumerated compounds. The diversity of the M compounds is then evaluated using methods known in the art. As discussed above, the evaluation of the diversity of a collection of compounds generally involves evaluating the pairwise dissimilarities of the M compounds, and evaluating the diversity of the collection based on these pairwise dissimilarities.

Next, the set of M compounds is gradually refined by a series of small stochastic 'steps' to optimize the diversity of the set. Here, the term 'step' is taken to imply a stochastic (random or semi-random) modification of the set of M compounds. For example, the set of M compounds can be modified by removing one of the M compounds and replacing it with a randomly selected one of the compounds in the first set of enumerated compounds. After the 'step' is performed, the diversity of the resulting new set of M compounds is assessed, and the diversity of the new set is compared to the diversity of the old set using any suitable comparison criterion. If the new set has a greater diversity than the old set, it replaces the old set and the process is repeated. If the new set does not have a greater diversity than the old set, then the old set is retained (as the most diverse set) and the process is repeated. This process is preferably repeated until the diversity of the set of M compounds essentially plateaus. This process can be controlled by any suitable search/optimization algorithm/process, including, but not limited to, a Monte-Carlo sampling protocol, a Simulated Annealing protocol, or variants thereof, which are well known to people skilled in the art.

After a sufficiently diverse subset of M enumerated compounds is selected, contributing reagents are identified by deconvoluting the M compounds. An enumerated focused library is then extracted, based on the reagents, from the enumerated virtual combinatorial library. The enumerated focused library is also referred to as the second set of enumerated compounds.

Finally, the selection algorithm is applied again to select a sufficiently diverse subset of K compounds from the enumerated focused library. More specifically, molecular descriptors are calculated for each of the enumerated compounds in the enumerated focused library. An initial set of K compounds is selected (e.g., at random) from the second set of enumerated compounds and the diversity of the K compounds is then evaluated. The set of K compounds is gradually refined by a series of small stochastic 'steps' until a nearly optimal diverse subset of K enumerated compounds is selected.

d. Array (Sub-Matrix) of Most Diverse Compounds

Figure 8:
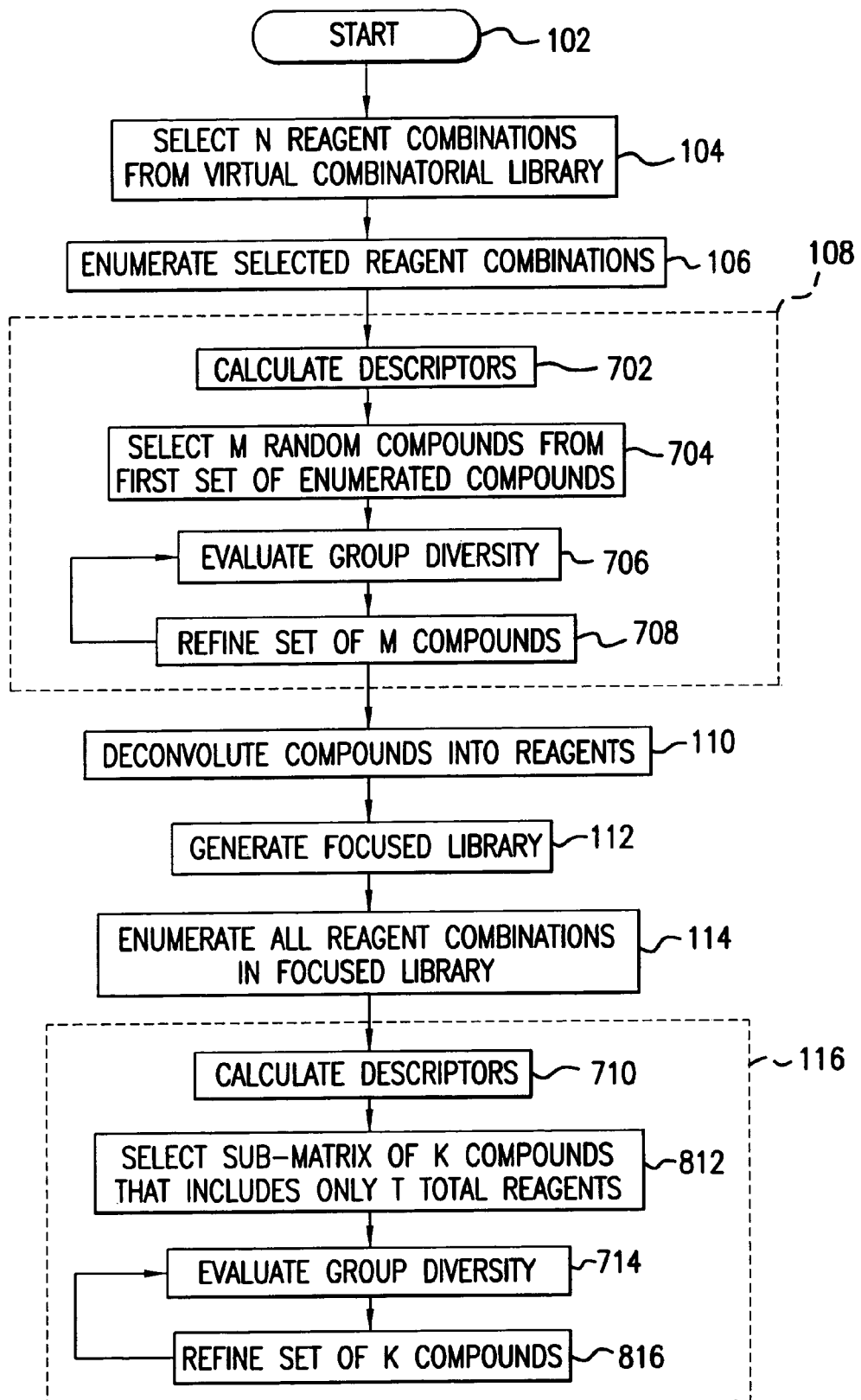
FIG. 8 is a process flowchart illustrating a method for dissimilarity (diversity) searching of virtual combinatorial libraries, wherein the total number of reagents that make up the final collection of dissimilar compounds is reduced, according to an embodiment of the present invention.

Diversity selections from virtual combinatorial libraries are also aimed at producing candidates for future synthesis and biological testing. That is, the K compounds selected in step 716 can be synthesized and screened to identify "hits". In order to simplify and reduce the cost of synthesis, combinatorial compounds are typically synthesized in an array (i.e., sub-matrix) format. The stochastic procedure of the present invention can be easily adapted to generate such arrays (i.e., sub-matrices). That is, some satisfaction of the fitness function (e.g., dissimilarity of a collection of compounds) can be sacrificed in exchange for reducing the total number T of reagents that make up the K compounds. This can be accomplished, for example, by modifying the method of FIG. 7 so that steps 712 and 716 are replaced with steps 812 and 816, as shown in FIG. 8 and as described below.

In step 812, a sub-matrix of K compounds is selected, such that the K compounds include a total of T reagents. In step 714, the dissimilarity of the collection of K compounds is evaluated. Next, in step 816, the set (i.e., sub-matrix) of K compounds is gradually refined by a series of small stochastic 'steps' to optimize the dissimilarity of the sub-matrix. For example, the sub-matrix of K compounds can be modified by removing one of reagents associated with the sub-matrix and replacing it with a randomly selected reagent associated with the focused library. Alternatively, the sub-matrix of K compounds can be modified by altering the structure of the sub-matrix, while keeping the total number T of reagents the same and the number K of compounds the same. For example, the sub-matrix may be changed from a 10×10 matrix to a 11×9 matrix. After the 'step' is performed, the diversity (i.e., dissimilarity) of the resulting new set of K compounds is assessed, and the diversity of the new sub-matrix is compared to the diversity of the old sub-matrix. If the new sub-matrix has a greater diversity than the old set, it replaces the old sub-matrix and the process is repeated. If the new sub-matrix does not have a greater diversity than the old sub-matrix, then the old sub-matrix is retained (as the most dissimilar sub-matrix containing K compounds made of T reagents). This process is repeated, until a sufficiently dissimilar sub-matrix containing K combinatorial products is selected. For example, this process can be repeated until the diversity of the K compounds essentially plateaus.

This process can be controlled, for example, by a Monte-Carlo sampling protocol, a Simulated Annealing protocol, or variants thereof, which are well known to people skilled in the art. However, it should be understood that the present invention is not limited to these embodiments. Alternatively, any other suitable search/optimization algorithm can be used. The implementation of these methods should be straightforward to persons skilled in the art.

Additionally, where the fitness function is related to dissimilarity (diversity) searching of a large enumerated virtual combinatorial library, the number of reagents used to synthesize the K compounds selected from the enumerated virtual combinatorial library, in step 116a, can be reduced in a manner similar to that discussed above in the description of steps 710, 812, 714 and 816.

For additional details of such an example simulated annealing or genetic search engine refer to the article entitled "Stochastic Algorithms for Maximizing Molecular Diversity," which has been incorporated by reference above.

3. Experimental Results and Discussion

Figure 9A:
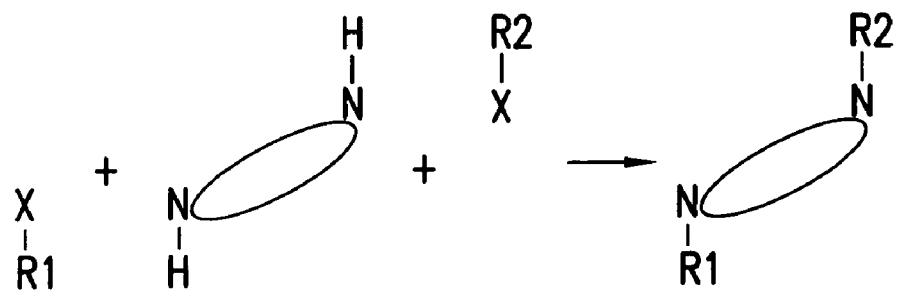
FIG. 9A illustrates a synthetic protocol for a diamine virtual combinatorial library that was used to demonstrate the effectiveness of the present invention.

The effectiveness of the present invention has been demonstrated by the inventors through experiments using two different virtual combinatorial libraries. The first was a diamine virtual combinatorial library, generated by combining a diamine core with a set of alkyl halides or acid chlorides, as shown in FIG. 9A. The structure 902a represents a diamine; R1-X and R2-X each independently represent an alkyl halide or acid chloride. Although physical synthesis of this library could prove problematic (the synthetic sequence involves selective protection of one of the amines and introduction of the first side chain, followed by deprotection and introduction of the second side chain), for the purpose of a study it can be assumed that one of the amino groups on the diamine core reacts with the first reagent, while the other reacts with the second reagent. A substructure search in the Available Chemicals Directory (ACD) yielded 1,036 suitable diamines and 826 alkylating/acylating agents. These reagents were used to generate a virtual combinatorial library associated with over 706 million (1036'826'826) possible products (i.e., reagent combinations). Since descriptors for the fully enumerated virtual combinatorial library could not be computed in a timely fashion, and since for validation purposes the inventors needed to compare their results with conventional selections from a fully characterized library, a smaller 6.75 million-membered library (i.e., a virtual combinatorial library associated with 6.75 million reagent combinations) was produced by choosing 300 diamines and 150 alkylating/acylating agents at random. Hereafter, the term "diamine virtual combinatorial library" will refer to this smaller library, unless noted otherwise. Examples of diamines, and acidchlorides and halocarbons (i.e., alkylating/acylating agents), associated with this smaller library are shown in FIG. 21.

Figure 9B:
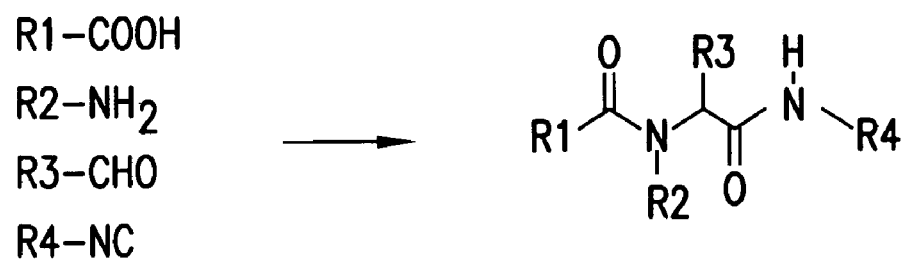
FIG. 9B illustrates a synthetic protocol for a Ugi reaction that was also used to demonstrate the effectiveness of the present invention.

The second virtual combinatorial library was based on the Ugi reaction, and involves an organic acid (R1-COOH), an amine (R2-NH$_2$), an aldehyde (R3-CHO) and an isonitrile (R4-CN), as shown in FIG. 9B. A substructure search in the ACD yielded 1,681 suitable acids, 594 suitable amines, 37 suitable aldehydes, and 17 suitable isonitriles. These reagents were used to build a virtual combinatorial library associated with over 628 million possible compounds (1681'594'37'17). Again, for validation purposes a smaller 6.29 million-membered library (i.e., a virtual combinatorial library associated with 6.29 million reagent combinations) was produced by choosing a random set of 100 acids and 100 amines. Hereafter, the term "Ugi virtual combinatorial library" will refer to this smaller library, unless noted otherwise. Examples of acids, amines, aldehydes, and isonitriles associated with this smaller library are shown in FIG. 22.

First, every reagent combination (approximately 6.75 million) associated with the diamine virtual combinatorial library was enumerated to produce a full set of enumerated compounds. The similarities of the enumerated compounds to a query structure (an antiarrhythmic agent), shown in FIG. 10A, were then evaluated. The evaluation of molecular similarity was based on a standard set of 117 topological descriptors computed using a C++ descriptor generation class from the DirectedDiversity® API toolkit, available from 3-Dimensional Pharmaceuticals, Inc., Exton, Pa. The descriptors included a well-established set of topological indices with a long, successful history in structure-activity correlation such as molecular connectivity indices, kappa shape indices, subgraph counts, information-theoretic indices, Bonchev-Trinajstis indices, and topological state indices. These indices are discussed in detail in Hall et al. "The Molecular Connectivity Chi Indexes and Kappa Shape Indexes in Structure-Property Relations," Reviews of Computational Chemistry, Chap. 9, pp 367-422, eds. Donald Boyd and Ken Lipkowitz, VCH Publishers, Inc. (1991), and Bonchev et al. "Information Theory, Distance Matrix, and Molecular Branching," J. Chem. Phys. 1977, 67, pp 4517-4533, both of which are incorporated herein by reference in their entirety. The calculated descriptors were normalized, and decorrelated using principal component analysis. The principal components which accounted for 99% of the total variance in the data (typically 25-30 principal components) were used to define the similarity space. Pairwise dissimilarity scores were calculated as Euclidean distances between the vectors associated with the respective compounds in the space defined by the selected principal components. A higher dissimilarity score indicates compounds that are less similar to each other, that is, more distant from each other in the principal component space.

Figure 11A:
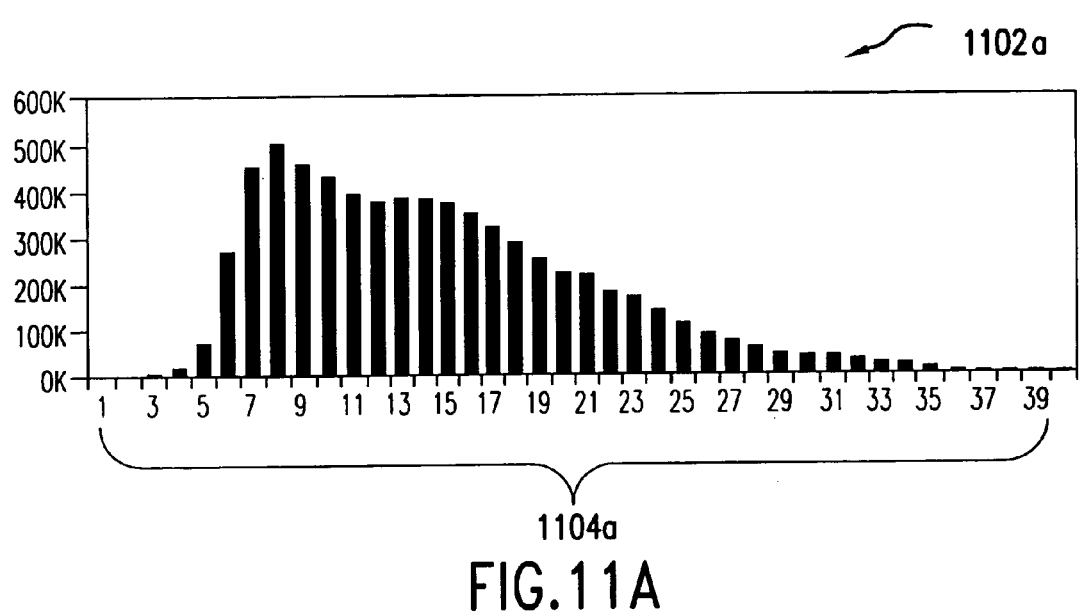
FIG. 11A is a graph that illustrates a similarity profile of the diamine virtual combinatorial library of FIG. 9A.

Based on calculated dissimilarity scores, a similarity profile 1102a, shown in FIG. 11A, of the diamine virtual combinatorial library was obtained by counting the number of compounds falling in each similarity bin 1104a. According to the distribution, the majority of compounds had dissimilarity scores higher than 4.0. Next, the 100 most similar compounds with the lowest dissimilarity score were selected, and were used as a reference to compare all subsequent similarity selections drawn from the diamine virtual combinatorial library. These reference compounds represent the absolute best similarity selection of that size which can be obtained from the diamine virtual combinatorial library using the prescribed descriptors, similarity measure, and query structure.

Figure 10A:
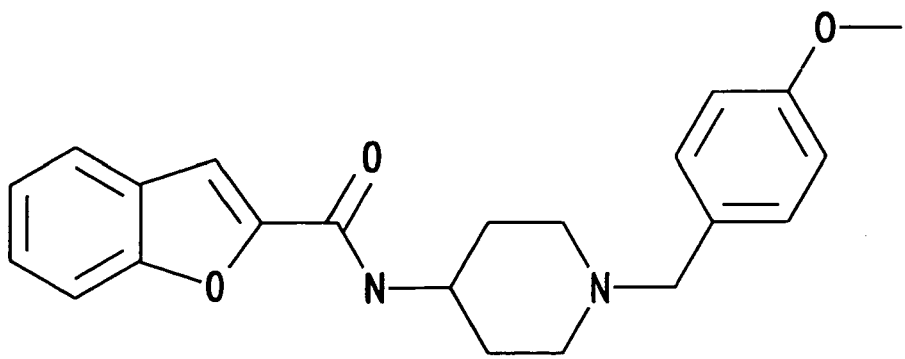
FIG. 10A shows a query structure that was used to demonstrate the effectiveness of the present invention.
Figure 10B:
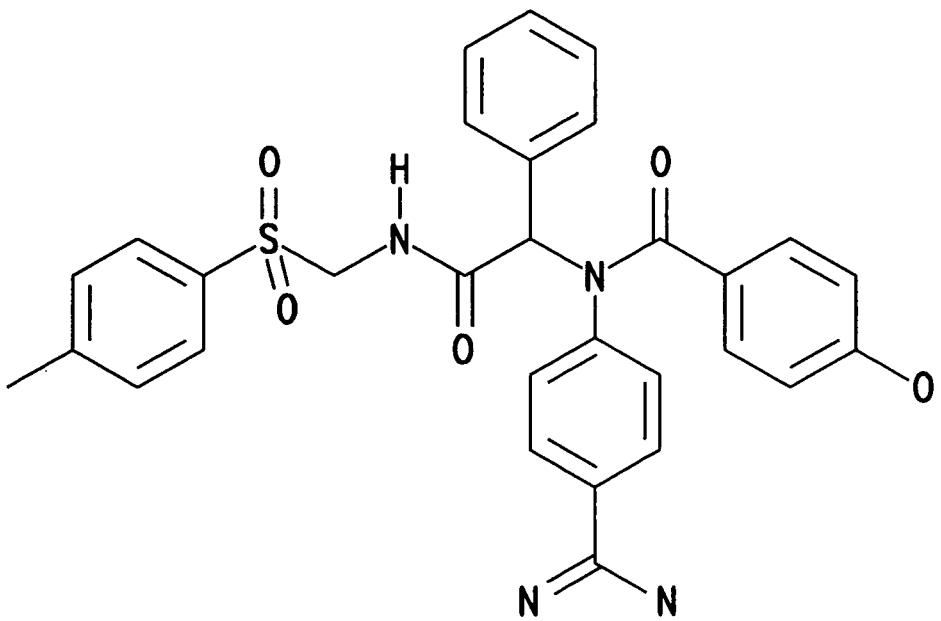
FIG. 10B shows another query structure that was used to demonstrate the effectiveness of the present invention.
Figure 11B:
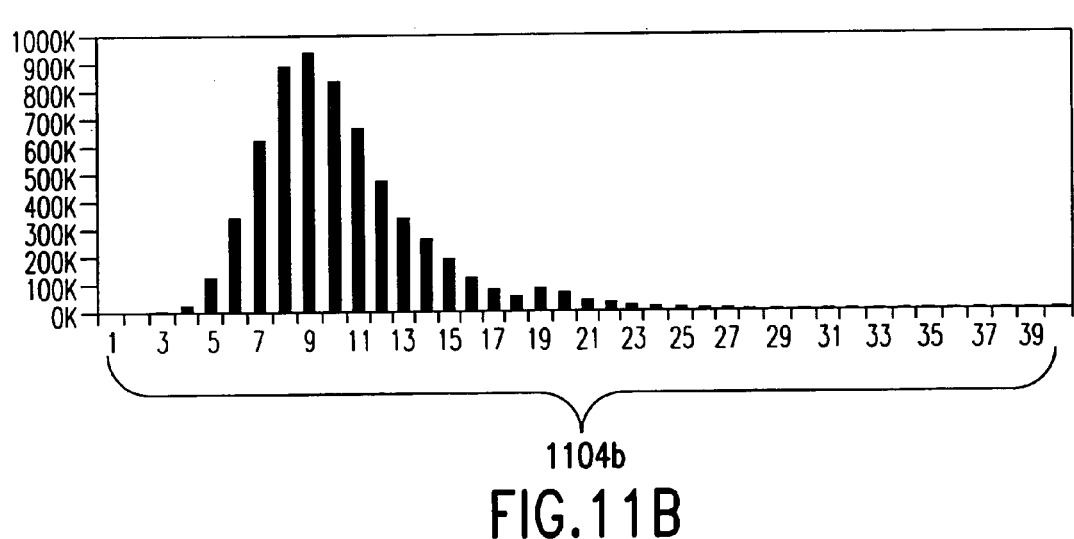
FIG. 11B is a graph that illustrates a similarity profile of the Ugi virtual combinatorial library of FIG. 9B.

Likewise, every reagent combination (approximately 6.29 million) associated with the Ugi virtual combinatorial library was also enumerated and the similarities of the enumerated compounds to the query structure (a 1.4 µM thrombin inhibitor), shown in FIG. 10B, were evaluated. Although the enumerated compounds associated with the Ugi virtual combinatorial library exhibited a more sharp similarity distribution, as shown by the similarity profile 1102b in FIG. 11B, the vast majority of the compounds in that library also had dissimilarity scores higher than 4.0. Again, the 100 most similar compounds were identified and were used as a reference to compare subsequent similarity selections from that library.

Next, the selection method of the present invention, outlined in the discussion of FIG. 5 above, was employed to select the 100 highest-scoring compounds from the diamine combinatorial virtual library based on their similarity to the same query structure of FIG. 10A. Initially 100,000 reagent combinations were selected at random from the virtual combinatorial library (Step 104, FIG. 5) and enumerated (Step 106). Descriptors were calculated for the enumerated compounds (Step 502), pairwise similarity to the query structure was evaluated (Step 504), and the enumerated compounds were ranked based on their similarity (Step 506). The 100 highest-ranking compounds were selected (508) and deconvoluted to produce lists of "preferred" reagents (Step 110).

The list of "preferred" reagents was then used to produce the "focused" library (Step 112) and all reagent combinations associated with that "focused" library were enumerated (Step 114). Descriptors were calculated for the enumerated compounds (Step 510), pairwise similarity to the query structure was evaluated (Step 512), and the enumerated compounds were ranked based on their similarity (Step 514). The 100 highest-ranking (most similar) compounds were then selected (Step 516) from the fully enumerated "focused" library based on their similarity to query structure of FIG. 10A.

Because 100,000 reagent combinations of the virtual combinatorial library were enumerated (i.e., N=100,000), and the 100 highest-ranking compounds were selected and deconvoluted to produce lists of "preferred" reagents (i.e., M=100), the selection cycle was accordingly code-named 100K/100, and this naming scheme was used for all the remaining selections.

Figure 12A:
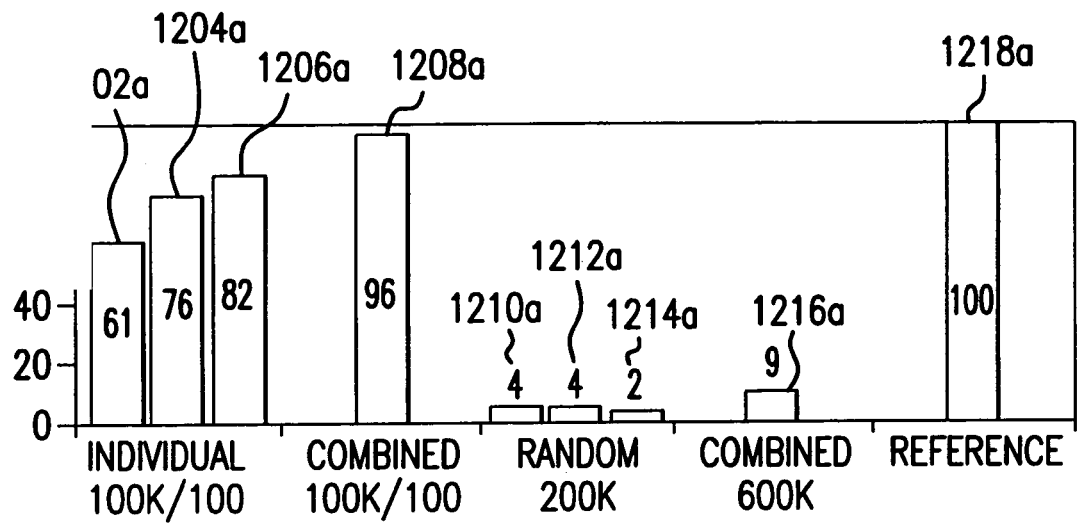
FIGS. 12A and 12B are graphs that illustrate the overlap between stochastic selections, generated using the present invention, and reference selections.

The dissimilarity scores and identities of the selected 100 compounds derived using the present invention were compared with the dissimilarity scores and identities of the reference selection derived from the fully enumerated library. Based on the average dissimilarity scores of the selected compounds (1.37 vs 1.30), the two selections (i.e., the selection using the present invention and the reference selection) were quite comparable. In fact, as shown in FIG. 12A, which shows the overlap between stochastic selections 1202a, 1204a, 1206a, and reference selection 1218a, most of the compounds in the reference set were also found in the stochastic selection. After repeating the stochastic procedure two more times with different random seeds and combining the results, the overlap with the reference selection rose to 96 out of 100 compounds, as shown at 1208a of FIG. 12A.

Figure 12B:
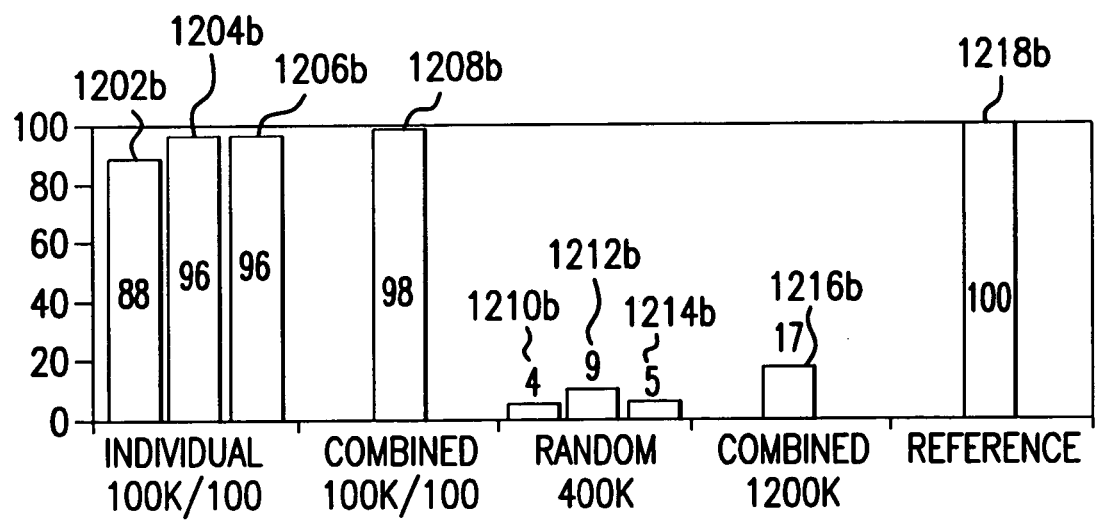

The same procedure was also applied to the Ugi library and an even better overlap with the reference selection was achieved, as shown in FIG. 12B.

Referring to FIG. 13, in three independent 100K/100 runs on the diamine virtual combinatorial library, the 100 highest-ranking compounds selected in Step 508 were derived, on average, from 108 reagents, which produced approximately a 50,000-membered enumerated focused library during Step 112, as shown in row 1304, of Table 1302. Thus, even though only approximately 450,000 compounds (or approximately 7% of the possible reagent combinations associated with the diamine virtual combinatorial library) were explicitly enumerated, described, and compared to the query structure over all three runs, 96% of the best possible hits (i.e., most similar compounds) were retrieved. In fact, the number of unique compounds screened is substantially lower due to the substantial overlap between the focused libraries generated in the three independent runs.

For comparison, as shown in row 1306 of Table 1302, when three independent screens of 200,000 random reagent combinations relating to the diamine virtual combinatorial library were selected and enumerated, a total of only 9 (or 3 on average) out of the 100 most similar structures were retrieved. (This is also shown in FIG. 12A at 1210a, 1212a, 1214a and 1216a.) This result is not surprising since 600,000 compounds constitute approximately 10% of the entire 6.75 million-member diamine library.

In the case of the Ugi virtual combinatorial library, the 100 highest-ranking compounds selected during Step 508 produced an average of 99 "preferred" reagents. However, since this is a 4-component library, the resulting fully enumerated focused libraries were larger—270,000 compounds on average. Thus, after three independent runs, a relatively higher proportion of the possible compounds associated with the Ugi virtual combinatorial library was screened (18%), which probably explains the higher percentage (98%) of compounds recovered from the reference set, as shown in row 1308 of Table 1302.

For comparison, as shown in row 1310 of Table 1302, when three independent screens of 400,000 random reagent combinations relating to the Ugi virtual combinatorial library were selected and enumerated, a total of only 17 (or 6 on average) out of the 100 most similar structures were retrieved.

The efficiency of the method of the present invention should be judged, for example, by two factors: 1) how good is the final selection, and 2) how many virtual compounds were actually screened (also referred to as cost). These two criteria are naturally connected: for example, if all virtual compounds were enumerated and screened, then the best possible selection would have been obtained. The goal is to find a nearly optimal set by enumerating and comparing the smallest possible number of compounds, and thus complete the task in a reasonable time frame. The two parameters of the selection procedure that affect its outcome are the size N of the initial pool (Step 104) and the number M of the highest-ranking compounds (selected in Step 508) used to generate the focused library (in Step 112). In order to assess the effect of these parameters, a series of selections were carried out using several combinations of these parameters. For each combination, three independent runs were carried out starting from a different random seed, and the results were combined and summarized in Table 1302.

Figure 14A:
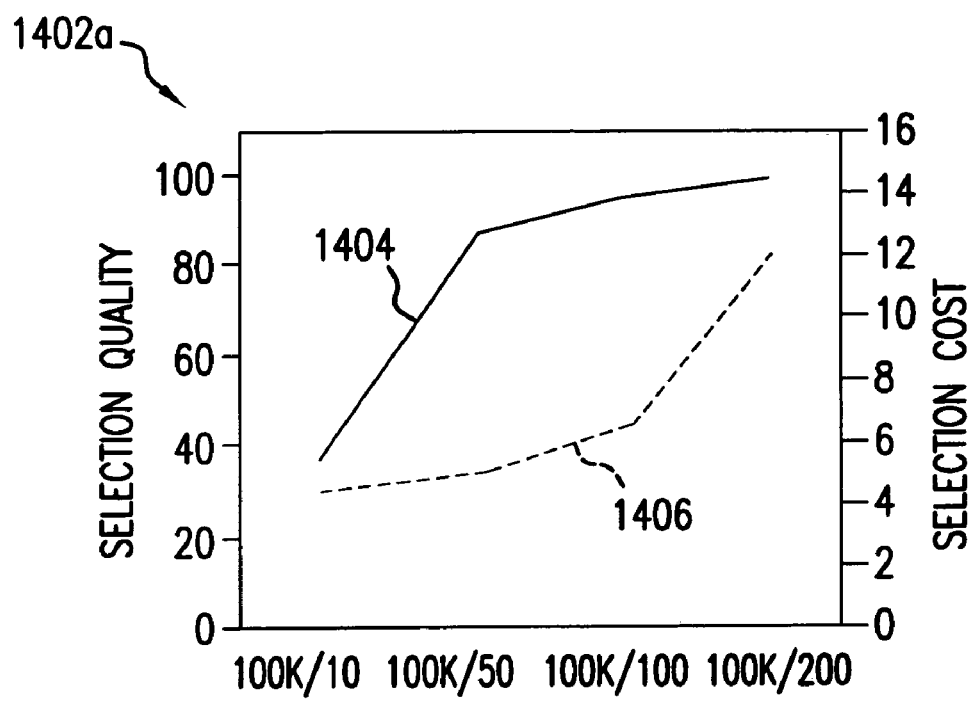
FIGS. 14A, 14B, 15, 16A, 16B and 17 are graphs that show how the selection of particular variables affects experimental results of the present invention.
Figure 14B:
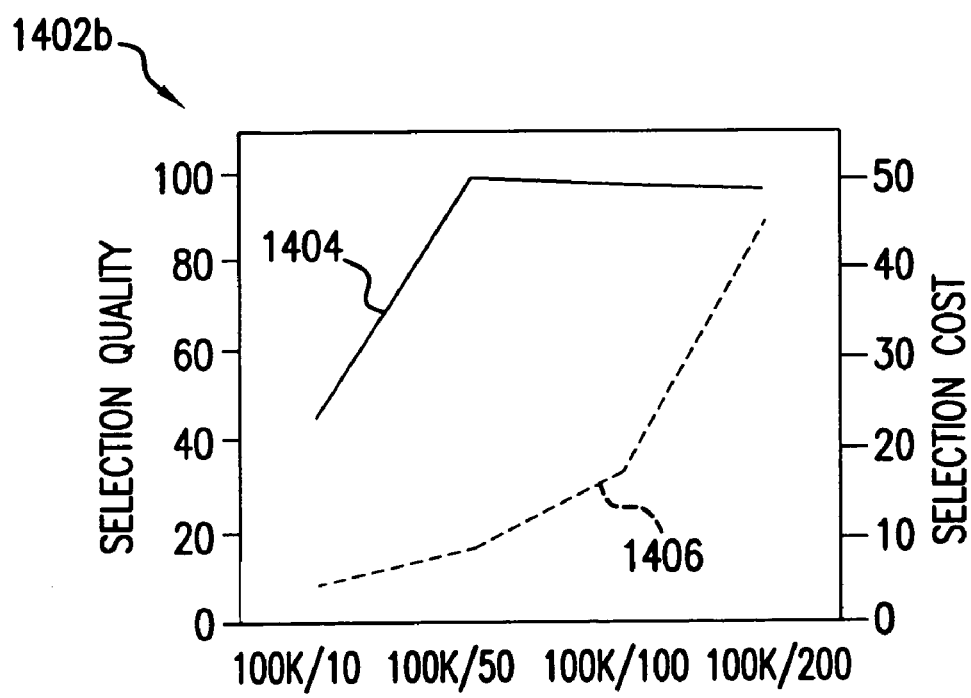

The number of highest-ranking compounds (i.e., the number M of compounds selected in step 508) used to determine the "preferred" reagents, which were used to produce the focused libraries, appears to have had the most significant effect on the quality of the final selection. This is not surprising, since a smaller number of compounds produces a smaller list of reagents which leads to a smaller focused library and, therefore, a smaller chance to retrieve the best hits. On the other hand, if that number is too large, much larger focused libraries are produced, and the execution speed of the algorithm is compromised, as shown in FIG. 14. Thus, the optimal number of highest-ranking compounds must be determined based on both the quality and cost of the final selection.

Graph 1402a shows the effect of the number of top-ranked M compounds chosen in step 508 on the quality and cost of the final selection from the diamine virtual combinatorial library. Graph 1402b shows the effect of the number of top-ranked compounds chosen in step 508 on the quality and cost of the final selection from the Ugi virtual combinatorial library. In each graph, the selection quality, shown as a solid line 1404, is measured in the percent overlap with the corresponding reference selection. The cost, shown as a dotted line 1406, is the cumulative percent of total number of virtual compounds evaluated. The cost is directly proportional to the amount of time it takes to perform enumeration.

Figure 15:
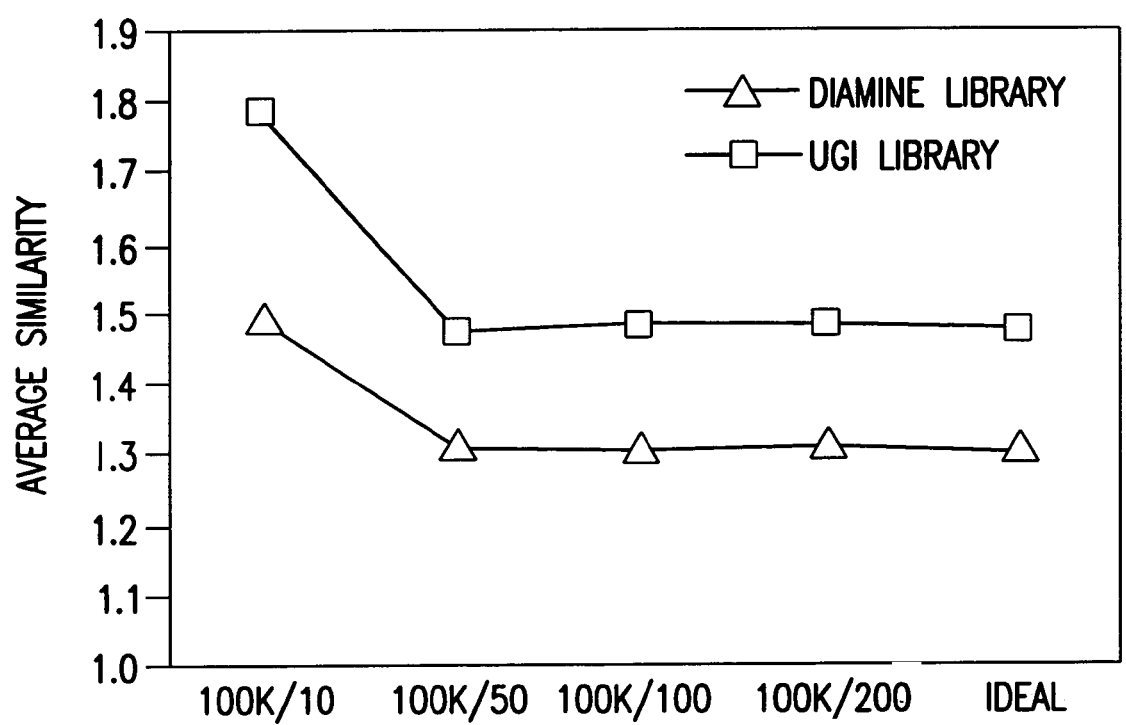

For the diamine virtual combinatorial library, 100 was the optimal number, whereas for the Ugi library just 50 compounds were sufficient to obtain the best selection. Undoubtedly, the optimal number of compounds to choose will vary from one virtual library to another, and will depend on the query structure as well. One can start with a small number and gradually increase it until the average dissimilarity score of the final selection reaches a plateau, as shown in FIG. 15. Specifically, FIG. 15 shows the average dissimilarity score of the final selection (selected in Step 516) as a function of the number M of top-ranked compounds chosen in step 508.

Figure 16A:
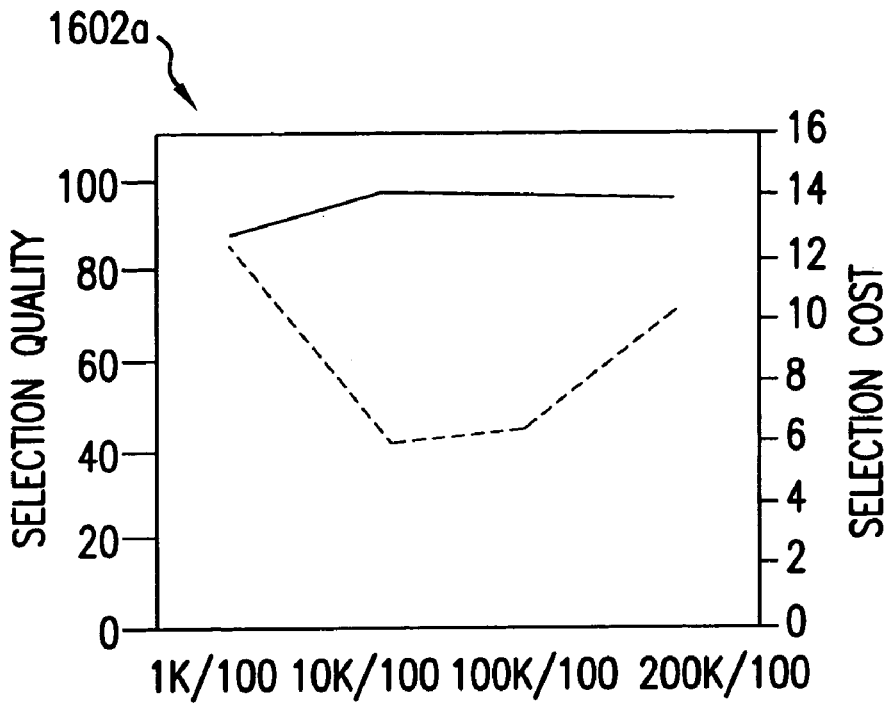
Figure 16B:
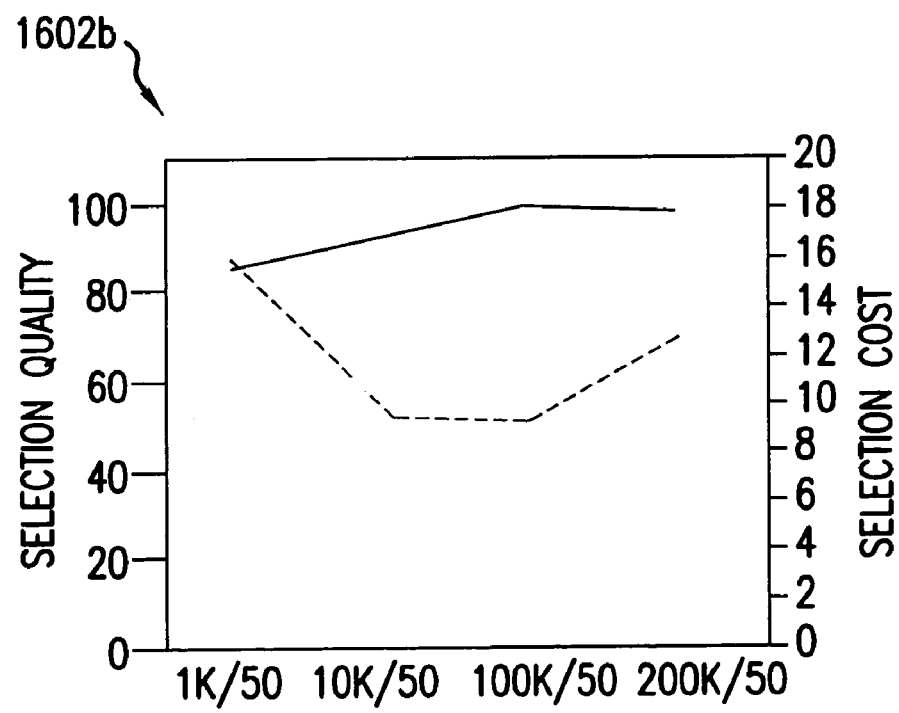
Figure 17A:
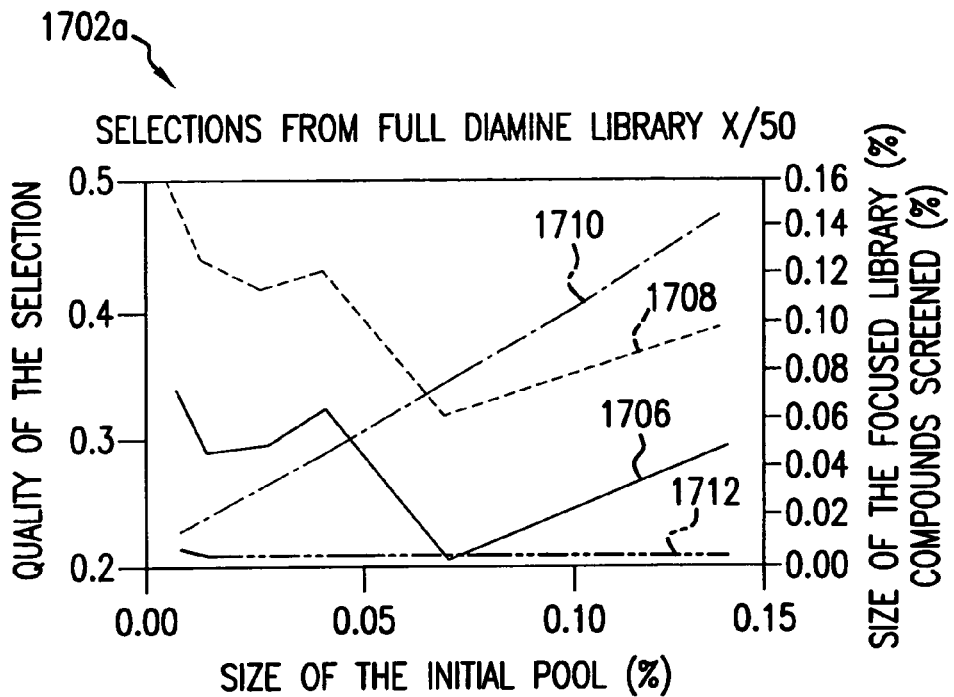
Figure 17B:
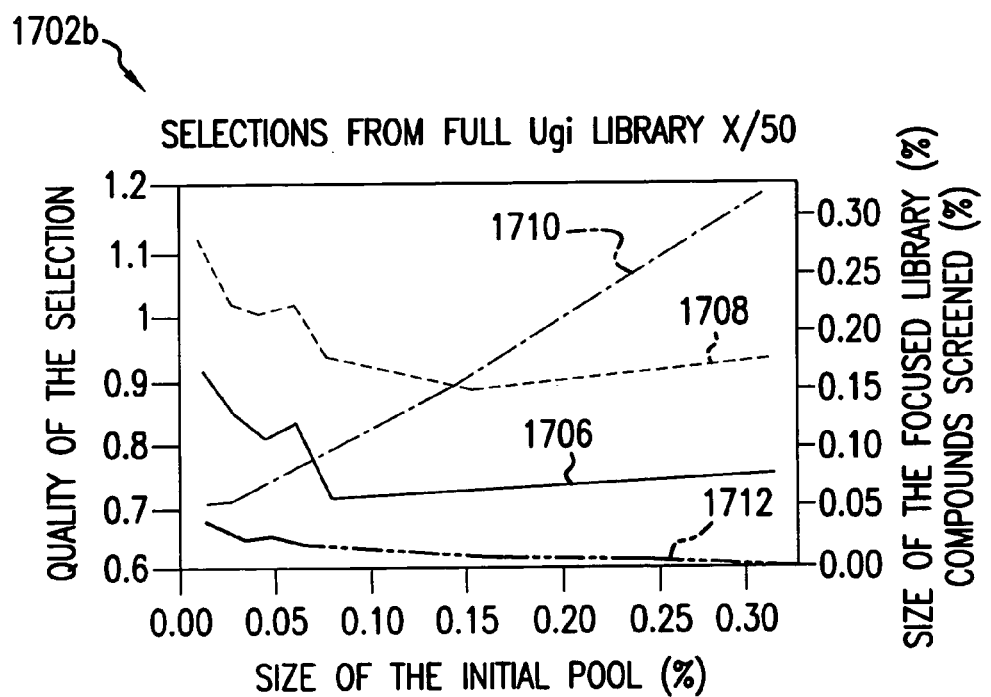
Figure 17C:
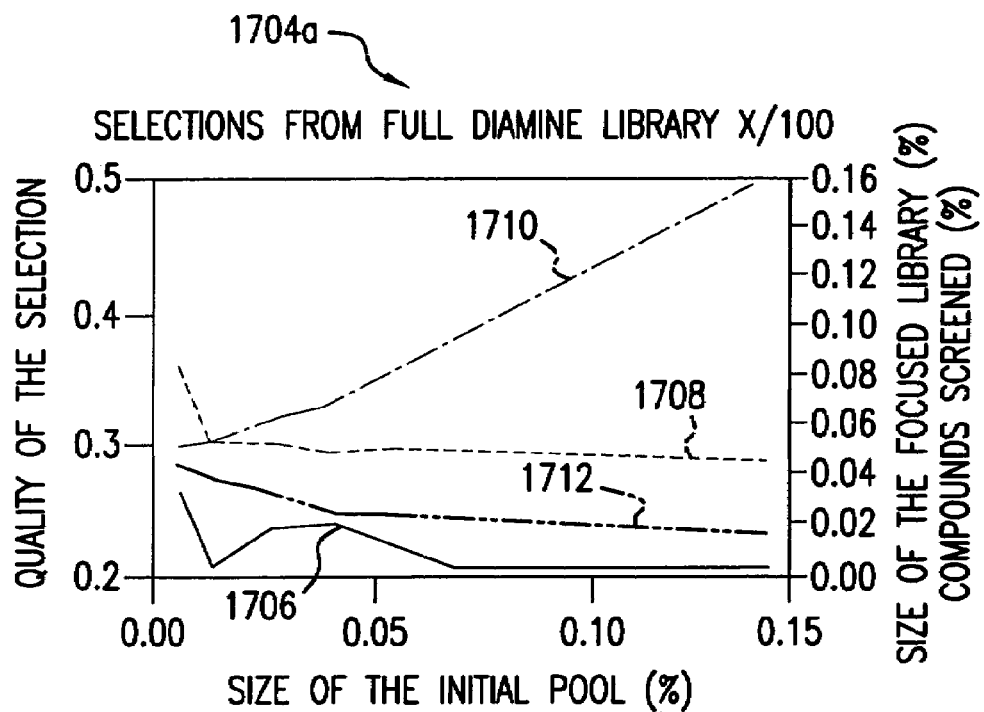
Figure 17D:
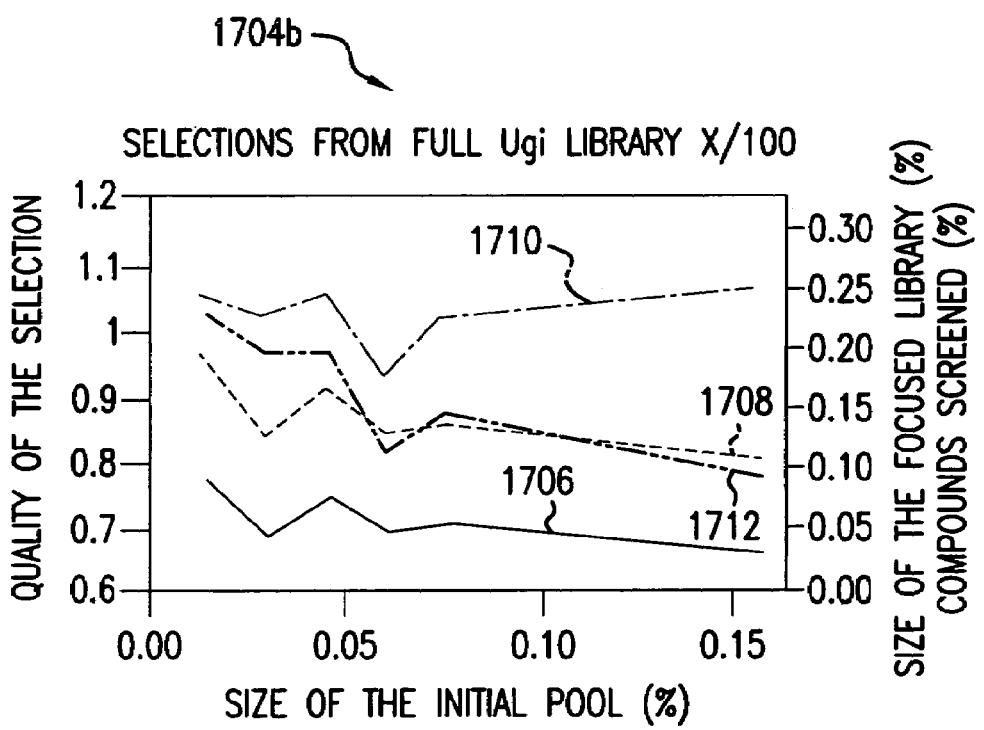

The inventors' experiments indicate that the size N of the initial pool of compounds selected at random (in Step 104) has a lesser effect on the quality of the final selection, as shown in graphs 1602a and 1602b of FIG. 16. However, if these initial pools are too small, they do not provide enough data to generate reliable statistics to determine the "preferred" reagents. If reagent combinations associated with a virtual combinatorial library are selected at random, they will sample all the reagents with the same probability. For example, if only 1,000 reagent combinations are selected from the 300×150×150 diamine virtual combinatorial library, every R1 reagent will be present in only 3 compounds on average, while every R2 and R3 reagent will be present in only 6 compounds on average. In fact, the probability to "miss" at least one reagent from that library is almost 1 if only 1,000 reagent combinations are selected, whereas that probability is almost 0 if 10,000 reagent combinations are selected.

If the initial pool is too small, each of the highest-ranking compounds can contribute completely different reagents, and the subsequent "focused" library can become too large and not focused at all. In this case, the similarity search degrades to a brute-force, random sampling approach, and becomes inefficient. On the other extreme, when the initial pool is too large, the number of "preferred" reagents and the resulting focused library decreases, but the cost (i.e., time) of the initial screening increases. In the inventors' experience, and as shown in FIG. 16, it is optimal to randomly select approximately 0.1% of the compounds in a virtual combinatorial library in the initial stage (Step 104) to achieve a nearly perfect similarity selection and at the same time keep the search practical.

Since the present invention is most useful when applied to massive virtual combinatorial libraries that are intractable by other means, the inventors derived a series of selections from the full diamine virtual combinatorial libraries and Ugi virtual combinatorial libraries containing 706 and 628 million possible enumerated compounds, respectively, using the same query structures of FIG. 10A and FIG. 10B, and varying the same selection parameters (i.e. the size N of the initial pool and the number M of highest-ranking compounds used to derive the focused library). As before, each combination of parameters was tested three times starting from a different random seed, and the results were averaged. The results are summarized in FIG. 17.

Referring to FIG. 17, graphs 1702a and 1704a show the dependence of the quality (i.e., average dissimilarity score) and cost (i.e., number of compound evaluated) of the final selection on the size N of the initial random pool of compounds (Step 104) for the full size diamine virtual combinatorial library. Similarly, graphs 1702b and 1704b show how dependence of the quality (i.e., average dissimilarity score) and cost (i.e., number of compound evaluated) of the final selection on the size N of the initial random pool of compounds (Step 104) for the full size Ugi virtual combinatorial library. Since the quality values relate to dissimilarity scores, the lower the score the better (i.e., more similar) the result. That is, the lower the "Quality of the selection" value, the better the Quality of the selection.

As shown in these graphs, the quality of the combined selections (shown as solid lines 1706) is substantially better than the average quality of the individual selections (shown as the dashed lines 1708). Also shown is that with an increase of the size of the initial pool, the cost of the selection generally increases (as shown by the dash-dotted lines 1710), and the size of the focused library gets smaller (as shown by the dotted lines 1712).

Figure 18:
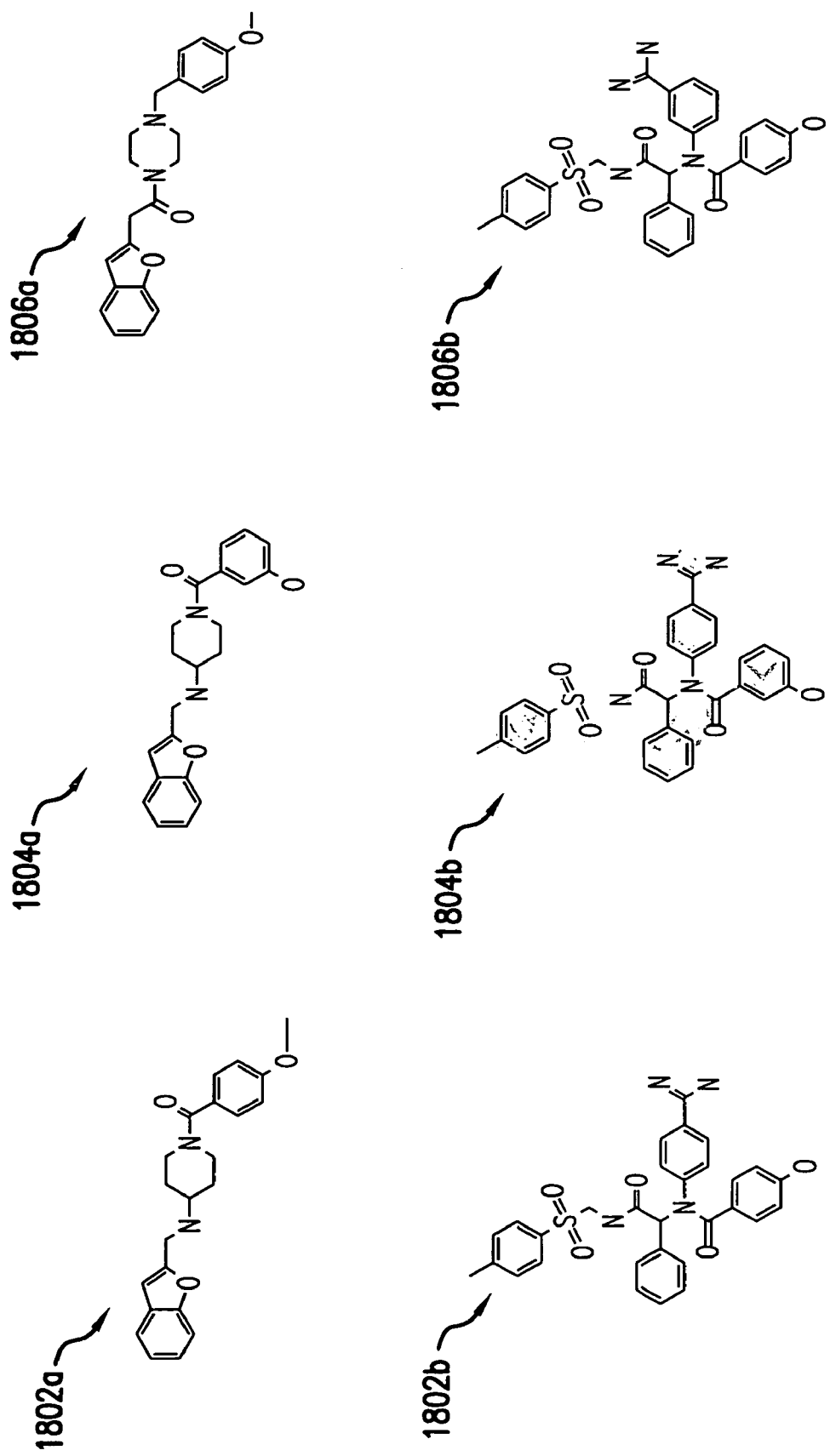
FIG. 18 shows the structures of some of the most similar compounds found during experimental testing of the present invention.

It is clear that excellent selections were obtained in both cases after enumerating and screening on average less than 0.2% of the possible compounds in these virtual combinatorial libraries. In this case the inventors did not know (a priori) the best possible hits, but the average dissimilarity score of the selections derived from the full libraries is substantially lower than that of the corresponding selections from the smaller libraries (0.2 vs. 1.3, and 0.7 vs. 1.4 for the diamine and Ugi libraries, respectively). FIG. 18 shows the structures of some of the most similar compounds found (in step 516). Structure 1802a, 1804a, and 1806a show three structures that were selected from the K most similar compounds associated with the diamine library. Structure 1802b, 1804b, and 1806b show three structures that were selected from the K most similar compounds associated with the Ugi library. An important finding is that in every case the quality of a combined selection after three independent runs (solid lines 1706 in FIG. 17) was substantially better than each individual selection (dashed lines 1708). In fact, the inventors found that better selections can be obtained by using a smaller initial pool and repeating the selection process three times, than by running the selection once from a three times larger pool, both in terms of quality and speed.

These last selections also confirmed that for the diamine library choosing the 100 instead of 50 highest-ranking compounds leads to a better selection, whereas for the Ugi library the improvement in quality is marginal, and is outweighed by the increase in cost (dash-dotted lines 1710). However, as pointed out earlier, the two parameters affecting the outcome of the selection procedure are not entirely independent. When the initial pool is large and the number of highest-ranking compounds selected is small, the resulting focused library is small. In fact, the larger the initial pool, the smaller the focused library (dotted lines 1712). Since the number M of highest-ranking compounds chosen to generate the focused library remains constant, this means that these compounds contribute fewer reagents. A likely consequence of this is the possibility of missing some of the most similar compounds. Imagine, for example, that the single most similar compound in a virtual library is built from two reagents, the first of which, A, represents 70% of the product's structure and the second, B, the remaining 30%. Since the initial compounds are selected at random, it is very unlikely that the product AB will be picked. However, there will be several compounds containing only A (A-compounds) and several compounds containing only B (B-compounds). The larger the number of compounds screened, the more A- and B-compounds will be sampled. Because reagent A represents 70% of the product, the similarity of the A-compounds will be higher than that of the B-compounds. Therefore, if only a small number M of the highest-ranking compounds are chosen to generate the focused library, these will be exclusively A-compounds and the best compound AB will be never discovered. This effect can be seen in FIG. 17 where the quality value (i.e., dissimilarity) of the selection begins to decrease as the size of the initial pool becomes larger. Thus, a larger number M of highest-ranking compounds should be considered in such a case.

An important quality of the algorithm presented herein is the ability to produce very good hit lists in a short period of time. When less than 1% of the virtual compounds need to be enumerated and characterized, the effective performance gain is 100 fold. Additional performance enhancements can be achieved by enumerating the compounds and calculating descriptors in parallel on multiple CPU's. For example, the enumeration and similarity evaluation of all 6.75 million compounds in the diamine library required 34 hours on a dual processor 400 MHz Pentium II machine. The stochastic algorithm using an initial pool of 100,000 and a focused library derived from the 100 highest-ranking compounds produced 88 of the 100 most similar compounds, and required only 30 minutes on the same system. A 1000K/100 selection from the 628 million-membered Ugi library takes less than 2 hours on a 6-processor R10,000 SGI. The inventors believe that this performance represents a dramatic improvement over conventional methodologies, and allows these methods to be used in a routine fashion.

4. Example Environment

Figure 19:
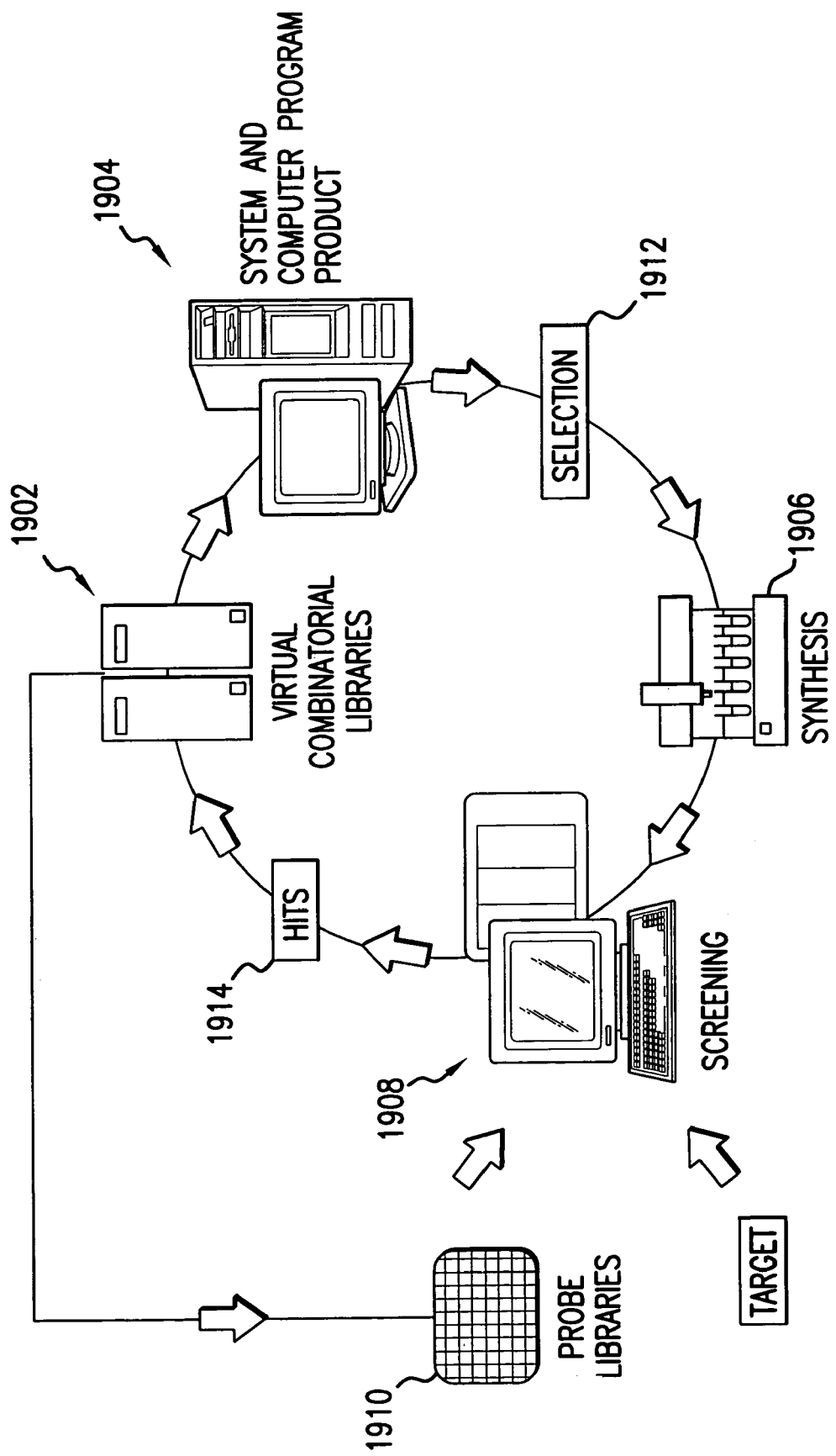
FIG. 19 shows an exemplary environment in which the present invention can be used.

An example environment in which the present invention is useful is described with reference to FIG. 19. As shown in FIG. 19, the example environment includes virtual combinatorial libraries 1902, system and computer program product 1904, synthesis module 1906, and analysis module 1908. Virtual combinatorial library 1902 can be thought of as being essentially a computer representation of a collection of unenumerated chemical compounds. These computer representations are preferably stored in a database. System and computer program product 1904, can be, for example, a dual processor 400 MHZ Intel Pentium II machine running software. It is anticipated that the present invention is part of, or is performed by, system and computer program product 1904. As described below, the present invention can be used in this example environment to optimize the selection of lead compounds.

Initially, a relatively small sample of compounds are selected from the large virtual combinatorial library 1902. Preferably this sample of compounds is selected based on diversity criteria, and possibly considerations of cost, availability of reagents, ease of synthesis, and the like. Diversity is a very important selection criteria in selecting this initial sample of compounds because the sample should be as representative as possible of the entire virtual combinatorial library. The system and method of the present invention, described in FIGS. 7 and 8, can be used to select this diverse sample of compounds. Alternatively, other systems and methods can be used for selecting a diverse sample of compounds from a large combinatorial virtual library. Examples of such systems and methods are described in the article "Stochastic Algorithms for Maximizing Molecular Diversity," which has been incorporated by reference above.

Once a diverse sample of compounds is selected, each compound is physically synthesized to create a probe library 1910. The synthesized compounds of probe library 1908 are then screened by analysis module 1908. Analysis module 1908 preferably assays the synthesized compounds to obtain activity data, such as, enzyme activity data, cellular activity data, toxicology data, and/or bioavailability data. Analysis module 1908 can also analyze the compounds to obtain other pertinent data, such as structure and electronic structure data. Analysis module 1908 can then identify those compounds that possess the most desired properties as lead compounds 1914 (also referred to as "hits"). This can be accomplished by assigning an activity value to each synthesized compound, and selecting those compounds with the highest activity values. Alternatively, lead compounds can be identified by any other method for lead compound identification. For example, the lead compounds may be identified in printed publications, traditional SAR studies, and prior combinatorial chemistry experiments.

In the embodiment where the present invention is used for fast similarity searching of a virtual combinatorial library 1902, these lead compounds (i.e., hits) are the query structures that are used in the present invention (i.e., in steps 504 and 512). When used in such an embodiment, the K (e.g., 100) most similar compounds 1912 to the query structure are obtained. These most similar compounds 1912 can in turn be synthesized by synthesis module 1906. Analysis module 1908 then screens and analyzes the synthesized compounds to obtain new lead compounds 1914. These lead compounds 1914 can then be used as new query structures for use with the present invention. That is, these new lead compounds can be used to generate a new selection of the K most similar compounds 1912. The above described process can be repeated again and again to create additional leads. In other words, the present invention can be used as part of an iterative process for generating lead compounds.

Recently, systems have been developed that permit the automatic chemical synthesis, refinement, and elaboration of bioactive compounds through the tight integration of high-speed parallel synthesis, structure-based design, and cheminformatics. Such systems, known as DirectedDiversity systems, use an iterative optimization process that explores combinatorial space through successive rounds of selection, synthesis, and testing. Examples of these DirectedDiversity systems are described in the following patents and patent application, each of which are incorporated herein by reference in its entirety: U.S. Pat. No. 5,463,564, entitled "System and Method of Automatically Generating Chemical Compounds with Desired Properties"; U.S. Pat. No. 5,574,656 entitled "System and Method of Automatically Generating Chemical Compounds with Desired Properties"; U.S. Pat. No. 5,684,711, entitled, "System, Method, and Computer Program for at Least Partially Automatically Generating Chemical Compounds Having Desired Properties"; U.S. Pat. No. 5,901,069, entitled "System, Method, and Computer Program Product for at Least Partially Automatically Generating Chemical Compounds with Desired Properties from a List of Potential Chemical Compounds to Synthesize"; and U.S. patent application Ser. No. 08/963,870 now U.S. Pat. No. 6,421,612, entitled "System, Method and Computer Program Product For Identifying Chemical Compounds Having Desired Properties."

Unlike traditional combinatorial approaches where the entire library is made and tested in a single conceptual step, DirectedDiversity systems physically synthesize, characterize, and test only a portion of that library at a time. The selection of compounds is carried out by computational search engines that combine optimal exploration of molecular diversity with a directed search based on SAR information accumulated from previous iterations of the integrated machinery.

A central task of DirectedDiversity systems is to select an appropriate set of compounds for physical synthesis and biological evaluation. The present invention provides an efficient system and method for selecting such an appropriate set of compounds. That is, the present invention can be used in the systems described in the above listed patents and application, to generate the list of K compounds to be synthesized during each iteration.

5. Structure of Present Invention

It is anticipated that the present invention can be implemented as hardware, firmware, software or any combination thereof, and can be implemented in one or more computer systems and/or other processing systems. In one embodiment, the present invention is implemented by one or more computer systems capable of carrying out the functionality described herein.

Figure 20:
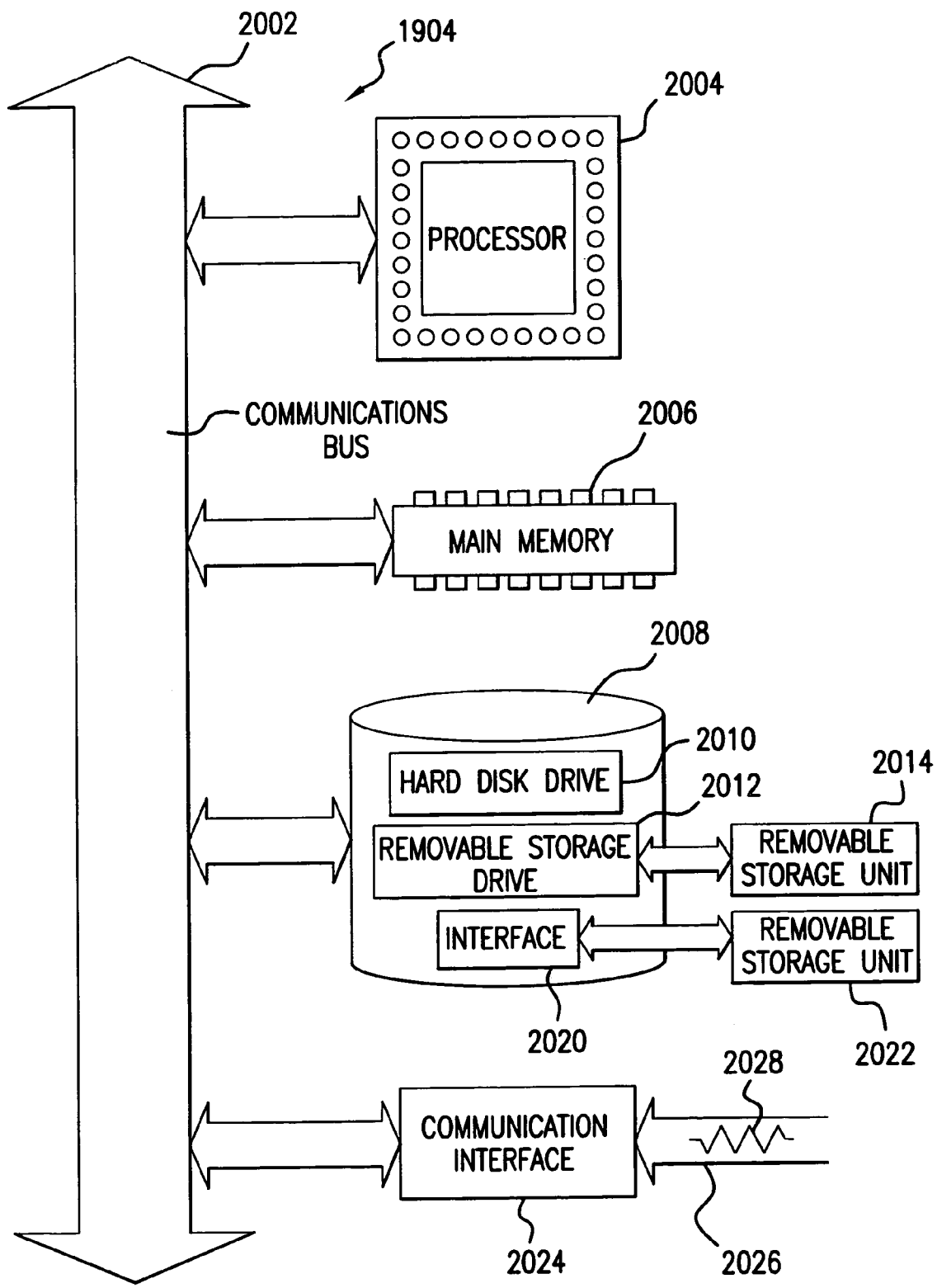
FIG. 20 shows an example of a computer system that can be used to implement the present invention.

Referring to FIG. 20, an example computer system 1904 includes one or more processors, such as processor 2004. Processor 2004 is connected to a communication bus 2002. Various software embodiments are described in terms of this example computer system 1904. After reading this description, it will become apparent to a person skilled in the relevant art how to implement the invention using other computer systems and/or computer architectures.

Computer system 1904 also includes a main memory 2006, preferably random access memory (RAM), and can also include a secondary memory 2008. Secondary memory 2008 can include, for example; a hard disk drive 2010 and/or a removable storage drive 2012, representing a floppy disk drive, a magnetic tape drive, an optical disk drive, etc. Removable storage drive 2012 reads from and/or writes to a removable storage unit 2014 in a well known manner. Removable storage unit 2014, represents a floppy disk, magnetic tape, optical disk, etc. which is read by and written to by removable storage drive 2012. Removable storage unit 2014 includes a computer usable storage medium having stored therein computer software and/or data.

In alternative embodiments, secondary memory 2008 can include other similar means for allowing computer programs or other instructions to be loaded into computer system 1904. Such means can include, for example, a removable storage unit 2022 and an interface 2020. Examples of such can include a program cartridge and cartridge interface (such as that found in video game devices), a removable memory chip (such as an EPROM, or PROM) and associated socket, and other removable storage units 2022 and interfaces 2020 which allow software and data to be transferred from the removable storage unit 2022 to computer system 1904.

Computer system 1904 can also include a communications interface 2024. Communications interface 2024 allows software and data to be transferred between computer system 1904 and external devices. Examples of communications interface 2024 include, but are not limited to a modem, a network interface (such as an Ethernet card), a communications port, a PCMCIA slot and card, etc. Software and data transferred via communications interface 2024 are in the form of signals which can be electronic, electromagnetic, optical or other signals capable of being received by communications interface 2024. These signals 2026 are provided to communications interface via a channel 2028. This channel 2028 carries signals 2026 and can be implemented using wire or cable, fiber optics, a phone line, a cellular phone link, an RF link and other communications channels.

In this document, the terms "computer program medium" and "computer usable medium" are used to generally refer to media such as removable storage device 2012, a hard disk installed in hard disk drive 2010, and signals 2026. These computer program products are means for providing software to computer system 1904.

Computer programs (also called computer control logic) are stored in main memory and/or secondary memory 2008. Computer programs can also be received via communications interface 2024. Such computer programs, when executed, enable the computer system 1904 to perform the features of the present invention as discussed herein. In particular, the computer programs, when executed, enable the processor 2004 to perform the features of the present invention. Accordingly, such computer programs represent controllers of the computer system 1904.

In an embodiment where the invention is implemented using software, the software can be stored in a computer program product and loaded into computer system 1904 using removable storage drive 2012, hard drive 2010 or communications interface 2024. The control logic (software), when executed by the processor 2004, causes the processor 2004 to perform the functions of the invention as described herein.

In another embodiment, the present invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

CONCLUSION

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention. For example, similarity and diversity (dissimilarity) are only two of the many criteria (i.e., fitness functions) that can be used in the present invention. Additional criteria include, but are not limited to, desired properties or property distributions, 2 D and 3 D QSAR predictions, and receptor complementarity.

The present invention has been described above with the aid of functional building blocks illustrating the performance of specified functions and relationships thereof. The boundaries of these functional building blocks have been arbitrarily defined herein for the convenience of the description. A number of combinatorial synthesis strategies employing various functional building blocks and synthesis strategies for assembling libraries therefrom are described in the art. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof. Thus, the breadth and scope of the present invention should not be limited by any of the above-described exemplary embodiments, but should be defined only in accordance with the following claims and their equivalents.

What is claimed is:

1. A computer implemented method of analyzing a non-enumerated virtual library, comprising:
   (a) randomly selecting a set of N reagent combinations from the non-enumerated virtual library, wherein said selected N reagent combinations represent a set of N compounds;
   (b) enumerating said set of N compounds;
   (c) selecting M compounds from said set of N enumerated compounds wherein the selection of M compounds from said set of N enumerated compounds is based on at least one fitness function;
   (d) deconvoluting said M compounds into their associated reagent building blocks;
   (e) generating a focused library of at least one compound based on said building blocks; and
   (f) enumerating at least one compound in said focused library of at least one compound;
   (g) selecting from said at least one compound enumerated from said focused library at least one K compound based on said at least one fitness function; and
   (h) outputting a list of said at least one K compound.

2. The method of claim 1, wherein the at least one fitness function in step (c) is selected from similarity, diversity, and presence or absence at least one characteristic.

3. The method of claim 2, wherein said focused library of at least one compound includes a plurality of compounds.

4. The method of claim 3 wherein step (c) comprises:
   (i) selecting an initial sub-set of M compounds from said set of N enumerated compounds;
   (ii) evaluating said initial sub-set of M compounds based on said fitness function; and
   (iii) refining said initial sub-set of M compounds based on said fitness function, thereby selecting said M compounds.

5. The method of claim 4, wherein step (g) comprises:
   (i) selecting an initial sub-set of at least one K compound from said focused library of compounds;
   (ii) evaluating said initial sub-set of at least one K compounds based on said fitness function; and
   (iii) refining said initial sub-set of at least one K compound based on the fitness function, thereby selecting said at least one K compound.

6. The method of claim 5, wherein said fitness function is related to diversity of a collection of compounds, and wherein step (c) (ii) comprises evaluating a diversity of said initial sub-set of M compounds, and wherein step (c) (iii) comprises refining said initial sub-set of M compounds to increase said diversity of said M compounds.

7. The method of claim 6, wherein said initial sub-set of at least one K compound comprises a plurality of K compounds wherein step (g) (ii) comprises evaluating the diversity of said initial sub-set of K compounds, and wherein step (g) (iii) comprises refining said initial sub-set of K compounds to increase the diversity of said K compounds.

8. The method of claim 3, wherein step (c) comprises:
   (i) characterizing said N enumerated compounds;
   (ii) evaluating said characterized N enumerated compounds based on said fitness function;
   (iii) ranking said characterized N enumerated compounds based on said evaluation; and
   (iv) selecting said M compounds based on said ranking.

9. The method of claim 8, wherein said focused library of at least one compound comprises a plurality of compounds, wherein step (g) comprises:
   (i) characterizing said compound of said focused library of compounds;
   (ii) evaluating said characterized compound of said focused library of compounds based on said fitness function;
   (iii) ranking said characterized compounds of said focused library of compounds based on said evaluation; and
   (iv) selecting said K compounds based on said ranking.

10. The method of claim 9, wherein step (c) (i) comprises characterizing said N enumerated compounds using a set of molecular descriptors.

11. The method of claim 10, wherein step (g) (i) comprises characterizing compounds of said enumerated focused library of compounds using said set of molecular descriptors.

12. The method of claim 9, wherein said fitness function is related to a similarity to one or more query structures, and wherein step (c) (ii) comprises evaluating similarity between said N enumerated compounds and said one or more query structures.

13. The method of claim 12, wherein at least one of the following similarity measures is used in step (a) (ii) for evaluating similarity between each compounds and said one or more query structures:
   (1) similarity in number of atoms, bonds and rings of the same types;
   (2) similarity in shape and surface characteristics;
   (3) similarity in electron density distribution;
   (4) similarity based on common substructure;
   (5) similarity based on the presence and orientation of pharmacophoric groups;
   (6) similarity in binding affinity; and
   (7) similarity in degree of conformational overlap with a know receptor binder.

14. The method of claim 12, wherein step (g) (ii) comprises evaluating similarity between compounds of said enumerated focused library of compounds and said one or more query structures, and wherein the same similarity measure is used for evaluating similarity in step (c) (ii) and step (g) (ii).

15. The method of claim 8, wherein said fitness function is related to at least one desired characteristic, and wherein step (c) (ii) comprises evaluating N enumerated compounds to determine an extent to which the N enumerated compounds possess the at least one desired characteristic.

16. The method of claim 15, therein the at least one desired characteristic comprises at least one of the following:
   (1) a desired physical property;
   (2) a desired chemical property;
   (3) a desired functional property; and
   (4) a desired bioactive property.

17. A computer based system for analyzing a non-enumerated virtual library, comprising:
   means for randomly selecting a set of N reagent combinations from the virtual library, wherein said selected N reagent combinations represent a set of N compounds;
   means for enumerating said set of N compounds;
   means for selecting M compounds of said set of N enumerated compounds based on a fitness function;
   means for deconvoluting said M compounds into their associated reagent building blocks;
   means for generating a focused library of compounds based on said building blocks;
   means for enumerating a plurality of said compounds of said focused library of compounds;
   means for selecting at least one K compound of said enumerated compounds of said focused library based on the fitness function,
   means for outputting to a user said at least one selected K compound to be synthesized.

* * * * *